(12) United States Patent
Barrett et al.

(10) Patent No.: US 12,357,577 B1
(45) Date of Patent: Jul. 15, 2025

(54) PHARMACEUTICAL FORMULATIONS AND USES THEREOF

(71) Applicant: Gilead Sciences, Inc., Foster City, CA (US)

(72) Inventors: Kimberly T. Barrett, Pacifica, CA (US); Elaine Bunyan, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/431,038

(22) Filed: Feb. 2, 2024

(51) Int. Cl.
*A61K 9/20* (2006.01)
*A61K 9/28* (2006.01)
*A61K 31/706* (2006.01)

(52) U.S. Cl.
CPC .......... *A61K 9/2054* (2013.01); *A61K 9/2009* (2013.01); *A61K 9/2027* (2013.01); *A61K 9/2866* (2013.01); *A61K 31/706* (2013.01)

(58) Field of Classification Search
CPC ...... A61K 9/20; A61K 9/2004; A61K 9/2018; A61K 9/2009; A61K 9/205; A61K 9/2054; A61K 9/2059
See application file for complete search history.

(56) References Cited

U.S. PATENT DOCUMENTS

| | | | |
|---|---|---|---|
| 4,816,570 A | 3/1989 | Farquhar | |
| 4,894,376 A | 1/1990 | Morad et al. | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,475,985 B1 | 11/2002 | Wagner et al. | |
| 6,476,030 B1 | 11/2002 | Carling et al. | |
| 6,639,059 B1 | 10/2003 | Kochkine et al. | |
| 6,656,915 B1 | 12/2003 | Bantia et al. | |
| 6,909,011 B2 | 6/2005 | Skranc et al. | |
| 7,078,403 B1 | 7/2006 | Wu et al. | |
| 7,105,493 B2 | 9/2006 | Sommadossi et al. | |
| 7,125,855 B2 | 10/2006 | Bhat et al. | |
| 7,166,604 B2 | 1/2007 | Watson et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 | 9/2010 | Becker et al. | |
| 7,807,653 B2 | 10/2010 | Cook et al. | |
| 7,842,672 B2 | 11/2010 | Boojamra et al. | |
| 7,951,787 B2 | 5/2011 | McGuigan | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |
| 8,455,451 B2 | 6/2013 | Cho et al. | |
| 8,853,171 B2 | 10/2014 | Butler et al. | |
| 8,871,737 B2 | 10/2014 | Smith et al. | |
| 8,889,159 B2 | 11/2014 | Clearly et al. | |
| 8,980,865 B2 | 3/2015 | Wang | |
| 9,090,642 B2 | 7/2015 | Cho et al. | |
| 9,243,022 B2 | 1/2016 | Beigelman et al. | |
| 9,249,174 B2 | 2/2016 | Beigelman et al. | |
| 9,278,990 B2 | 3/2016 | Smith et al. | |
| 9,388,208 B2 | 7/2016 | Clarke et al. | |
| 9,393,256 B2 | 7/2016 | Ray et al. | |
| 9,452,154 B2 | 9/2016 | Delaney et al. | |
| 9,481,703 B2 | 11/2016 | Kalayanov et al. | |
| 9,487,544 B2 | 11/2016 | Cho et al. | |
| 9,504,701 B2 | 11/2016 | Casola et al. | |
| 9,540,411 B2 | 1/2017 | Kalayanov et al. | |
| 9,549,941 B2 | 1/2017 | Cleary et al. | |
| 9,605,018 B2 | 3/2017 | Wang et al. | |
| 9,616,076 B2 | 4/2017 | Casola et al. | |

(Continued)

FOREIGN PATENT DOCUMENTS

| | | |
|---|---|---|
| CN | 108084192 | 5/2018 |
| CN | 109748944 | 5/2019 |

(Continued)

OTHER PUBLICATIONS

"Medical Microbiology," Fourth Edition, Baron (ed.), University of Texas Medical Branch at Galveston, 1996, Chapters 59 and 72, 38 pages.

"Molecular Nuclear Medicine," First Edition, Wang (ed.), May 31, 2001, pp. 388-391, 11 pages (with English translation).

"Molecular Nuclear Medicine," Second Edition, Wang (ed.), Union Medical College of China, 2004, pp. 417-419 (with English translation).

"Veterinary Microbiology," 4th Edition, Lu (ed.), 2007, p. 304: paragraph 2, p. 408: paragraph 1, p. 419: paragraphs 1-2, 7 pages (with English translation).

[No Author Listed], "Definitive Rules for Nomenclature of Organic Chemistry," Journal of the American Chemistry Society, Nov. 1, 1960, 82(21):5545-5574.

(Continued)

*Primary Examiner* — Micah Paul Young
(74) *Attorney, Agent, or Firm* — Fish & Richardson P.C.

(57) ABSTRACT

Pharmaceutical formulations, particularly solid oral dosage forms (e.g., tablets) comprising (i) the compound of Formula I in an amount of about 40 wt % to about 70 wt %, (ii) a filler, (iii) a disintegrating agent, (iv) and a lubricant are disclosed, as are uses thereof.

27 Claims, 6 Drawing Sheets

(56) References Cited

U.S. PATENT DOCUMENTS

| | | |
|---|---|---|
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,938,283 B2 | 4/2018 | Pandey et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 8/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,225,508 B1 | 1/2022 | Baric et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,344,565 B2 | 5/2022 | Axt et al. |
| 11,377,456 B2 | 7/2022 | Souza et al. |
| 11,382,926 B2 | 7/2022 | Clarke et al. |
| 11,491,169 B2 | 11/2022 | Cihlar |
| 11,492,353 B2 | 11/2022 | Mackman et al. |
| 11,541,071 B1 | 1/2023 | Liang et al. |
| 11,597,742 B2 | 3/2023 | Brak et al. |
| 11,613,553 B2 | 3/2023 | Badalov et al. |
| 11,638,715 B2 | 5/2023 | Burns et al. |
| 11,660,307 B2 | 5/2023 | Cihlar et al. |
| 11,701,372 B2 | 7/2023 | Ellis et al. |
| 11,780,844 B2 | 9/2023 | Bartlett et al. |
| 11,814,406 B2 | 10/2023 | Bunyan et al. |
| 11,845,755 B2 | 12/2023 | Bartlett et al. |
| 11,851,438 B2 | 12/2023 | Bartlett et al. |
| 11,903,953 B2 | 2/2024 | Cihlar |
| 11,926,645 B2 | 3/2024 | Bunyan et al. |
| 11,939,347 B2 | 3/2024 | Byun et al. |
| 11,975,012 B2 | 5/2024 | Cihlar |
| 11,975,017 B2 | 5/2024 | Larson et al. |
| 12,012,431 B2 | 6/2024 | Mohan |
| 12,030,906 B2 | 7/2024 | Brak et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0129764 A1* | 6/2005 | Vergez ............... A61P 29/00 514/406 |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0065512 A1 | 3/2010 | Bjorsvik |
| 2010/0129437 A1 | 5/2010 | Gaillard |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Clark et al. |
| 2018/0346504 A1 | 12/2018 | Brak et al. |
| 2019/0023745 A1 | 1/2019 | Baric et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0061806 A1 | 3/2021 | Mackman et al. |
| 2021/0283150 A1 | 9/2021 | Cihlar et al. |
| 2021/0309689 A1 | 10/2021 | Badalov et al. |
| 2021/0330685 A1 | 10/2021 | Ellis et al. |
| 2021/0393653 A1 | 12/2021 | Cihlar et al. |
| 2021/0393659 A1 | 12/2021 | Clarke et al. |
| 2021/0403497 A1 | 12/2021 | Butler et al. |
| 2022/0081462 A1* | 3/2022 | Chun .................. C07D 487/04 |
| 2022/0175805 A1 | 6/2022 | Cihlar |
| 2022/0280549 A1 | 9/2022 | Larson et al. |
| 2022/0354873 A1 | 11/2022 | Axt et al. |
| 2022/0356196 A1 | 11/2022 | Byun et al. |
| 2023/0027727 A1 | 1/2023 | Clarke et al. |
| 2023/0040586 A1 | 2/2023 | Byun et al. |
| 2023/0125751 A1 | 4/2023 | Mackman et al. |
| 2023/0151043 A1 | 5/2023 | Bunyan et al. |
| 2023/0233587 A1 | 7/2023 | Cihlar |
| 2023/0279013 A1 | 9/2023 | Bartlett et al. |
| 2023/0279014 A1 | 9/2023 | Bartlett et al. |
| 2023/0279015 A1 | 9/2023 | Bartlett et al. |
| 2023/0295172 A1 | 9/2023 | Bartlett et al. |
| 2023/0295214 A1 | 9/2023 | Badalov et al. |
| 2023/0322813 A1 | 10/2023 | Chun et al. |
| 2023/0346812 A1 | 11/2023 | Cihlar et al. |
| 2023/0348519 A1 | 11/2023 | Brak et al. |
| 2024/0009220 A1 | 1/2024 | Bannister et al. |
| 2024/0024341 A1 | 1/2024 | Ellis et al. |
| 2024/0043466 A1 | 2/2024 | Dempah et al. |
| 2024/0051962 A1 | 2/2024 | Dempah et al. |
| 2024/0091251 A1 | 3/2024 | Larson et al. |
| 2024/0131045 A1 | 4/2024 | Davis et al. |
| 2024/0150359 A1 | 5/2024 | Bartlett et al. |
| 2024/0189334 A1 | 6/2024 | Davis et al. |

(56) References Cited

U.S. PATENT DOCUMENTS

| | | |
|---|---|---|
| 2024/0207291 A1 | 6/2024 | Bilello |
| 2024/0239830 A1 | 7/2024 | Bremner et al. |
| 2024/0246986 A1 | 7/2024 | Bartlett et al. |
| 2024/0287109 A1 | 8/2024 | Byun et al. |
| 2024/0317790 A1 | 9/2024 | Bunyan et al. |

FOREIGN PATENT DOCUMENTS

| | | |
|---|---|---|
| CN | 110330540 | 10/2019 |
| CN | 110724174 | 1/2020 |
| CN | 110776512 | 2/2020 |
| CN | 111171078 | 5/2020 |
| CN | 111205294 | 5/2020 |
| CN | 111205327 | 5/2020 |
| CN | 111233869 | 6/2020 |
| CN | 111265532 | 6/2020 |
| CN | 111440176 | 7/2020 |
| CN | 111548384 | 8/2020 |
| CN | 111961057 | 11/2020 |
| CN | 202011613943.3 | 12/2020 |
| CN | 112778310 | 5/2021 |
| CN | 202110562244.9 | 5/2021 |
| CN | 113754665 | 6/2021 |
| CN | 113185519 | 7/2021 |
| CN | 113248508 | 8/2021 |
| CN | 113292565 | 8/2021 |
| CN | 113387954 | 9/2021 |
| CN | 113735862 | 9/2021 |
| CN | 113698405 | 11/2021 |
| CN | 114292272 | 12/2021 |
| CN | 113999237 | 1/2022 |
| CN | 114181258 | 3/2022 |
| CN | 114409655 | 4/2022 |
| CN | 114437159 | 5/2022 |
| CN | 114621229 | 6/2022 |
| CN | 114765979 | 7/2022 |
| CN | 114869893 | 8/2022 |
| CN | 114869893 A * | 8/2022 |
| CN | 115521316 | 12/2022 |
| CN | 115583954 | 1/2023 |
| CN | 116172966 | 5/2023 |
| CN | 116970014 | 10/2023 |
| IN | 202121023147 | 5/2021 |
| IN | 202134041493 | 9/2021 |
| IN | 202011021676 | 11/2021 |
| JP | 2005185235 | 7/2005 |
| JP | 2005187428 | 7/2005 |
| JP | 2017512797 | 5/2017 |
| WO | WO1991019721 | 12/1991 |
| WO | WO1999045029 | 9/1999 |
| WO | WO2000056734 | 9/2000 |
| WO | WO2000075157 | 12/2000 |
| WO | WO2001032153 | 5/2001 |
| WO | WO2001060315 | 8/2001 |
| WO | WO2001090121 | 11/2001 |
| WO | WO2001091737 | 12/2001 |
| WO | WO2001092282 | 12/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046159 | 6/2004 |
| WO | WO2004046331 | 6/2004 |
| WO | WO2004112687 | 12/2004 |
| WO | WO2005009418 | 2/2005 |
| WO | WO2005092877 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO2007062542 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO2007113294 | 10/2007 |
| WO | WO2007135134 | 11/2007 |
| WO | WO2008005542 | 1/2008 |
| WO | WO2008011406 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |
| WO | WO2009009951 | 1/2009 |
| WO | WO2009018609 | 2/2009 |
| WO | WO2009131926 | 10/2009 |
| WO | WO2009132123 | 10/2009 |
| WO | WO2009132135 | 10/2009 |
| WO | WO2010002877 | 1/2010 |
| WO | WO2010036407 | 4/2010 |
| WO | WO2010039548 | 4/2010 |
| WO | WO2010093608 | 8/2010 |
| WO | WO2010099458 | 9/2010 |
| WO | WO2010108140 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO2011080568 | 7/2011 |
| WO | WO2011100131 | 8/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012121764 | 9/2012 |
| WO | WO2012142523 | 10/2012 |
| WO | WO2012158643 | 11/2012 |
| WO | WO2013039861 | 3/2013 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2014209979 | 12/2014 |
| WO | WO2016107833 | 12/2014 |
| WO | WO2015054465 | 4/2015 |
| WO | WO2015069939 | 5/2015 |
| WO | WO2015173164 | 11/2015 |
| WO | WO2015200205 | 12/2015 |
| WO | WO2015200219 | 12/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017049060 | 3/2017 |

(56) References Cited

FOREIGN PATENT DOCUMENTS

| | | |
|---|---|---|
| WO | WO2017165489 | 9/2017 |
| WO | WO2017184668 | 10/2017 |
| WO | WO2018085307 | 5/2018 |
| WO | WO2018099946 | 6/2018 |
| WO | WO2018121678 | 7/2018 |
| WO | WO2018145148 | 8/2018 |
| WO | WO2018204198 | 11/2018 |
| WO | WO2018217906 | 11/2018 |
| WO | WO2019014247 | 1/2019 |
| WO | WO2019053696 | 3/2019 |
| WO | WO2019079594 | 4/2019 |
| WO | WO2019113462 | 6/2019 |
| WO | WO2022098371 | 11/2020 |
| WO | WO2021021717 | 2/2021 |
| WO | WO2021040356 | 3/2021 |
| WO | WO2021050961 | 3/2021 |
| WO | WO2021102363 | 5/2021 |
| WO | WO2021147236 | 7/2021 |
| WO | WO2021154530 | 8/2021 |
| WO | WO2021175296 | 9/2021 |
| WO | WO2021188915 | 9/2021 |
| WO | WO2021195661 | 9/2021 |
| WO | WO2022142477 | 9/2021 |
| WO | WO2021202907 | 10/2021 |
| WO | WO2021207049 | 10/2021 |
| WO | WO2021213288 | 10/2021 |
| WO | WO2021222807 | 11/2021 |
| WO | WO2021236570 | 11/2021 |
| WO | WO2022143473 | 12/2021 |
| WO | WO2022008642 | 1/2022 |
| WO | WO2022029704 | 2/2022 |
| WO | WO2022047065 | 3/2022 |
| WO | WO2022047441 | 3/2022 |
| WO | WO2022081870 | 4/2022 |
| WO | WO2022093895 | 5/2022 |
| WO | WO2022165386 | 8/2022 |
| WO | WO2022174194 | 8/2022 |
| WO | WO2022197950 | 9/2022 |
| WO | WO2022217153 | 10/2022 |
| WO | WO2022217154 | 10/2022 |
| WO | WO2022217155 | 10/2022 |
| WO | WO2022218274 | 10/2022 |
| WO | WO2022222994 | 10/2022 |
| WO | WO2022251663 | 12/2022 |
| WO | WO2022265964 | 12/2022 |
| WO | WO2023009977 | 2/2023 |
| WO | WO2023022216 | 2/2023 |
| WO | WO2023056335 | 4/2023 |
| WO | WO2023078416 | 5/2023 |
| WO | WO2023122212 | 6/2023 |
| WO | WO2023167938 | 9/2023 |
| WO | WO2023167944 | 9/2023 |
| WO | WO2023239665 | 12/2023 |
| WO | WO2024006376 | 1/2024 |
| WO | WO2024006461 | 1/2024 |
| WO | WO2024054618 | 3/2024 |
| WO | WO2024076951 | 4/2024 |

OTHER PUBLICATIONS

Adlington et al., "Synthesis of novel C-nucleosides with potential applications in combination and parallel synthesis," Tetrahedron Letters, 2000, 41:575-578.

Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.

Al-Aly et al., "High-dimensional characterization of post-acute sequelae of Covid-19," Nature, Jun. 2021, 594(7862): 259-64.

Al-Aly et al., "Long Covid after breakthrough SARS-CoV-2 infection," Nature Medicine. Jul. 2022, 28(7): 1461-7.

Alavi et al., "Severe SARS-CoV-2 infection in a 32-week pregnant woman treated with Remdesivir-Dexamethasone combination therapy: A case report," Clinical Case Reports, Aug. 2022, 10(8): e6241.

Aleissa et al., "New Perspectives on Antimicrobial Agents: Remdesivir Treatment for Covid-19," Antimicrobial Agents and Chemotherapy, Dec. 2020, 65(1): 18 pages.

Alessandrini et al., "Synthesis of Differently Protected 1-C-methyl-ribofuranoses Intermediates for the Preparation of Biologically Active 1'-C-methyl-ribonucleosides," Journal of Carbohydrate Chemistry, 2008, 27(5):332-344.

Ali et al., "Quantitative structure-activity relationships (QSAR) of two series of O-aryl or N-acyl O-ethyl phosphoramidate and phosphorodiamidate fungicides incorporating amino acid ethyl esters," Bulletin of Environmental Contamination and Toxicology, 2000, 65(4):415-420.

Amstutz et al., "Effects of remdesivir in patients hospitalised with Covid-19: A systematic review and individual patient data meta-analysis of randomised controlled trials," The Lancet Respiratory Medicine, Feb. 2023, 11(5): 453-464.

Anderson et al., "The use of convalescent plasma therapy and remdesivir in the successful management of a critically ill obstetric patient with novel coronavirus 2019 infection: A case report," Case Reports in Women's Health, May 2020, 27: 3 pages.

Anonymous [online], "University of Alabama & Multi-Center Collaboration Help Develop Remdesivir with Gilead Thanks to $37.5m from NIH," TrialSiteNews.com, retrieved on Mar. 13, 2023, URL <https://www.trialsitenews.com/a/university-of-alabama-multi-center-collaboration-help-develop-remdesivir-with-gilead-thanks-to-37-5m-from-nih>, Mar. 1, 2020, 5 pages.

Anonymous, "Gillings research on broad-spectrum antiviral could aid public health response to coronavirus outbreaks",—UNC Gillings School of Global Public Health, Jan. 10, 2020, retrieved on May 13, 2021, retrieved from URL <"https://sph.unc.edu/sph-news/gillings-research-on-broad-spectrum-antiviral-could-aid-public-health-response-to-coronavirus-outbreaks/">, 5 pages.

Anoshchenko et al., "Pharmacokinetics, Safety, and Tolerability of Obeldesivir (OBV; GS-5245) in Healthy Participants," Poster P2620, Presented at European Congress of Clinical Microbiology and Infectious Diseases (ECCMID), Apr. 15-18, 2023, 1 page.

Arimilli et al., "Synthesis, In Vitro Biological Evaluation and Oral Bioavailability of 9-[2-(phosphonomethoxy)propyl]adenine (PMPA) Prodrugs," Antiviral Chemistry & Chemotherapy, 1997, 8(6):557-564.

Asbun et al., "Synthesis of 5-substituted Pyrimidines. II," Journal of Organic Chemistry, 1968, 31:140-142.

Assiri et al., "Epidemiological, Demographic, and Clinical Characteristics of 47 Cases of Middle East Respiratory Syndrome Coronavirus Disease From Saudi Arabia: A Descriptive Study," The Lancet Infectious Diseases, Sep. 2013, 13(9):752-61.

Austin, "An Introduction to Propensity Score Methods for Reducing the Effects of Confounding in Observational Studies," Multivariate behavioral research, May 2011, 46(3): 399-424.

Baker et al., "Prodrugs of 9-Beta-D-Arabinofuranosyladenine. 1. Synthesis and Evaluation of some 5'-(O-Acyl) Derivatives," Journal of Medicinal Chemistry, Dec. 1978, 21(12): 1218-1221.

Ballini et al., "Enantioselective Synthesis of the Lactone Moiety of the Mevinic Acids using D-Xylose as a Chiral Precursor," Journal of the Chemical Society, Perkin Transactions 1, 1991, pp. 490-491.

Balzarini et al., "Inhibition of Feline (FIPV) and Human (SARS) Coronavirus by Semisynthetic Derivatives of Glycopeptide Antibiotics," Antiviral Research, 2006, 72:20-33.

Bandini et al., "Indium tribromide: a highly effective catalyst for the addition of trimethylsilyl cyanide to α-hetero-substituted ketone," Tetrahedron Letters, 2001, 42:3041-3043.

Barker et al., "2,3,5-Tri-O-benzyl-D-ribosyl and -L-arabinosyl Bromides," Journal of Organic Chemistry, 1961, 26(11):4605-4609.

Barl et al., "The halogen/magnesium-exchange using iPrMgCl•LiCl and related exchange reagents," Heterocycles, Jan. 2014, 88(2):827-844.

Barnes, "Corticosteroids: The drugs to beat," European Journal of Pharmacology, Mar. 8, 2006, 533(1-3):2-14.

Barrett et al., "Risk for Newly Diagnosed Diabetes >30 Days After SARS-CoV-2 Infection Among Persons Aged <18 Years—United States, Mar. 1, 2020-Jun. 28, 2021," MMWR Morbidity and Mortality Weekly Report, Jan. 14, 2022, 71(2):59-65.

(56) References Cited

OTHER PUBLICATIONS

Beaucourt et al., "Ribavirin: a drug active against many viruses with multiple effects on virus replication and propagation. Molecular basis of ribavirin resistance," Current Opinions in Virology, May 2014, 8:10-15.
Beer et al., "Characteristics of Filoviridae: Marburg and Ebola Viruses," Naturwissenschaften, 1999, 86:8-17.
Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16.
Beigel et al., "Remdesivir for the Treatment of Covid-19—Final Report," New. England Journal of Medicine, Nov. 5, 2020, 383(19): 1813-1826.
Belokon et al., "Optimized catalysts for the asymmetric addition of trimethylsilyl cyanide to aldehydes and ketones," Tetrahedron, 2001, 57: 771-779.
Benksim et al., "A Novel Stereospecific Synthesis of Glycosyl Cyanides from 1,2-O-sulfinyl Derivatives," Organic Letters, 2004, 6(22): 3913-3915.
Benzaria et al., "Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability," J. Med. Chem. 1996, 39(25): 4958-4965.
Bhimraj et al., "Infectious Diseases Society of America guidelines on the treatment and management of patients with Covid-19," Clinical Infectious Diseases, Apr. 27, 2020, 20 pages.
Bio et al., "Practical Synthesis of a Potent Hepatitis C Virus RNA Replication Inhibitor," J. Org. Chem., 2004, 69(19): 6257-6266.
Bobeck et al., "Advances in Nucleoside Monophosphate Prodrugs as Anti-HCV Agents," Antiviral Therapy, 2010, 15: 935-950.
Bobrowski et al., "Synergistic and Antagonistic Drug Combinations against SARS-CoV-2", Molecular Therapy, Feb. 2021, 29(2):873-885.
Boglione et al., "Risk factors and incidence of long-Covid syndrome in hospitalized patients: does remdesivir have a protective effect?," QJM: An International Journal of Medicine, Dec. 2021, 114(12):865-871.
Bojack et al., "Design and Synthesis of Inhibitors of Adenosine and AMP Deaminases," Organic Letters, 2001, 3(6):839-842.
Bonilauri et al., "Animal Coronaviruses and SARS-COV-2 in Animals, What Do We Actually Know?," Life, Feb. 2021, 11(2): 1-17.
Bornholdt et al., "A Two-Antibody Pan-Ebolavirus Cocktail Confers Broad Therapeutic Protection in Ferrets and Nonhuman Primates," Cell Host Microbe, Jan. 2019. 25(1): 49-58, e1-e5.
Bowe et al., "Acute and postacute sequelae associated with SARS-CoV-2 reinfection." Nature Medicine, Nov. 2022, 28(11): 2398-405.
Bowe et al., "Kidney Outcomes in Long Covid," Journal of the American Society of Nephrology, Nov. 2021, 32(11): 2851-62.
Bowie et al., "RIG-I: tri-ing to discriminate between self and non-self RNA," Trends in Immunology, Apr. 2007, 28(4): 147-150.
Boyer et al., "Pathogenesis, diagnosis and management of hepatitis C," Journal of Hepatology, 2000, 32:98-112.
Bozza, "Zika Outbreak, Brazil 2015," ISARIC, 2015, 28 pages.
Bradley et al., "The Management of Community-Acquired Pneumonia in Infants and Children Older Than 3 Months of Age: Clinical Practice Guidelines by the Pediatric. Infectious Diseases Society and the Infectious Diseases Society of America," Pediatric Community Pneumonia Guidelines, Clinical Infectious Diseases, Oct. 2011.53(7):e25-e76.
Brands et al., "Crystallization-Induced Diastereomer Transformations," Chem. Rev., 2006, 106(7): 2711-2733.
Brannan et al., "Post-exposure immunotherapy for two ebolaviruses and Marburg virus in nonhuman primates," Nature Communications, Jan. 2019, 10: 105, 10 pages.
Brittain, "Polymorphism in Pharmaceutical Solids," 2nd Edition, 2009, pp. 183-226, Informa Healthcare USA, Inc.
Brookes et al., "Impaact 2032: Remdesivir PK and safety in pregnant and non-pregnant women with Covid-19 [CROI Abstract 676]," Abstracts from CROI 2022. Conference on Retroviruses and Opportunistic Infections, Feb. 2022. 1 page.
Brotschi et al., "Bipyridyl and biphenyl DNA: A recognition motif based on interstrand aromatic stacking," Chemistry—A European Journal, 2005, 11(6):1911-1923.
Brown et al., "Broad spectrum antiviral remdesivir inhibits human endemic and zoonotic deltacoronaviruses with a highly divergent RNA dependent RNA polymerase", Antiviral Research, Jun. 21, 2019, 169:1-31.
Brown et al., "Consistent Effects of Early Remdesivir on Symptoms and Disease Progression Across At-Risk Outpatient Subgroups: Treatment Effect Heterogeneity in Pinetree Study," Infectious Diseases and Therapy, Apr. 2023, 12: 1189-1203.
Brown, "Progress towards improving antiviral therapy for hepatitis C virus polymerase inhibitors," Part O: Nucleoside Analogues, 2009, 18:709-725.
Budi et al., "Remdesivir for pregnancy: A systematic review of antiviral therapy for Covid-19," Heliyon, Jan. 2022,8(1): 10 pages.
Bullard-Feibelman et al., "The FDA-approved drug Sofosbuvir inhibits Zika Virus infection," Antiviral Res., Jan. 1, 2018, 137: 134-140.
Burns, "A Glimmer of Hope for Fatal Feline Disease," JAVMAnews, Dec. 15, 2017, 5 pages.
Burwick et al., "Compassionate Use of Remdesivir in Pregnant Women With Severe Coronavirus Disease," Clinical Infectious Diseases, Dec. 2021, 73(1): e3996-e4004.
Butora et al., "Synthesis and HCV inhibitory properties of 9-deaza- and 7,9-dideaza-7-oxa-2'-C-methyladenosine," Bioorganic & Medicinal Chemistry, 2007, 15(15): 5219-5229.
Bwire et al., "Sudan Ebola virus (SUDV) outbreak in Uganda, 2022: lessons learnt and future priorities for sub-Saharan Africa," BMC Medicine, Apr. 2023, 21: 144, 3 pages.
Cabirol et al., "Robust and Efficient, yet Uncatalyzed, Synthesis of Triarylsilyl-protected Cyanohydrins from Ketones," J. Org. Chem., 2008, 73:2446-2449.
Caira, "Crystalline Polymorphism of Organic Compounds," Topics in Current Chemistry, 1998, 198: 163-208.
Cales et al., "Treatment of liver fibrosis: clinical aspects," Gastroentérologie Clinique et Biologique, 2009, 33(10-11): 958-966.
Calisher et al., "Antigenic Relationships between Flaviviruses as Determined by Cross-neutralization Tests with Polyclonal Antisera," Journal of General Virology, 1989, 70: 37-43.
Camps, "Studies on Structurally Simple -αβ-butenolides-II," Tetrahedron, 1982, 38(15): 2395-2402.
Cao et al., "The Adenosine Analog Prodrug ATV006 is Orally Bioavailable and has Preclinical Efficacy Against Parental SARS-CoV-2 and Variants," Science Translational Medicine, May 2022, 14(661), 16 pages.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
Carroll, "Robust Antiviral Efficacy upon Administration of a Nucleoside Analog to Hepatitis C Virus-Infected Chimpanzees," Antimicrobial Agents and Chemotherapy, 2009, 53(3): 926-934.
Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol" ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021 retrieved from URL <"https://www.chemsrc.com/en/cas/54-05-7_419322.html">, 16 pages.
CAS Registry No. 1809249-37-3, "L-Alanine, N-[(S)-hydroxyphenoxyphosphinyl]-2-ethylbutyl ester, 6-ester with 2-C-

(56) References Cited

OTHER PUBLICATIONS (4-aminopyrrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_rn=1809249-37-3">, 3 pages.

Center for Disease Control and Prevention (CDC) [online], "Animals & Covid-19," Covid-19, last updated Apr. 7, 2023, retrieved on Aug. 29, 2023, retrieved from URL: <https://www.cdc.gov/coronavirus/2019-ncov/daily-life-coping/animals.html>, 4 pages.

Center for Disease Control and Prevention (CDC) [online], "Classifications & Definitions," Covid-19, last updated Mar. 20, 2023, retrieved on Aug. 29, 2023 retrieved from URL: <https://www.cdc.gov/coronavirus/2019-ncov/variants/variant-classifications.html>, 6 pages.

Center for Disease Control and Prevention (CDC) [online], "Covid Data Tracker," last updated Aug. 24, 2023, retrieved on Aug. 25, 2023, retrieved from URL <https://covid.cdc.gov/covid-data-tracker/#datatracker-home>, 5 pages.

Center for Disease Control and Prevention (CDC) [online], "People Who Are Immunocompromised," last updated May 11, 2023, retrieved from URL <https://www.cdc.gov/coronavirus/2019-ncov/need-extra-precautions/people-who-are-immunocompromised.html>, 4 pages.

Center for Disease Control and Prevention (CDC) [online], "SARS-CoV-2 variant classifications and definitions," last updated Mar. 20, 2023, retrieved on Aug. 25, 2023, retrieved from URL :<https://www.cdc.gov/coronavirus/2019-ncov/variants/variant-classifications.html>, 6 pages.

Chang et al., "Critical Care Management of a Severe Acute Respiratory Distress Syndrome Covid-19 Patient With Control Cesarean Section," Cureus, Feb. 2022, 14(2): 4 pages.

Chapman et al., "RSV604, a Novel Inhibitor of Respiratory Syncytial Virus Replication," Antimicrobial Agents and Chemotherapy, 2007, 51(9): 3346-3353.

Charytan et al., "Decreasing Incidence of Acute Kidney Injury in Patients with Covid-19 Critical Illness in New York City," Kidney International Reports, Apr. 2021, 6(4):916-27.

Chinen et al., "Critical respiratory failure in pregnancy complicated with Covid-19: A case report," Case Reports in Women's Health, Apr. 2021, 30: 4 pages.

Cho et al., "Discovery of the First C-Nucleoside HCV Polymerase Inhibitor (GS-6620) with Demonstrated Antiviral Response in HCV Infected Patients," J. Med. Chem., 2014, 57(5): 1812-1825.

Cho et al., "Synthesis and antiviral Activity of a Series of 1'-Substituted 4-aza-7,9-dideazaadenosine C-Nucleosides", Bioorganic & Medicinal Chemistry Letters, 2012, 22(8):2705-2707.

Choe et al., "Exploration for the effect of renal function and renal replacement therapy on pharmacokinetics of remdesivir and GS-441524 in patients with Covid-19: A limited case series," Clinical and Translational Science, Nov. 20, 2021, 15(3):732-740.

Choi et al., "Clinical Presentation and Outcomes of Middle East Respiratory Syndrome in the Republic of Korea," Infection & Chemotherapy, Jun. 2016, 48(2): 118-26.

Chokkalingam et al., "Association of Remdesivir Treatment With Mortality Among Hospitalized Adults With Covid-19 in the United States," JAMA Network Open, Dec. 2022, 5(12), 12 pages.

Cihlar et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 2008, 52(2): 655-665.

Cihlar et al., "Journey of Remdesivir From the Inhibition of Hepatitis C virus to the Treatment of Covid-19," Antiviral Therapy, Mar. 2022, 27(2), 12 pages.

Clark et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 2005, 48(17): 5504-5508.

Clarke et al., "Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases." Bioorganic & Medicinal Chemistry Letters, Apr. 29, 2015, 25: 2484-2487.

ClinicalTrials.gov [online], "Study of Obeldesivir in Nonhospitalized Participants With Covid-19 (Oaktree)," NCT05715528, last updated Oct. 19, 2023, retrieved on Oct. 19, 2023, retrieved from URL<https://clinicaltrials.gov/study/NCT05715528?term=NCT05715528&rank=1>, 13 pages.

ClinicalTrials.gov [online], "Study of Obeldesivir in Participants With Covid-19 Who Have a High Risk of Developing Serious or Severe Illness (Birch)," Gilead Sciences, Trial Identifier: NCT05603143, last updated Aug. 3, 2023, retrieved on Aug. 23, 2023, retrieved from URL: <https://classic.clinicaltrials.gov/ct2/show/record/NCT05603143>, 8 pages.

Coffin et al., "Persistent Marburg Virus Infection in the Testes of Nonhuman Primate Survivors," Cell Host & Microbe, Sep. 2018, 24(1): 405-416.

Colacino et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 2003, 22(11): 2013-2026.

Complexity Science Hub Vienna [online], "SARS-ANI VIS: A Global Open Access Dataset of Reported SARS-CoV-2 Events in Animals," last updated Jul. 12, 2023, retrieved on Aug. 29, 2023, retrieved from URL: <https://vis.csh.ac.at/sars-ani/#variants>, 2 pages.

Coppock et al., "Covid-19 treatment combinations and associations with mortality in a large multi-site healthcare system," PloS one, Jun. 11, 2021, 16(6): 13 pages.

Cox et al., "Oral prodrug of remdesivir parent GS-441524 is efficacious against SARS-CoV-2 in ferrets," Nature Communications, Nov. 2021, 12(1):1-11.

Cox et al., "Therapeutically administered ribonucleoside analogue MK-4482/EIDD-2801 blocks SARS-CoV-2 transmission in ferrets," Nature Microbiology, 2020, 6(1): 11-18.

Cross et al., Combination therapy protects macaques against advanced Marburg virus disease. Nature Communications, Mar. 2021, 12(1): 1891, 10 pages.

Cross et al., "Combination therapy with remdesivir and monoclonal antibodies protects nonhuman primates against advanced Sudan virus disease," JCI Insight, May 2022, 7(10): 1-14.

Cross et al., "Natural history of nonhuman primates after conjunctival exposure to Ebola virus," Scientific Reports, Mar. 2023, 13(1), 12 pages.

Dai et al., "Synthesis of 2'-C-β-Fluoromethyluridine," Organic Letters, 2003, 5(6): 807-810.

Damont et al., "Synthesis of 1'-C-Fluoromethyladenosine," Nucleosides, Nucleotides, and Nucleic Acids, 2007, 26:1431-1434.

Dande et al., "Remdesivir in a pregnant patient with Covid-19 pneumonia," Journal of Community Hospital Internal Medicine Perspectives, Jan. 2021, 11(1): 103-6.

Davis et al., "Dose Optimization of Obeldesivir for Covid-19 Treatment in Patients With Renal Impairment Using Population Pharmacokinetic Modeling," Presented at the Fourteenth American Conference on Pharmacometrics (ACoP14), Nov. 5-8, 2023, National Harbor, MD, USA, 1 page.

Davis et al., "Long Covid: major findings, mechanisms and recommendations," Nature Reviews Microbiology, Jan. 13, 2023, 21(3): 133-146.

De Clercq, "Antiviral Drugs: Current State of the Art," J. Clin. Virol., 2001, 22(1): 73-89.

De Clercq, "Molecular Targets for Antiviral Agents," The Journal of Pharmacology and Experimental Therapeutics, 2001, 297(1): 1-10.

De Francesco et al., "Approaching a New Era for Hepatitis C Virus Therapy: Inhibitors of the NS3-4A Serine Protease and the NS5B RNA-Dependent RNA Polymerase," Antiviral Research, 2003, 58(1): 1-16.

De Las Heras, "Synthesis of Ribosyl and Arabinosyl Cyanides by Reaction of 1-O-Acyl Sugars with Trimethylsilyl Cyanide," Journal of the Chemical Society, Perkin Transactions 1, 1982, pp. 903-907.

De Lombaert et al., "N-Phosphonomethyl Dipeptides and Their Phosphonate Prodrugs, a New Generation of Neutral Endopeptidase (NEP, EC 3,4.24.11) Inhibitors," J. Med. Chem., 1994, 37(4): 498-511.

(56) References Cited

OTHER PUBLICATIONS

De Wit et al., "Prophylactic and Therapeutic Remdesivir (GS-5734) Treatment in the Rhesus Macaque Model of MERS-CoV Infection," Proceedings of the National Academy of Sciences of the United States of America, Mar. 2020, 117(12): 6771-6776.

De Wit et al., "SARS and MERS: Recent Insights Into Emerging Coronaviruses," Nature Review, Jun. 2016; 14: 523-34.

Dehghan et al., "A Lesson for the Future; Determining the Prognosis of the Pregnant Patients with Covid-19 in the Second Trimester? A Case Report," Caspian Journal of Internal Medicine, Apr. 2022, 13(Suppl 3): 284-288.

Dewolf et al., "SARS-CoV-2 in immunocompromised individuals," Immunity, Oct. 11, 2022; 55(10): 1779-98.

Di Bisceglie et al., "The Unmet Challenges of Hepatitis C," Scientific American, Oct. 1999, pp. 80-85.

Dinnon et al., "A mouse-adapted model of SARS-CoV-2 to test Covid-19 countermeasures," Nature, Aug. 2020, 586: 560-566.

Dolzhenko et al., "Pyrazolo[1,5-a][1,3,5]Triazines(5-Aza-9-Deazapurines): Synthesis and Biological Activity," Heterocycles, 2008, 75(7): 1575-1622.

Domingo et al., "The quasispecies (extremely heterogeneous) nature of viral RNA genome populations: biological relevance—a review," Gene, 1985, 40: 1-8.

Dondoni et al., "Thiazole-Based Synthesis of Formyl C-Glycosides," Journal of Organic Chemistry, 1994, 59: 6404-6414.

Douafer et al., "Scope and limitations on aerosol drug delivery for the treatment of infectious respiratory diseases," Journal of Controlled Release, Sep. 2020, 325: 276-292.

Dudfield et al., "Synthesis of C-ribosyl imidazo[2,1-f][1,2,4]triazines as inhibitors of adenosine and AMP deaminases," J. Chem. Soc, Perkin Trans I, 1999, pp. 2929-2936.

Dudfield et al., "Synthesis of C-ribosyl 1,2,4-triazolo[3,4-f][1,2,4]triazines as Inhibitors of Adenosine and AMP Deaminasses," J. Chem. Soc., Perkin Trans. 1, 1999, pp. 2937-2942.

Durcan et al., "Hydroxychloroquine Blood Levels in Systemic Lupus Erythematosus: Clarifying Dosing Controversies and Improving Adherence", Journal of Rheumatology, 2015, 42(11):2092-2097.

Dymock et al., "Novel approaches to the treatment of hepatitis C virus infection," Antiviral Chemistry & Chemotherapy, 2000, 11(2): 79-96.

Easterlin et al., "Extremely Preterm Infant Born to a Mother With Severe Covid-19 Pneumonia," Journal of Investigative Medicine High Impact Case Reports, Jul. 2020, 8: 1-5.

Eastman et al., "Remdesivir: A Review of Its Discovery and Development Leading to Emergency Use Authorization for Treatment of Covid-19," ACS Central Science May 4, 2020; 6(5): 672-83.

Eid et al., "Early Administration of Remdesivir and Intensive Care Unit Admission in Hospitalized Pregnant Individuals With Coronavirus Disease 2019 (Covid-19)," Obstetrics & Gynecology, Apr. 2022, 139(4): 619-621.

El Safadi et al., "5-Modified-2'-dU and 2'-dC as Mutagenic Anti HIV-1 Proliferation Agents: Synthesis and Activity," Journal of Medicinal Chemistry, 2010, 53(4): 1534-1545.

ERA-EDTA Council et al., "Chronic kidney disease is a key risk factor for severe Covid-19: a call to action by the ERA-EDTA," Nephrology Dialysis Transplantation, Jan. 2021, 36(1): 87-94.

Escaffre et al., "STAT-1 Knockout Mice as a Model for Wild-Type Sudan Virus (SUDV)," Viruses, Jul. 2021, 13(7): 1-16.

European Centre for Disease Prevention and Control (ECDC) [online], "SARS-CoV-2 variants of concern as of Aug. 24, 2023," last updated Aug. 24, 2023, retrieved on Aug. 29, 2023, retrieved from URL: < https://www.ecdc.europa.eu/en/covid-19/variants-concern>, 18 pages.

European Medicines Agency, "New vaccine for prevention of Ebola virus disease recommended for approval in the European Union," Press Release, May 29, 2020, 3 pages.

European Medicines Agency, "Summary on compassionate use: Remdesivir Gilead," Procedure No. EMEA/H/K/005622/CU, Apr. 3, 2020, 45 pages.

Fan et al., "Safety profile of the antiviral drug remdesivir: An update," Biomedicine & Pharmacotherapy, Oct. 2020, 130: 3 pages.

Farquhar et al., "Biologically Reversible Phosphate-Protective Groups," Journal of Pharmaceutical Sciences, 1983, 72(3): 324-325.

Fauquet et al., "Abbreviations for vertebrate virus species names", Archives of Virology, Dec. 31, 1999, pp. 1865-1880.

fda.gov [online], "Remdesivir by Gilead Sciences: FDA Warns of Newly Discovered Potential Drug Interaction That May Reduce Effectiveness of Treatment," Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce>, 2 pages.

Feldmann et al., "Chapter 32: Filoviridae: Marburg and Ebola Viruses," in Fields Virology, Sixth Edition, May 2013, 1: 36 pages.

Feldmann et al., "Ebola," New England Journal of Medicine, May 2020, 382: 1832-42.

Flint et al., "Functional analysis of cell surface-expressed hepatitis C virus E2 glycoprotein," J. Virol., Aug. 1999, 73(8): 6782-6790.

Flythe et al., "Characteristics and Outcomes of Individuals With Pre-existing Kidney Disease and Covid-19 Admitted to Intensive Care Units in the United States," American Journal of Kidney Diseases, Feb. 2021, 77(2): 190-203.

Food and Drug Administration (FDA), "Estimating the Maximum Safe Starting Dose in Initial Clinical Trials for Therapeutics in Adult Healthy Volunteers," Jul. 2005, 30 pages.

Food and Drug Administration (FDA), "Fact Sheet for Healthcare Providers: Emergency Use Authorization for Lagevrio™ (molnupiravir) Capsules," FDA Emergency Use Authorization, published Dec. 2021, 21 pages.

Food and Drug Administration (FDA), "Fact Sheet for Healthcare Providers: Emergency Use Authorization for Paxlovid," FDA Emergency Use Authorization, published Dec. 2021, revised Feb. 2023, 36 pages.

Food and Drug Administration (FDA), "Highlights of Prescribing Information for Paxlovid™," revised May 2023, 51 pages.

Foster et al., "Deuterium isotope effects in studies of drug metabolism," Trends in Pharmacological Sciences, Jan. 1984, 5:524-527.

Franchetti et al., "Antitumor Activity of C-Methyl-β-D-ribofuranosyladenine Nuceoside Ribonuceotide Reductase Inhibitors," J. Med. Chem. 2005, 48: 4983-4989.

Freeman et al., "3 Prodrug Design for Phosphates and Phosphonates," Progress in Medicinal Chemistry, 1997, 34: 111-147.

Fukumoto et al., "Viral Dynamics of Hepatitis C Early After Orthotopic Liver Transplantation: Evidence for Rapid Turnover of Serum Virions," Hepatology, 1996, 24: 1351-1354.

Fuse, "Organic Synthesis Using Microflow Reactor," Journal of Synthetic Organic Chemistry Japan, 2012, 70(2): 177-178 (with English abstract).

Garcia et al., "Synthesis of (2,3,4,6-tetra-O-acetyl-alpha-D-glycopyranosyl)thiophene derivatives as new C-nucleoside analogues," J. Carbohydrate Chemistry, 2001, 20(7/8): 681-687.

Gardelli et al., "Phosphoramidate Prodrugs of 2'-C-Methylcytidine for Therapy of Hepatitis C Virus Infection," Journal of Medicinal Chemistry, 2009, 52(17): 5394-5407.

Garnett et al., "Scientific white paper on concentration-QTc modeling," J. Pharmacokinet Pharmacodyn., Jun. 2018, 45(3):383-397.

Geisbert et al., "Considerations in the Use of Nonhuman Primate Models of Ebola Virus and Marburg Virus Infection," The Journal of Infectious Diseases, Oct. 2015, 212(Suppl. 2), S91-97.

Geisbert et al., "Single-injection vaccine protects nonhuman primates against infection with marburg virus and three species of ebola virus," Journal of Virology, Jul. 2009, 83(14): 7296-7304.

George et al., "Preparation of silyl-and germylmetallic compounds," Journal of the American Chemical Society, Jan. 1960, 82(2):403-6.

Gil et al., "Covid-19; Drug Targets and Potential Treatments," Journal of Medicinal Chemistry, Jun. 2020, 63(21): 12359-12386.

Gilead Sciences, Inc., "Veklury 100 mg powder for concentrate for solution for infusion," Package Leaflet, last revised Jun. 2023, 12 pages.

(56) References Cited

OTHER PUBLICATIONS

Gilead Sciences, Inc., "Veklury® (remdesivir) Full Prescribing Information" last revised Jul. 2023, 44 pages.
Gleeson et al., "Prediction of the Potency of Inhibitors of Adenosine Deaminase by QM/MM Calculations," Chem. Commun., 2003, pp. 2180-2181.
Goldman et al., "Covid-19 in immunocompromised populations: implications for prognosis and repurposing of immunotherapies," Journal for Immunotherapy of Cancer, Jun. 11, 2021, 9(6): 1-13.
Goldman et al., "Remdesivir for 5 or 10 Days in Patients with Severe Covid-19," New England Journal of Medicine, May 2020, 383(19), 1827-37.
Gordon et al., "Control of Hepatitis C: A Medicinal Chemistry Perspective," J. Med. Chem., 2005, pp. 1-20, vol. 48, No. 1.
Gordon et al., "Efficient Incorporation and Template-Dependent Polymerase Inhibition are Major Determinants for the Broad-Spectrum Antiviral Activity of Remdesivir," Journal of Biological Chemistry, Dec. 2021, 298(2): 14 pages.
Gordon et al., "Remdesivir is a direct-acting antiviral that inhibits RNA-dependent RNA polymerase from severe acute respiratory syndrome coronavirus 2 with high potency," J. Biol. Chem., 2020, 295(20):6785-6797.
Gordon et al., "The antiviral compound remdesivir potently inhibits RNA-dependent RNA polymerase from Middle East respiratory syndrome coronavirus," Journal of Biol. Chemistry, 2020, 295(15):4773-4779.
Gottlieb et al., "Early Remdesivir to Prevent Progression to Severe Covid-19 in Outpatients," New England Journal of Medicine, Jan. 27, 2022, 386(4): 305-315.
Greene et al., "Protective Groups in Organic Synthesis," John Wiley & Sons., 1991, pp. 118-142.
Greene et al., "Protective Groups in Organic Synthesis," published by John Wiley & Sons, v Inc., 1991, pp. 1-4, 10-14, 47-53 and 100-103.
Grein et al., "Compassionate Use of Remdesivir for Patients with Severe Covid-19" The New England Journal of Medicine, Apr. 2020, 382(24): 2327-2336.
Gudmundsson et al., "Synthesis of imidazo[1,2-a]pyridine C-Nucleosides with an Unexpected Site of Ribosylation," Journal of Organic Chemistry, 1997, 62: 3453-3459.
Gudmundsson et al., "The Condensation of 2,6-dichloroimidazo[1,2-a]pyridine C-nucleoside with an Unexpected Site of Ribosylation," Tetrahedron Letters, 1996, 7(14): 2365-2368.
Gunic et al., "Cyclic monophosphate prodrugs of base-modified 2'-C-methyl ribonucleosides as potent inhibitors of hepatitis C virus RNA replication," Bioorganic & Medicinal Chemistry Letters, 2007, 17: 2452-2455.
Gupta et al., "Factors Associated With Death in Critically Ill Patients With Coronavirus Disease 2019 in the US," JAMA Internal Medicine, Nov. 2020, 180(11): 1436-47.
Gutierrez et al., "Remdesivir use in pregnancy during the SARS-CoV-2 pandemic," The Journal of Maternal-Fetal & Neonatal Medicine, Feb. 2022, 35(25): 9445-51.
Hadi et al., "Outcomes of Covid-19 in Solid Organ Transplant Recipients: A Propensity-matched Analysis of a Large Research Network," Transplantation, Jun. 1, 2021; 105(6): 1365-71.
Hamann et al., "Synthesis and antiviral evaluation of 7,9-dideaza-8-thiapurine C-nucleoside derivatives," Collection Symposium Series, 2008, 10: 347-349.
Hamann et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 2009, 17: 2321-2326.
Hammond et al. "Oral Nirmatrelvir for High-Risk, Nonhospitalized Adults with Covid-19," New England Journal of Medicine, Feb. 2022, 386(15): 1397-1408.
Han et al., "Genetic, antigenic and pathogenic characterization of avian coronaviruses isolated from pheasants (*Phasianus colchicus*) in China," Veterinary Microbiology, Nov. 2019, 240: 1-14.
Han et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 1992, 22(19): 2815-2822.
Hanson et al., "Estimated Global Proportions of Individuals With Persistent Fatigue, Cognitive, and Respiratory Symptom Clusters Following Symptomatic Covid-19 in 2020 and 2021," JAMA Network, Oct. 10, 2022; 328(16): 1604-1615.
Haraguchi et al., "Stereoselective Synthesis of 1-40 -C-Branched Uracil Nucleosides From Uridine," Nucleosides & Nucleotides, 1995, 14(3-5): 417-420.
Harbeson et al., "Deuterium in Drug Discovery and Development," Annual Reports in Medicinal Chemistry, Dec. 31, 2011, 46:403-417.
Harcourt et al., "Molecular Characterization of the Polymerase Gene and Genomic Termini of Nipah Virus," Virology, 2001, 287: 192-201.
Harki et al., "Synthesis and Antiviral Activity of 5-Substituted Cytidine Analogues: Identification of Potent Inhibitor of Viral RNA-Dependent RNA Polymerases," Journal of Medicinal Chemistry, 2006, 49(21): 6166-6169.
Harvey et al., "Association of SARS-CoV-2 Seropositive Antibody Test With Risk of Future Infection," JAMA Internal Medicine, Feb. 24, 2021; 181(5): 672-679.
Hayashi et al., "C-Nucleosides, a Synthesis of 2-Substituted 7-(b-D-Ribofuranosyl)-Pyrrolo[2,1-f]-1,2,4-Triazines. A New Type of "Purine Like" C-Nucleoside," Heterocycles, 1992, 34(3): 569-574.
Hayashi et al., "Gasless laparoendoscopic single-site surgery for management of unruptured tubal pregnancy in a woman with moderate Covid-19 pneumonia after administration of remdesivir and casirivimab-imdevimab: A case report," Case Reports in Women's Health, Jan. 2022, 33: e00368.
He et al., Species Differences in Size Discrimination in the Paracellular Pathway Reflected by Oral Bioavailability of Poly(ethylene glycol) and D-peptides, Journal of Pharmaceutical Sciences, May 1998, 87(5): 626-633.
Hecker et al., "Liver Targeted Prodrugs of 2'-C-Methyladenosine for Therapy of Hepatitis C Virus Infection," J. Med. Chem., 2007, 50(16): 3891-3896.
Henry et al., "Chronic kidney disease is associated with severe coronavirus disease 2019 (Covid-19) infection," International urology and nephrology, Jun. 2020 52(6): 1193-4.
Herbert et al., "Development of an antibody cocktail for treatment of Sudan virus infection," Proceedings of the National Academy of Sciences, Feb. 2020, 117: 3768-78.
Higgs et al., "Prevail IV: A Randomized, Double-Blind, 2-Phase, Phase 2 Trial of Remdesivir vs Placebo for Reduction of Ebola Virus RNA in the Semen of Male Survivors," Clinical Infectious Diseases, Nov. 2021, 73(10): 1849-1856.
Hoffmann et al., "When, in the context of drug design, can a fluorine atom successfully substitute a hydroxyl group?," International Journal of Quantum Chemistry, 2002, 89: 419-427.
Holshue et al., "First Case of 2019 Novel Coronavirus in the United States", The New England Journal of Medicine, Jan. 2020, 9 pages.
Hop et al., "Plasma-pooling methods to increase throughput for in vivo pharmacokinetic screening," Journal of Pharmaceutical Sciences, Jul. 1998, 87(7):901-903.
Hoste et al., "Assessment of renal function in recently admitted critically ill patients with normal serum creatinine," Nephrology Dialysis Transplantation, Apr. 2005, 20(4): 747-53.
Hsu et al., Covid-19 Among US Dialysis Patients: Risk Factors and Outcomes From a National Dialysis Provider, American Journal of Kidney Disease, May 2021, 77(5):748-56.
Huang et al., "Recent development of therapeutics for chronic HCV infection," Antiviral Research, Sep. 2006, 71(2-3): 351-362.
Humeniuk et al., "Pharmacokinetic, Pharmacodynamic, and Drug-Interaction Profile of Remdesivir, a SARS-CoV-2 Replication Inhibitor," Clinical pharmacokinetics, May 2021, 60(2021): 569-583.
Igbinosa et al., "Use of remdesivir for pregnant patients with severe novel coronavirus disease 2019," American Journal of Obstetrics & Gynecology, Aug. 2020, 223(5): 768-770.

(56) References Cited

OTHER PUBLICATIONS

Ioannou et al., "Rates and Factors Associated With Documentation of Diagnostic Codes for Long Covid in the National Veterans Affairs Health Care System," JAMA Network Open, Jul. 29, 2022, 5(7): 1-11.

Itoh et al.,"Divergent and Stereocontrolled Approach to the Synthesis of Uracil Nucleosides Branched at the Anomeric Position," J. Org. Chem, 1995, 60: 656-662.

Jacobson et al., "Use of dexamethasone, remdesivir, convalescent plasma and prone positioning in the treatment of severe Covid-19 infection in pregnancy: A case report," Case Reports in Women's Health, Jan. 2021, 29: 3 pages.

Jasko et al., "5'-Phosphonates of Ribonucleosides and 2'-Deoxyribonucleosides: Synthesis and Antiviral Activity," Nucleosides & Nucleotides, 1993, 12(8): 879-893.

Jeong et al., "Detecting drug-drug interactions between therapies for Covid-19 and concomitant medications through the FDA adverse event reporting system," Frontiers in Pharmacology, Jul. 22, 2022, 13: 14 pages.

Jonckers et al., "2'Deoxy-2'-spirocyclopropylcytidine Revisited: A New and Selective Inhibitor of the Hepatitis C Virus NS5B Polymerase," Journal of Medicinal Chemistry, Nov. 2010, 53(22)8150-60.

Jones et al., "Di- and Triester Prodrugs of the Varicella-Zoster Antiviral Agent 6-Methoxypurine Arabinoside," Journal of Medicinal Chemistry, Jan. 1992, 35(1):56-63.

Jorgensen et al., "A review of remdesivir for Covid-19 in pregnancy and lactation," Journal of Antimicrobial Chemotherapy, Aug. 2021, 77(1): 24-30.

Joseph [online], "As the coronavirus spreads, a drug that once raised the world's hopes is given a second shot," StatNews.com, retrieved on Mar. 13, 2023, URL <https://www.statnews.com/2020/03/16/remdesivir-surges-ahead-against-coronavirus>, Mar. 16, 2020, 11 pages.

Julander et al., "Remdesivir efficacy against yellow fever in a hamster model," Antiviral Research, Jul. 2022, 203:105331.

Kabat et al., "Nucleosides, CXLVIII, Synthesis of 6-(β-D-Ribofuranosyl)picolinamide: A Novel C-Nucleoside from D-Ribonolactone" Chemical & Pharmaceutical Bulletin, 1988, pp. 634-640, vol. 36, No. 2.

Kabinger et al., "Mechanism of Molnupiravir-Induced SARS-CoV-2 Mutagenesis," Nature Structural & Molecular Biology, Aug. 2021, 28(9): 740-746.

Kaewkhao et al., "High sensitivity methods to quantify chloroquine and its metabolite in human blood samples using LC-MS/MS", Bioanalysis, Mar. 2019, 11(5):333-347.

Kalil et al., "Baricitinib plus Remdesivir for hospitalized adults with Covid-19," New England Journal of Medicine, Dec. 11, 2020, 13 pages.

Kelly et al., "Post-acute sequelae of SARS-CoV-2 among previously hospitalised individuals with Covid-19: a systematic literature review and meta-analysis," European Respiratory Journal, 2022, 60(Suppl. 66): 4430.

Khamnei et al., "Neighboring Group Catalysis in the Design of Nucleotide Prodrugs," J. Med. Chem., 1996, 39(20): 4109-4115.

Khan et al., "Coronaviruses disease 2019 (Covid-19): Causative agent, mental health concerns, and potential management options," Journal of Infection and Public Health, Dec. 2020, 13(12):1840-1844.

Khbou et al., "Coronaviruses in farm animals: Epidemiology and public health implications," Veterinary Medicine and Science, Sep. 2020, 7(2): 322-347.

Kim et al., "Detection of bovine coronavirus in nasal swab of non-captive wild water deer, Korea," Transboundary and Emerging Diseases, Mar. 2018, 65(3): 627-631.

Kim et al., "Reversal of the Progression of Fatal Coronavirus Infection in Cats by a Broad-Spectrum Coronavirus Protease Inhibitor," PLOS Pathogens, Mar. 30, 2016, 18 pages.

Kim et al., "Synthesis and Evaluation of 2-Amino-6-fluoro-9-(4-hydroxy-3-hydroxymethylbut-1-yl) purine Mono-and Diesters as Potential Prodrugs of Penciclovir," Bioorganic & Medicinal Chemistry, Mar. 1999, 7(3):565-70.

Kim et al., "Synthesis and Evaluation of 2-Amino-9-(1,3-dihydroxy-2-propoxymethyl)-6-fluoropurine Mono-and Diesters as Potential Prodrugs of Ganciclovir," Journal of Medicinal Chemistry, Jan. 1999, 42(2):324-28.

Klumpp et al., "Chapter 20: Discovery and Clinical Evaluation of the Nucleoside Analog Balapiravir (R1626) for the Treatment of HCV Infection," Antiviral Drugs: From Basic Discovery through Clinical Trials, Jun. 20, 2011, pp. 287-304.

Klumpp et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistry, 2006, 281(7): 3793-3799.

Knaggs et al., A QSAR Study Investigating the Effect of L-Alanine Ester Variation on the Anti-HIV Activity of Some Phosphoramidate Derivatives of d4T, Bioorganic & Medicinal Chemistry Letters, 2000, 10: 2075-2078.

Knutsen et al., "Synthesis of Imidazo-fused Bridgehead-nitrogen C-Nucleosides : Coupling-Elimination Reactions of 2,5-Anhydro-3,4,6-tri-O-benzoyl-D-allonic Acid," J. Chem. Soc. Perkin Trans I, 1985, pp. 621-630.

Knutsen et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc. Perkin Trans I, 1984, pp. 229-238.

Kobe et al., "Use of Distance Geometry Approach for the In Vitro Antiviral Activity Evaluation of N-bridgehead C-nucleosides," European J. Med. Chem., 1992, 27(3): 259-266.

Koplon [online], "$37.5 million grant will address research of high-priority infections," UAB News, retrieved on Mar. 13, 2023, URL <https://www.uab.edu/news/health/item/10307-37-5-million-grant-will-address-research-of-high-priority-infections>, Mar. 20, 2019, 1 page.

Ksiazek et al., "A Novel Coronavirus Associated with Severe Acute Respiratory Syndrome," New England Journal of Medicine, May 2003, 348(20): 1953-66.

Kuang et al., "Reversion of Ebolavirus Disease from a Single Intramuscular Injection of a Pan-Ebolavirus Immunotherapeutic;" Pathogens, Jun. 2022, 11(6): 655, 14 pages.

Kudose et al., "Longitudinal Outcomes of Covid-19-Associated Collapsing Glomerulopathy and Other Podocytopathies," Journal of the American Society of Nephrology, Nov. 2021; 32(11): 2958-69.

Kulli, "K Banhatti Polynomials of Remdesivir, Chloroquine, Hydroxychloroquine: Research Advances for the Prevention and Treatment of Covid-19," SSRG International Journal of Applied Chemistry, May-Aug. 2020, 7(2):48-55.

Kushner et al., "Pharmacological uses and perspectives of heavy water and deuterated compounds," Canadian Journal of Physiology and Pharmacology, Feb. 1999, 77(2):79-88.

Kuzik et al., "Nebulized Hypertonic Saline in the Treatment of Viral Bronchiolitis in Infants", The Journal of Pediatrics, Sep. 2007, 151(3):266-270.el.

Lafont et al., "Targeted SARS-CoV-2 treatment is associated with decreased mortality in immunocompromised patients with Covid-19," Journal of Antimicrobial Chemotherapy, Jul. 25, 2022, 77(10): 2688-92.

Languon et al., "Filovirus Disease Outbreaks: A Chronological Overview," Virology: Research and Treatment, Jun. 2019, 10: 1-12.

Lat et al., "Therapeutic options in the treatment of severe acute respiratory syndrome coronavirus 2 in pregnant patient," American Journal of Obstetrics & Gynecology MFM, Nov. 2020, 2(4): 100224.

Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 1995, 38(20): 3941-3950.

Lefebvre et al., "Synthesis, Decomposition Pathways and 'In Vitro' Evaluation of Bioreversible Phosphotriesters of Azt, Nucleosides," Nucleotides & Nucleic Acids, 1995, 14(3-5): 763-766.

(56) References Cited

OTHER PUBLICATIONS

Levey et al., "Using standardized serum creatinine values in the modification of diet in renal disease study equation for estimating glomerular filtration rate," Annals of Internal Medicine, Aug. 15, 2006, 145(4):247-254.
Leyssen et al., "Molecular strategies to inhibit the replication of RNA Viruses." Antiviral Research, 2008, 78:9-25.
Li et al., "Key Metabolic Enzymes Involved in Remdesivir Activation in Human Lung Cells," Antimicrobial Chemotherapy, Aug. 2021, 65(9): 17 pages.
Li et al., "Remdesivir Metabolite GS-441524 Effectively Inhibits SARS-CoV-2 Infection in Mouse Models," Journal of Medicinal Chemistry, Feb. 2021, 65(4): 2785-2793.
Lim et al., "Pregnancy and Severe ARDS with Covid-19: Epidemiology, Diagnosis, Outcomes and Treatment," Seminars in Fetal and Neonatal Medicine, Feb. 2023; 28(1): 12 pages.
Lin et al., "Animal Coronavirus Diseases: Parallels with Covid-19 in Humans," Viruses, Jul. 2021, 13(8): 1-15.
Lindell et al., "Synthesis and Biochemical Testing of 3-(Carboxyphenylethyl)imidazo[2,1-f][1,2,4]triazines as Inhibitors of AMP Deaminase," ACS Medicinal Chemistry Letters, 2010, 1(6): 286-289.
Liu et al., "Ebola virus persistence and disease recrudescence in the brains of antibody-treated nonhuman primate survivors," Science Translational Medicine, Feb. 2022, 14(631), 13 pages.
Liu et al., "Hydroxychloroquine, a less toxic derivative of chloroquine, is effective in inhibiting SARS-CoV-2 infection in vitro," Cell Discovery, Mar. 18, 2020, 6:16, 4 pages.
Liu et al., "Physiologically-based pharmacokinetic modeling of remdesivir and its metabolites in pregnant women with Covid-19," CPT: Pharmacometrics & Systems Pharmacology, Dec. 2022, 12(2): 148-53.
Lo et al., "Remdesivir (GS-5734) protects African green monkeys from Nipah virus challenge," Science Translational Medicine, May 29, 2019, 11(494):1-6.
Lo et al., "GS-5734 and its parent nucleoside analog inhibit Filo-, Pneumo-, and Paramyxoviruses," Scientific Reports, 2017, 7(43395):1-7.
Lovelette, "1,2,4-Triazines. Synthesis of selected members of the s-triazolo[3,4-f][1,2,4]triazine and tetrazolo[1,5-f][1,2,4]triazine ring systems," Journal of Heterocyclic Chemistry, 1979, 16: 555-560.
Lu, Chengping, Veterinary Microbiology 5th edition, Jan. 31, 2013, p. 431, China Agriculture Press (No English Translation available).
MacKenna et al., "Risk of severe Covid-19 outcomes associated with immune-mediated inflammatory diseases and immune-modifying therapies: a nationwide cohort study in the OpenSafely platform," The Lancet Rheumatology, Jun. 8, 2022, 4(7): e490-e506.
Mackman et al., "Chapter 22: Veklury® (Remdesivir), a Nucleotide Prodrug Approved for the treatment of Covid-19," 2022 Medicinal Chemistry Reviews, Dec. 2022, 57: 545-569.
Mackman et al., "Discovery of GS-5245 (Obeldesivir), an Oral Prodrug of Nucleoside GS-441524 that Exhibits Antiviral Efficacy in SARS-CoV-2 Infected African Green Monkeys," BioRxiv, Apr. 28, 2023, 50 pages.
Mackman et al., "Prodrugs of a 1'-CN-4-Aza-7,9-dideazaadenosine C-Nucleoside Leading to the Discovery of Remdesivir (GS-5734) as a Potent Inhibitor of Respiratory Syncytial Virus with Efficacy in the African Green Monkey Model of RSV," Journal of Medicinal Chemistry, Apr. 2021, 64(8): 5001-5017.
Maldarelli et al., "Remdesivir Treatment for Severe Covid-19 in Third-Trimester Pregnancy: Case Report and Management Discussion," Open Forum Infectious Diseases, Sep. 2020, 7(9): 4 pages.
Malin et al., "Remdesivir against Covid-19 and Other Viral Diseases," Clinical Microbiology Reviews, Oct. 14, 2020, 34(1):e00162-20.
Malone et al., "Structural basis for substrate selection by the SARS-CoV-2 replicase," Nature, Feb. 2023, 614(7949): 781-787.
Marikawa et al., "Remdesivir impairs mouse preimplantation embryo development at therapeutic concentrations," Reproductive Toxicology, Aug. 2022, 111: 135-47.
Markham, "REGN-EB3; First Approval," Drugs, Jan. 2021, 81: 175-178.
Martell et al., "Hepatitis C Virus (HCV) Circulates as a Population of Different but Closely Related Genomes: Quasispecies Nature of HCV Genome Distribution," Journal of Virology, 1992, 6695: 3225-3229.
Martin et al., "Genetic Conservation of SARS-CoV-2 RNA Replication Complex in Globally Circulating Isolates and Recently Emerged Variants from Humans and Minks Suggests Minimal Pre-Existing Resistance to Remdesivir," Antiviral Research, Apr. 2021, 188: 7 pages.
Martin et al., "Hint2, A Mitochondrial Apoptotic Sensitizer Down-Regulated in Hepatocellular Carcinoma," Gastroenterology, Jun. 2006, 130(7): 2179-2188.
Martinez et al., "Efficacy of the oral nucleoside prodrug GS-5245 (Obeldesivir) against SARS-CoV-2 and coronaviruses with pandemic potential," BioRxiv, Jun. 28, 2023, 54 pages.
Marzban-Rad et al., "The use of remdesivir among pregnant women and associated clinical outcomes in mother and the child," Annals of Medicine and Surgery, May 2022, 77: 3 pages.
Mason et al., "Polyadenylation-dependent screening assay for respiratory syncytial virus RNA transcriptase activity and identification of an inhibitor," Nucleic Acids Research, 2004, 32(16): 4758-4767.
Matulic-Adamic et al., "Synthesis of 3-(β-D-Ribofuranosyl)-2-Fluoropyridine and 3-(β-D-Ribofuranosyl)-Pyridin-2-one," Tetrahedron Letters, 1997, 38(2): 203-206.
Matulic-Adamic et al., "Synthesis of 5-(β-D-Ribofuranosyl)-Pyridin-2-one: a 'Deletion-Modified' Analogue of Uridine," Tetrahedron Letters, 1997, 38(10): 1669-1672.
McCoy et al., "Compassionate use of remdesivir for treatment of severe coronavirus disease 2019 in pregnant women at a United States academic center," American Journal of Obstetrics & Gynecology MFM, Aug. 2020, 2(Suppl 3): 4 pages.
McGuigan et al. "Application of Phosphoramidate ProTide Technology Significantly Improves Antiviral Potency of Carbocyclic Adenosine Derivatives," J. Med. Chem. 2006, 49: 7215-7226.
McGuigan et al., "Application of Phosphoramidate Pronucleotide Technology to Abacavir Leads to a Significant Enhancement of Antiviral Potency", J. Med. Chem. 2005, 48(10):3504-3515.
McGuigan et al., "Aryl Phosphoramidate Derivatives of d4T Have Improved Anti-HIV Efficacy in Tissue Culture and May Act by the Generation of a Novel Intracellular Metabolite," J. Med. Chem., 1996, 39: 1748-1753.
McGuigan et al., "Design, synthesis and biological evaluation of phosphorodiamidate prodrugs of antiviral and anticancer nucleosides," European Journal of Medical Chemistry, 2013, 70: 326-340.
McGuigan et al., "Intracellular Delivery of Bioactive AZT Nucleotides by Aryl Phosphate Derivatives of AZT," J. Med. Chem., 1993, 36(8): 1048-1052.
Mehellou et al., "Aryloxy Phosphoramidate Triesters: a Technology for Delivering Monophosphorylated Nucleosides and Sugars into Cells," ChemMedChem, 2009, 4:1779-1791.
Meppen et al., "Cyclic phosphoramidates as prodrugs of 2'-C-methylcytidine," European Journal of Medicinal Chemistry, 2009, 49(9): 3765-3770.
Meppen et al., "Medi-404—A Prodrug Approach for the Treatment of HCV Infection," Abstracts of papers, 236th ACS National Meeting, Philadelphia, PA, United States, Aug. 17-21, 2008, 1 page.
Metobo et al., "Practical synthesis of 1'-substituted Tubercidin C-nucleoside analogs," Tetrahedron Letters, Feb. 2012, 53(5):484-486.
Migliaccio et al., "Characterization of Resistance to Non-obligate Chain-terminating Ribonucleoside Analogs That Inhibit Hepatitis C Virus Replication in vitro," The Journal of Biological Chemistry, 2003, 278(49): 49164-49170.
Mitchell et al., "Bioreversible Protection for the Phospho Group; Bioactivation of the Di(4-acyloxybenzyl) and Mono(4-acyloxybenzyl) Phosphoesters of Methylphosphonate and Phosphonoacetate," J. Chem. Soc., Perkin Trans. 1, 1992, pp. 2345-2353.

(56) References Cited

OTHER PUBLICATIONS

Mitchell et al., "Synthesis of C-Nucleoside Isosteres of 9-(2-Hydroxyethoxymethyl)guanine (Acyclovir)," J. Het. Chem., 1984, 21(3): 697-699.

Moennig et al., "The Pestiviruses", Advances in Virus Research, 1992, 41: 53-98.

Moorman et al., "5'-ester prodrugs of the varicella-zoster antiviral agent, 6-methoxypurine arabinoside," Antiviral Chemistry & Chemotherapy, Jun. 1992, 3(3):141-46.

Moradpour et al., "Replication of hepatitis C virus," Nature Reviews Microbiology, 2007, 5(6): 453-463.

Morris, "Mechanisms of action and therapeutic role of corticosteroids in asthma", J. Allergy Clin Immunol., Jan. 1985, 75(1 Pt): 1-13.

Moscow et al., "Reduced Folate Carrier Gene (RFC1) Expression and Anti-Folate Resistance in Transfected and Non-Selected Cell Lines," International Journal of Cancer, 1997, 72:184-190.

Mossel et al., "Exogenous ACE2 expression allows refractory cell lines to support severe acute respiratory syndrome coronavirus replication," Journal of Virology, Mar. 15, 2005, 79(6): 3846-50.

MotherToBaby, "Remdesivir (Veklury®): Fact Sheet," Otis, May 2022, 4 pages.

Mozaffari et al., "Immunocompromised patients hospitalized for Covid-19 in the United States: evolving patient characteristics and clinical outcomes across emerging variants," Poster #LB081, Presented at European Congress of Clinical Microbiology and Infectious Diseases (ECCMID), Apr. 15-18, 2023, 1 page.

Mozaffari et al., "Remdesivir Treatment in Hospitalized Patients With Coronavirus Disease 2019 (Covid-19): A Comparative Analysis of In-hospital All-cause Mortality in a Large Multicenter Observational Cohort," Clinical Infectious Diseases, Jul. 2022, 75(1): e450-e458.

Mulangu et al., "A Randomized, Controlled Trial of Ebola Virus Disease Therapeutics," New England Journal of Medicine, Dec. 2019; 381(24): 2293-303.

Munster et al., "Hydroxychloroquine concentration-response relationships in patients with rheumatoid arthritis", Arthritis Rheumatology, Jun. 2002, 46(6): 1460-1469.

Murakami et al., "Mechanism of Activation of Beta-D-2'-Fluoro-2'-C-Methylcytidine and Inhibition of Hepatitis C Virus NS5B RNA Polymerase", Antimicrob Agents Chemother., Feb. 2007, 51(2):503-509.

Murakami et al., "Mechanism of Activation of PSI-7851 and Its Diastereoisomer PSI-7977". The Journal of Biological Chemistry, 2010, 285(45): 34337-34347.

Murphy et al., "The Nucleoside Analog GS-441524 Strongly Inhibits Feline Infectious Peritonisitis (FIP) Virus in Tissue Culture and Experimental Cat Infection Studies", Veterinary Microbiology, 2018, 219: 226-233.

Naqvi et al., "Tocilizumab and Remdesivir in a Pregnant Patient With Coronavirus Disease 2019 (Covid-19)," Obstetrics & Gynecology, Nov. 2020, 136(5): 1025-9.

Nasrallah et al., "Pharmacological treatment in pregnant women with moderate symptoms of coronavirus disease 2019 (Covid-19) pneumonia," The Journal of Maternal-Fetal & Neonatal Medicine Mar. 2021, 35(25): 5970-5977.

National Institute of Diabetes and Digestive and Kidney Diseases (NIDDK), "2009 CKD-EPI Creatinine Calculator," Chronic Kidney Disease Epidemiology Collaboration (CKD-EPI) equation, last reviewed Dec. 2022, retrieved from URL <https://www.niddk.nih.gov/health-information/professionals/clinical-tools-patient-management/kidney-disease/laboratory-evaluation/glomerular-filtration-rate-calculators/historical>, 2 pages.

Neumann et al., "Hepatitis C Viral Dynamics in Vivo and the Antiviral Efficacy of Interferon-α Therapy", Science, 1998, 282: 103-107.

Nevalainen et al., "Effect of remdesivir post hospitalization for Covid-19 infection from the randomized Solidarity Finland trial," Nature Communications, Oct. 2022, 13(1): 6152.

Nguyen et al., "Favipiravir pharmacokinetics in Ebola-Infected patients of the JIKI trial reveals concentrations lower than targeted," PLoS Neglected Tropical Diseases, Feb. 2017, 11(2), 18 pages.

NIH [online], "Covid-19 Treatment Guidelines: Special Considerations During Pregnancy and After Delivery," last updated Apr. 20, 2023, retrieved from URL <https://www.covid19treatmentguidelines.nih.gov/special-populations/pregnancy/>, 8 pages.

NIH [online], "Drug-Drug Interactions Between Ritonavir-Boosted Nirmatrelvir (Paxlovid) and Concomitant Medications," last updated Mar. 6, 2023, retrieved from URL: <https://www.covid19treatmentguidelines.nih.gov/therapies/antivirals-including-antibody-products/ritonavir-boosted-nirmatrelvir--paxlovid-/paxlovid-drug-drug-interactions>, 8 pages.

Nilsson et al., "Discovery of 4'-azido-2'-deoxy-2'-C-methyl cytidine and prodrugs thereof: A potent inhibitor of Hepatitis C virus replication," Bioorganic & Medicinal Chemistry Letters, May 2012, 22(9):3265-68.

Nishimura et al., "Synthesis of pyrrolo[2,1-f][1,2,4]triazine C-nucleosides. Isosteres of sangivamycin, tubercidin, and toyocamycin," Carbohydrate Research, 2001, 331: 77-82.

Ogura et al., "Reaction of Ethynyl Compounds with Lactones," Journal of Organic Chemistry, 1972, 37(1): 72-75.

Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004, 3944-3953.

O'Mahoney, "The prevalence and long-term health effects of Long Covid among hospitalised and non-hospitalised populations: A systematic review and meta-analysis," EClinicalMedicine, Dec. 1, 2022, 55: 1-10.

O'Toole et al., "Tracking the international spread of SARS-CoV-2 lineages B.1.1.7 and B.1.351/501Y-V2," Wellcome Open Research, May 2021, 18 pages.

Otter et al., "Conformational Properties of Purine-Like C-Nucleosides," Nucleosides & Nucleotides, 1996, 15(1-3): 793-807.

Owen et al., "An oral SARS-CoV-2 Mpro Inhibitor Clinical Candidate for the Treatment of Covid-19," Science, Nov. 2021, 374(6575): 1586-1593.

Owusu et al., "A Comparison Analysis on Remdesivir, Favipiravir, Hydroxychloroquine, Chloroquine and Azithromycin in the Treatment of Corona Virus Disease 2019 (Covid-19)—A Review," World Journal of Pharmacy and Pharmaceutical Sciences, May 2020, 9(5): 121-133.

Ozturk et al., "Mortality analysis of Covid-19 infection in chronic kidney disease, haemodialysis and renal transplant patients compared with patients without kidney disease: a nationwide analysis from Turkey," Nephrology Dialysis Transplantation, Dec. 2020, 35(12): 2083-95.

Pagan et al., "Management of Critically Ill Pregnant Patients with Covid-19 Infection in a Rural State," American Journal of Perinatology, Jan. 2022, 39(2): 165-71.

Paharia, "Study indicates widespread SARS-CoV-2 exposure in wildlife," NewsMedical.net, Nov. 8, 2022, retrieved via Internet Archive Wayback Machine URL :<https://web.archive.org/web/20221109033955/https://www.news-medical.net/news/20221108/Study-indicates-widespread-SARS-CoV-2-exposure-in-wildlife.aspx>, 7 pages.

Pankiewicz et al., "C-Nucleoside Analogues of Nicotinamide Mononucleotide (NMN)," Nucleosides and Nucleotides, 1988, 7(5 &6): 589-593.

Pankiewicz et al., "Efficient Synthesis of 5-(β-D-Ribofuranosyl)nicotinamide and its α-Isomer," Journal of Organic Chemistry, 1988, 53: 3473-3479.

Patani et al., "Bioisosterism: a rational approach in drug design," Chem. Rev., 1996 96:3147-3176.

Patel et al., "Analysis of MarketScan Data for Immunosuppressive Conditions and Hospitalizations for Acute Respiratory Illness, United States," Emerging Infectious Diseases, Apr. 29, 2020; 26(8): 1720-30.

Patil et al., "4-Aza-7,9-Dideazaadenosine, a New Cytotoxic Synthetic C-Nucleoside Analogue of Adenosine," Tetrahedron Letters, 1994, 35(30): 5339-5342.

(56) References Cited

OTHER PUBLICATIONS

Patil et al., "C-Glycosylation of Substituted Heterocycles under Friedel-Crafts Conditions (II): Robosylation of Multi-Functionalized Thiophenes and Furans for the Synthesis of Purine-Like C-Nucleosides," Nucleosides & Nucleotides, 1990, 9(7): 937-956.

Patil et al., "Synthesis of Pyrrolo[2,1-f][1,2,4]triazine Congeners of Nucleic Acid Purines via the N-Amination of 2-Substituted Pyrroles," J. Het. Chem., 1994, 31: 781-786.

Patil et al., "Synthesis of some new thieno[3,4-d]pyrimidines and their C-nucleosides," Journal of Heterocyclic Chemistry, 1993, 30(2): 509-515.

PCT International Search Report and Written Opinion in International Appln. No. PCT/US2023/036039, dated Feb. 7, 2024, 12 pages.

Peart Akindele et al., "Effect of remdesivir post-exposure prophylaxis and treatment on pathogenesis of measles in rhesus macaques," Scientific Reports, Apr. 20, 2023, 13:6463.

Pelet et al., "High throughput screening assay for negative single stranded RNA virus polymerase inhibitors," J. Virol. Methods, Sep. 2005, 128(1-2): 29-36.

Perlis et al., "Prevalence and Correlates of Long Covid Symptoms Among US Adult," JAMA Network Open, Oct. 27, 2022; 5(10): 1-11.

Perrone et al., "Application of the Phosphoramidate ProTide Approach to 4'-Azidouridine Confers Sub-micromolar Potency versus Hepatitis C Virus on an Inactive Nucleoside", Journal of Medicinal Chemistry, 2007, 50(8):1840-1849.

Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.

Peterson et al., "Prodrug approaches to improving the oral absorption of antiviral nucleotide analogues," Expert Opinion, Drug Deliv., 2009, 6(4): 405-420.

Piccirilli et al., "A Direct Route to 3-(D-Ribofuranosyl)pyridine Nucleosides," Helvetica Chimica Acta, 1991, 74: 397-406.

Pierce-Williams et al., "Clinical course of severe and critical coronavirus disease 2019 in hospitalized pregnancies: a United States cohort study," American Journal of Obstetrics & Gynecology MFM, Aug. 2020, 2(3): 12 pages.

Pierra et al., "Synthesis and Pharmacokinetics of Valopicitabine (NM283), and Efficient Prodrug of the Potent Anti-HCV Agent 2'-C-Methylcytidine," Journal of Medicinal Chemistry, 2006, 49(22): 6614-6620.

Pilcer et al., "Formulation strategy and use of excipients in pulmonary drug delivery," International Journal of Pharmaceutics, Jun. 2010, 392(1-2): 1-19.

Pitts et al., "Efficacy in Multiple SARS-CoV-2 Animal Models Supports Phase 3 Dose Selection for Obeldesivir," presented at IDWeek, Boston, MA, USA, Oct. 11-15, 2023, Abstract 539.

Pitts et al., "Intravenous Delivery of GS-441524 is Efficacious in the African Green Monkey Model of SARS-CoV-2 Infection," Antiviral Research, Jul. 2022, 203: 9 pages.

Pitts et al., "Remdesivir and GS-441524 Retain Antiviral Activity against Delta, Omicron, and Other Emergent SARS-CoV-2 Variants," Antimicrobial agents and chemotherapy, May 9, 2022, 66(6): 13 pages.

Pizzorno et al., "In vitro evaluation of antiviral activity of single and combined repurposable drugs against SARS-CoV-2," Antiviral Research, Sep. 2020, 181: 104878.

Poduch et al., "Design of Inhibitors of Orotidine Monophosphate Decarboxylase Using Bioisosteric Replacement and Determination of Inhibition Kinetics," Journal of Medicinal Chemistry, 2006, 49(16): 4937-4945.

Porter et al., "Remdesivir (GS-5734) Is Efficacious in Cynomolgus Macaques Infected With Marburg Virus," The Journal of Infectious Diseases, Jun. 2020, 222(11): 1894-1901.

Porter et al., "Zika virus, drug discovery, and student projects," ScienceBlogs, Mar. 9, 2016, 7 pages.

Prasad et al., "Natural history of nonhuman primates after oral exposure to Ebola virus variant Makona," The Journal of Infectious Diseases, Jun. 2023, 22 pages.

Prasad et al., "Resistance of Cynomolgus Monkeys to Nipah and Hendra Virus Disease Is Associated With Cell-Mediated and Humoral Immunity," The Journal of Infectious Diseases, May 2020, 221(Suppl. 4): S436-447.

Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940): 1-16.

Puech et al., "Intracellular Delivery of Nucleoside Monophosphates through a Reductase-mediated Activation Process," Antiviral Research, 1993, 22(4): 155-174.

Radoshitzky et al., "Expanded profiling of Remdesivir as a broad-spectrum antiviral and low potential for interaction with other medications in vitro," Scientific Reports, Feb. 23, 2023, 13:3131.

Rahim et al., "Postexposure Protective Efficacy of T-705 (Favipiravir) Against Sudan Virus Infection in Guinea Pigs," The Journal of Infectious Diseases, Jul. 2018, 218(Suppl. 5): S649-S657.

Rajme-Lopez et al., "Early Outpatient Treatment With Remdesivir in Patients at High Risk for Severe Covid-19: A Prospective Cohort Study," Open Forum Infectious Diseases, Oct. 6, 2022, 9(10): 1-6.

Ramasamy et al., "Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor," J. Med. Chem., 1986, 29(11): 2231-2235.

Rao et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, 1988, 29(29): 3537-3540.

Rasmussen et al., "Nucleoside analog GS-441524; pharmacokinetics in different species, safety, and potential effectiveness against Covid-19," Pharmacol. Res. Perspect., Apr. 2022, 10(2):e00945.

Rebeaud et al., "SARS-CoV-2 and the Use of Chloroquine as an Antiviral Treatment," Frontiers in Medicine, Apr. 24, 2020, 7: 184, 6 pages.

Reddy et al., "Stereoselective Synthesis of Nucleoside Monophosphate HepDirectTM Prodrugs," Tet. Lett., 2005, 46: 4321-4324.

Remington's Pharmaceutical Science, 17th ed., Gennaro (ed)., 1985, Chapter 68, 58 pages.

Rodriguez et al., "Remdesivir Retains Potent Activity Against SARS-CoV-2 Variants of Concern," Poster #562, poster presented at: Conference on Retroviruses and Opportunistic Infections (CROI), Feb. 19-22, 2023, 1 page.

Ronco et al., "Kidney Involvement in Covid-19 and Rationale for Extracorporeal Therapies," Nature Reviews Nephrology, Apr. 2020, 16: 308-310.

Rosner-Tenerowicz et al. "Placental pathology in a pregnant woman with severe Covid-19 and successful ECMO treatment: a case report," BMC Pregnancy and Childbirth, Nov. 2021, 21: 760, 6 pages.

Ross et al., "Synthesis of Diastereomerically Pure Nucleotide and Phosphoramidates," J. Org. Chem., 2011, 76: 8311-8319.

Sacramento et al., "The clinically approved antiviral drug Sofosbuvir inhibits Zika Virus replication," Nature, Jan. 18, 2017, 7: 40920, 12 pages.

Sahakijpijarn et al., "Development of Remdesivir as a Dry Powder for Inhalation by Thin Film Freezing," Pharmaceutics, Oct. 2020, 12(11):1002, 27 pages.

Santos et al., "The Redpine Study: Efficacy and Safety of Remdesivir in People With Moderately and Severely Reduced Kidney Function Hospitalised for Covid-19 Pneumonia," Poster #2635, Poster presented at 33rd European Congress of Clinical Microbiology and Infectios Diseases (ECCMID), Apr. 15-18, 2023, 1 page.

Saroyo et al., "Remdesivir Treatment for Covid 19 in Pregnant Patients with Moderate to Severe Symptoms: Serial Case Report," Infectious Disease Reports, May 2021, 13(2): 437-443.

Schäfer et al., "Therapeutic efficacy of an oral nucleoside analog of remdesivir against SARS-CoV-2 pathogenesis in mice," bioRxiv Preprint, Sep. 17, 2021, 36 pages.

(56) References Cited

OTHER PUBLICATIONS

Schäfer et al., "Therapeutic treatment with an oral prodrug of the remdesivir parental nucleoside is protective against SARS-CoV-2 pathogenesis in mice," Science Translational Medicine, May 2022, 14(643), 16 pages.

Schindell et al., "Persistence and Sexual Transmission of Filoviruses," Viruses Dec. 2018, 10(12), 22 pages.

Schnettler et al., "Severe acute respiratory distress syndrome in coronavirus disease 2019-infected pregnancy: obstetric and intensive care considerations," American Journal of Obstetrics & Gynecology MFM, Aug. 2020, 2(Suppl 3): 10 pages.

Schnirring, "China releases genetic data on new coronavirus, now deadly," CIDRAP. News, Jan. 2020, retrieved on Mar. 15, 2022, retrieved from URL <https://www.cidrap.umn.edu/news-perspective/2020/01/china-releases-genetic-data-new-coronavirus-now-deadly>, 3 pages.

Schul et al., "A Dengue Fever Viremia Model in Mice Shows Reduction in Viral Replication and Suppression of the Inflammatory Response after Treatment with Antiviral Drugs," Journal of Infectious Diseases, 2007, 195: 665-674.

Schultz, "Prodrugs of Biologically Active Phosphate Esters," Bioorganic & Medicinal Chemistry, 2003, 11: 885-898.

Scott et al., "Interferon-a-2b Plus Ribavirin: A Review of its Use in the Management of Chronic Hepatitis C," Drugs, 2002, 62(3): 507-556.

Sendi et al., "First-generation oral antivirals against SARS-CoV-2," Clin. Microbiol. Infect., Sep. 2022, 28(9):1230-1235.

Sheahan et al., "Broad-spectrum antiviral GS-5734 inhibits both epidemic and zoonotic coronaviruses", Science Translational Medicine, Jun. 2017, 9(396):eaal3653, 11 pages.

Sheahan et al., "Comparative therapeutic efficacy of remdesivir and combination lopinavir, ritonavir, and interferon beta against MER-CoV," Nature Communications, 2020, 11(222): 1-14.

Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.

Shekunov et al., "Crystallization processes in pharmaceutical technology and drug delivery design," Journal of Crystal Growth, 2000, 211: 122-136.

Shetty et al., "Covid-19-Associated Glomerular Disease," Journal of the American Society of Nephrology, Jan. 2021, 32(1): 33-40.

Shi et al., "Synthesis and anti-viral activity of a series of d- and 1-2'-deoxy-2'-fluororibonucleosides in the subgenomic HCV replicon system," Bioorganic & Medicinal Chemistry, Mar. 2005, 13(5):1641-1652.

Siegel et al., "Discovery and Synthesis of a Phosphoramidate Prodrug of a Pyrrolo[2,1-f][triazin-4-amino] Adenine C-Nucleoside (GS-5734) for the Treatment of Ebola and Emerging Viruses," J. Med. Chem., 2017, 60, 5, 1648-1661 Supplementary Material.

Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.

Silverman et al., "The Organic Chemistry of Drug Design and Drug Action," Elsevier Science, 1992, pp. 19-23.

Silverman, "The Organic Chemistry of Drug Design and Drug Action," Elsevier Science, 2nd Ed., 2004, pp. 29-34.

Singh et al., "Treatment With Remdesivir in Two Pregnant Patients With Covid-19 Pneumonia," Cureus, May 2021, 13(5): 6 pages.

Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19): 7202-7218.

Song et al., "Risk and Outcome of Breakthrough COvid-19 Infections in Vaccinated Patients With Cancer: Real-World Evidence From the National Covid Cohort Collaborative," Journal of Clinical Oncology, May 1, 2022, 40(13): 1414-1427.

Spinelli et al., "Covid-19 Outcomes and Risk Factors Among People Living with HIV," Current HIV/AIDS Reports, Aug. 5, 2022, 19(5): 425-32.

Spinner et al., "Effect of Remdesivir vs Standard Care on Clinical Status at 11 Days in Patients With Moderate Covid-19: A Randomized Clinical Trial," Jama, Sep. 2020, 324(11): 1048-1057.

Srivastav et al., "Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 2010, 53(19): 7156-7166.

Ssentongo et al., BMC Infectious Diseases, "SARS-CoV-2 vaccine effectiveness against infection, symptomatic and severe Covid-19: a systematic review and meat-analysis", vol. 22, Article 439, 2022. (Year: 2022).

Stein et al., "Phosphorylation of Nucleoside Analog Antiretrovirals: A Review for Clinicians," Pharmacotherapy, Jan. 2001, 21(1): 11-34.

Stella et al., "Cyclodextrins," Toxicologic Pathology, 2008, 36(1): 30-42.

Streetman, "Drug Interaction Concerns for Covid-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.

Sun, "Remdesivir for Treatment of Covid-19: Combination of Pulmonary and IV Administration May Offer Additional Benefit", The AAPS Journal, 2020, 22(77):1-6.

Swank et al., "Persistent Circulating Severe Acute Respiratory Syndrome Coronavirus 2 Spike Is Associated With Post-acute Coronavirus Disease 2019 Sequelae," Clinical Infectious Diseases, Sep. 2, 2022, 76(3): e487-e490.

Szente et al., "Sulfobutylether-beta-cyclodextrin-enabled antiviral remdesivir: Characterization of electrospun- and lyophilized formulations," Carbohydrate Polymers, 2021, 264:118011, 8 pages.

Taki et al., "Ebanga™: The most recent FDA-approved drug for treating Ebola," Frontiers in Pharmacology, Mar. 2023, 14: 1-8.

Tan et al., "Combination Treatment With Remdesivir and Ivermectin Exerts Highly Synergistic and Potent Antiviral Activity Against Murine Coronavirus Infection," Frontiers in Cellular and Infection Microbiology, Jul. 30, 2021, 11(700502):1-10.

Tao et al., "Comparison of Anti-SARS-CoV-2 Activity and Intracellular Metabolism of Remdesivir and its Parent Nucleoside," Current Research in Pharmacology and Drug Discovery, 2021, 2, 7 pages.

Tapia et al., "Combination of a Mutagenic Agent with a Reverse Transcriptase Inhibitor Results n Systematic Inhibition of HIV-1 Infection," Virology, 2005, 338: 1-8.

Taylor et al., "Neutralizing Monoclonal Antibodies for Treatment of Covid-19." Nature Reviews Immunology, Apr. 2021, 21(6): 382-393.

Taylor, "Aulton's Pharmaceutics: The Design and Manufacture of Medicines; Chapter 37: Pulmonary Drug Delivery," 5th ed., Aulton et al (ed), 2018: 653-670.

The Recovery Collaborative Group, "Dexamethasone in Hospitalized Patients with Covid-19," New England Journal of Medicine, Feb. 2020, 384(8): 693-704.

Thi et al., "Rescue of non-human primates from advanced Sudan ebolavirus infection with lipid encapsulated siRNA," Nature Microbiology, Aug. 2016, 1: 16142, 21 pages.

Tong, "Gilead quashes microcap biotech's hope of partnering on oral Covid-19 drug," Endpoint News, Jan. 31, 2023, 2 pages.

Totura et al., "Broad-spectrum coronavirus antiviral drug discovery", Expert Opinion on Drug Discovery, Mar. 2019, 17 pages.

Towner et al., "Newly Discovered Ebola Virus Associated with Hemorrhagic Fever Outbreak in Uganda," PLoS Pathogens, 2008, 4(11): e1000212, 6 pages.

Tschesnokov et al., "Template-dependent inhibition of coronavirus RNA-dependent RNA polymerase by remdesivir reveals a second mechanism of action," J. Biol. Chem., 2020, 295(47): 16156-16165.

U.S. Department of Agriculture (USDA) [online], "Confirmed Cases of SARS-CoV-2 in Animals in the United States," last updated Aug. 29, 2023, retrieved on Aug. 29, 2023, retrieved from URL: <https://www.aphis.usda.gov/aphis/dashboards/tableau/sars-dashboard>, 1 page.

(56) References Cited

OTHER PUBLICATIONS

U.S. Department of Health and Human Services (HHS) [online], "Most common forms based on Pango lineage designations," last updated Aug. 25, 2023, retrieved on Aug. 29, 2023, retrieved from URL: <https://cov.lanl.gov/components/sequence/COV/pangocommonforms.comp>, 264 pages.

U.S. Food and Drug Administration (FDA), "First FDA-approved vaccine for the prevention of Ebola virus disease, marking a critical milestone in public health preparedness and response," Press Release, Dec. 19, 2019, 3 pages.

U.S. Food and Drug Administration (FDA), "Regulatory Classification of Pharmaceutical Co-Crystals Guidance for Industry," U.S. Department of Health and Human Services, Center for Drug Evaluation and Research (CDER), Feb. 2018, 7 pages.

Uchiyama et al., "O-selective Phosphorylation of Nucleosides without N-protection," J. Org. Chem., Jan. 1, 1993, 58(2): 373-379.

US Department of Health and Human Services [online] ,"What is Long COVID?" retrieved on Jul. 24, 2023, retrieved from URL <https://www.covid.gov/longcovid/definitions>, 2 pages.

Vaghefi et al., "Synthesis and Antiviral Activity of Certain Nucleoside 5'-Phosphonoformate Derivatives," Journal of Medicinal Chemistry, 1986, 29(8): 1389-1393.

Vandesompele et al., "Accurate normalization of real-time quantitative RT-PCR data by geometric averaging of multiple internal control genes," Genome Biology, Jun. 2002, 3(7): 1-12.

Vangeel et al., "Remdesivir, Molnupiravir and Nirmatrelvir remain active against SARS-CoV-2 Omicron and other variants of concern," Antiviral Research, Jan. 2022, 198: 3 pages.

Venkatachalam et al., "Effect of change in nucleoside structure on the activation and antiviral activity of phosphoramidate derivatives," Bioorganic & Medicinal Chemistry, 2005, 13: 5408-5423.

Vermillion et al., "Inhaled remdesivir reduces viral burden in a nonhuman primate model of SARS-CoV-2 infection," Science Translational Medicine, Dec. 2021, 20 pages.

Vieira et al., "Development of a Large-Scale Cyanation Process Using Continuous Flow Chemistry En Route to the Synthesis of Remdesivir," Organic Process Research & Development, May 2020, 24(10):2113-2121.

V'kovski et al., "Coronavirus Biology and Replication: Implications for SARS-CoV-2," Nature Reviews Microbiology, Oct. 2021, 19(3): 155-170.

Walker et al., "Plasma chloroquine and desethylchloroquine concentrations in children during and after chloroquine treatment for malaria.", British Journal Clinical Pharmacology, Dec. 1983, 16(6): 701-705.

Wang et al., "Analyses of Risk, Racial Disparity, and Outcomes Among US Patients With Cancer and Covid-19 Infection," JAMA Oncology, Dec. 10, 2021, 7(2): 220-227.

Wang et al., "Annovar: functional annotation of genetic variants from high-throughput sequencing data," Nucleic Acids Research, 2010, 38(16): e164, 7 pages.

Wang et al., "Preclinical Pharmacokinetics and In Vitro Properties of GS-441524, a Potential Oral Drug Candidate for Covid-19 Treatment," Frontiers in Pharmacology, Aug. 2022, 13: 16 pages.

Wang et al., "Remdesivir and chloroquine effectively inhibit the recently emerged novel coronavirus (2019-nCoV) in vitro", Cell Research, 2020, 30: 269-271.

Wang et al., "Remdesivir in adults with severe Covid-19: a randomised, double-blind, placebo-controlled, multicentre trial," Lancet, Apr. 29, 2020, 395: 1569-1578.

Warfield et al., "Homologous and heterologous protection of nonhuman primates by Ebola and Sudan virus-like particles," PLoS ONE, Mar. 2015, 10(3): 16 pages.

Warren et al., "Protection against filovirus diseases by a novel broad-spectrum nucleoside analogue BCX4430", Nature, Apr. 2014, 508(7496): 402-405.

Warren et al., "Therapeutic efficacy of the small molecules GS-5734 against Ebola virus in rhesus monkeys", Nature, Mar. 17, 2016, 531(7594): 381-385.

Warren et al., "Therapeutic efficacy of the small molecules GS-5734 against Ebola virus in rhesus monkeys", Nature, Mar. 17, 2016, 531(7594):381-385; Supplementary Information, 25 pages.

Wec et al., "Development of a Human Antibody Cocktail that Deploys Multiple Functions to Confer Pan-Ebolavirus Protection," Cell Host Microbe, Jan. 2019, 25(1): 39-48, el-e5.

Wei et al., "Potency and Pharmacokinetics of GS-441524 Derivatives Against SARS-CoV-2," Bioorganic & Medicinal Chemistry, Sep. 2021, 46: 12 pages.

Williamson et al., "Factors associated with Covid-19-related death using OpenSafely," Nature, Aug. 2020, 584(7821): 430-6.

Wohl et al., "Post-Ebola Symptoms 7 Years After Infection: The Natural History of Long Ebola," Clinical Infectious Diseases, Feb. 2023, 76(3): 835-840.

Wolfel et al., "Virological assessment of hospitalized patients with Covid-2019," Nature, Apr. 2020, 581: 465-470.

Woolsey et al., "A highly attenuated pan-filovirus VesiculoVax vaccine rapidly protects nonhuman primates against Marburg virus and three species of Ebolavirus," The Journal of Infectious Diseases, May 2023, 20 pages.

Woolsey et al., "A highly attenuated Vesiculovax vaccine rapidly protects nonhuman primates against lethal Marburg virus challenge," PLoS Neglected Tropical Diseases, May 2022, 16(5), 27 pages.

Woolsey et al., "Bundibugyo ebolavirus Survival Is Associated with Early Activation of Adaptive Immunity and Reduced Myeloid-Derived Suppressor Cell Signaling," mBio, Aug. 2021, 12(4), 20 pages.

Woolsey et al., "Natural history of Sudan ebolavirus infection in rhesus and cynomolgus macaques," Emerging Microbes & Infections, Jun. 2022, 11(1): 1635-46.

World Health Organization (WHO) [online], "A clinical case definition of post Covid-19 condition by a Delphi consensus," Oct. 6, 2021, retrieved from URL <https://www.who.int/publications/i/item/WHO-2019-nCOV-Post_COVID-19_condition-Clinical_case_definition-2021.1>, 27 pages.

World Health Organization (WHO) [online], "Clinical management of Covid-19: living guideline," Jan. 12, 2023, retrieved from URL <https://app.magicapp.org/#/guideline/j1WBYn>, 183 pages.

World Health Organization (WHO) [online], "Post Covid-19 condition (Long Covid)," Dec. 7, 2022, retrieved from URL <https://www.who.int/europe/news-room/fact-sheets/item/post-covid-19-condition>, 2 pages.

World Health Organization (WHO) [online], "Therapeutics and Covid-19: Living Guideline," Jul. 14, 2022, updated Jan. 13, 2023, retrieved from URL <https://www.who.int/publications/i/item/WHO-2019-nCoV-therapeutics-2022.4>, 142 pages.

World Health Organization (WHO) [online], "Tracking SARS-CoV-2 variants," last updated Aug. 17, 2023, retrieved on Aug. 25, 2023, retrieved from URL <https://www.who.int/en/activities/tracking-SARS-CoV-2-variants>, 11 pages.

World Health Organization (WHO), "Ebola haemorrhagic fever in Zaire, 1976: Report of an International Commission," Bulletin of the World Health Organization, 1978, 56(2): 271-293.

World Health Organization (WHO), "Updated working definitions and primary actions for SARS-CoV-2 variants," Aug. 17, 2023, 4 pages.

World Health Organization (WHO), "WHO Coronavirus (Covid-19) Dashboard," 2020, retrieved on Oct. 19, 2023, retrieved from URL <https://covid19.who.int/>, 1 page.

World Organisation for Animal Health, "SARS CoV-2 in Animals—Situation Report 22," Jun. 30, 2023, 3 pages.

Wu et al., "AKI and Collapsing Glomerulopathy Associated with Covid-19 and APOL1 High-Risk Genotype," Journal of the American Society of Nephrology, Aug. 2020, 31(8):1688-95.

Wu et al., "Synthetic Methodologies for C-Nucleosides," Synthesis, 2004, 10: 1533-1553.

Xie et al., "A nanoluciferase SARS-CoV-2 for rapid neutralization testing and screening of anti-infective drugs for Covid-19," Nature Communications, Oct. 15, 2020, 11(1):1-11.

Xie et al., "Engineering SARS-CoV-2 using a reverse genetic system," Nature protocols, Jan. 29, 2021, 16(3): 1761-1784.

(56) References Cited

OTHER PUBLICATIONS

Xie et al., "Long-term cardiovascular outcomes of Covid-19," Nature Medicine, Mar. 2022, 28(3): 583-90.

Xie et al., "Weinreb Amide Approach to the Practical Synthesis of a Key Remdesivir Intermediate," The Journal of Organic Chemistry, 2021, 86:5065-5072.

Xu et al., "Off-Target In Vitro Profiling Demonstrates that Remdesivir Is a Highly Selective Antiviral Agent," Antimicrobial Agents and Chemotherapy, Jan. 20, 2021, 65(2), 14 pages.

Yamamoto et al., "High-Dose Corticosteroids for a Pregnant Woman Critically Ill With Coronavirus Disease 2019," Cureus, Aug. 2021, 13(8): 5 pages.

Yamanaka et al., "Metabolic Studies on BMS-200475, a New Antiviral Compound. Active against Hepatitis B Virus," Antimicrobial Agents and Chemotherapy, 1999; p. 43(1): 190.

Yan et al., "Advantages of the Parent Nucleoside GS-441524 over Remdesivir for Covid-19 Treatment," ACS Medicinal Chemistry Letters, Jun. 30, 2020, 11(7):1361-1366.

Yan et al., "Gilead should ditch remdesivir and focus on its simpler and safer ancestor," STAT Health Care News, May 14, 2020, 6 pages.

Yan et al., "Pharmacokinetics of 1 Orally Administered GS-441524 in Dogs," bioRxiv Preprint, May 31, 2021, 18 pages.

Yang et al., "Biotransformation and transplacental transfer of the anti-viral remdesivir and predominant metabolite, GS-441524 in pregnant rats," EBioMedicine, Jul. 2022, 81: 11 pages.

Yang et al., "Lewis acid catalyzed direct cyanation of indoles and pyrroles with N-cyano-N-phenyl-p-toluenesulfonamide (NCTS)," Organic Letters, 2011, 13(20): 5608-5611.

Yates et al., "The evolution of antiviral nucleoside analogues: A review for chemists and non-chemists. PartII: Complex modifications to the nucleoside scaffold", Antiviral Research, Dec. 8, 2018, 162: 5-21.

Yoon et al., "High-throughput screening-based identification of paramyxovirus inhibitors," J. Biomol. Screen., Aug. 2008, 13(7): 591-608.

Yoshimura et al., "Synthesis and Biological Evaluation of 1'-C-Cyano-Pyrimidine Nucleosides," Nucleosides & Nucleotides, 1996, 15(1-3): 305-324.

Youssef et al., "Brief Report: Rapid Clinical Recovery From Critical Coronavirus Disease 2019 With Respiratory Failure in a Pregnant Patient Treated With IV Vasoactive Intestinal Peptide," Critical Care Explorations, Jan. 2022, 4(1): e0607.

Zeng et al., "Identification and pathological characterization of persistent asymptomatic Ebola virus infection in rhesus monkeys," Nature Microbiology, Jul. 2017, 2(1), 11 pages.

Zhang et al., "A bacterial artificial chromosome (BAC)-vectored noninfectious replicon of SARS-CoV-2", Antiviral Research, Jan. 2021, 185(1), 9 pages.

Zhang et al., "A Practical Synthesis of (2R)-3,5-di-O-benzoyl-2-fluoro-2-C-methyl-D-ribono-y-lactone", Tetrahedron: Asymmetry, 2009, 20: 305-312.

Zhang et al., "Pharmacokinetics & Safety of Remdesivir in Renal Impairment," Poster # 083, Presented at 2022 American College of Clinical Pharmacology Annual Meeting, Sep. 11, 2022, 1 page.

Zhu et al., "A novel coronavirus from patients with pneumonia in China, 2019," New. England Journal of Medicine, Jan. 24, 2020, 14 pages.

U.S. Appl. No. 18/410,236, filed Jan. 11, 2023, Elaine Bunyan.
U.S. Appl. No. 18/237,152, filed Aug. 23, 2023, Mark J. Bartlett.
U.S. Appl. No. 18/355,813, filed Jun. 23, 2021, Daniel H. Byun.
U.S. Appl. No. 18/215,881, filed Jun. 29, 2023, Kassibla B. Dempah.
Kern, "In vitro activity of potential anti-poxvirus agents," Antiviral Research, Jan. 2003, 57(1-2):35-40.
Nabiqasim Industries, "IVIREM Remdesivir—100mg," Product Brochure, 2020, 4 pages.
Nakanga, Wisdom P., et al. "Prevalence of impaired renal function among rural and urban populations: findings of a cross-sectional study in Malawi." Wellcome open research 4 (2019).

Rajsri et al., "Poxvirus-driven human diseases and emerging therapeutics," Therapeutic Advances in Infectious Disease, Nov. 14, 2022, 9:20499361221136751, 18 pages.

Wang et al., "Evaluation of the efficacy and safety of intravenous remdesivir in adult patients with severe Covid-19: study protocol for a phase 3 randomized, double-blind, placebo-controlled, multicentre trial," Trials, May 24, 2020, 21(1):422, 11 pages.

wmic.wales.nhs.uk, "Evidence Summary: Antiviral treatment options for human monkeypox infection," Jun. 1, 2022, retrieved on Mar. 4, 2024, retrieved from URL<https://www.wmic.wales.nhs.uk/wp-content/uploads/2022/06/Evidence-Summary-Table-final.pdf>, 6 pages.

Taiwanese Office Action in Taiwanese Appln. No. 112141111, dated Jun. 19, 2024, 22 pages (with English translation).

U.S. Appl. No. 13/189,373, filed Jul. 22, 2011, Richard L. Mackman.
U.S. Appl. No. 14/613,719, filed Feb. 4, 2015, Richard L. Mackman.
U.S. Appl. No. 14/579,348, filed Dec. 22, 2014, Richard L. Mackman.
U.S. Appl. No. 16/042,085, filed Jul. 23, 2018, Richard L. Mackman.
U.S. Appl. No. 16/879,491, filed May 20, 2020, Richard L. Mackman.
U.S. Appl. No. 17/854,818, filed Jun. 30, 2022, Richard L. Mackman.
U.S. Appl. No. 17/333,389, filed May 28, 2021, Tomas Cihlar.
U.S. Appl. No. 17/676,920, filed Feb. 22, 2022, Tomas Cihlar.
U.S. Appl. No. 18/128,850, filed Mar. 30, 2023, Tomas Cihlar.
U.S. Appl. No. 18/540,002, filed Dec. 14, 2023, Tomas Cihlar.
U.S. Appl. No. 18/791,542, filed Aug. 1, 2024, Tomas Cihlar.
U.S. Appl. No. 17/222,125, filed Apr. 5, 2021, Scott Ellis.
U.S. Appl. No. 18/202,751, filed May 26, 2023, Scott Ellis.
U.S. Appl. No. 17/158,391, filed Jan. 26, 2021, Tomas Cihlar.
U.S. Appl. No. 18/131,106, filed Apr. 5, 2023, Tomas Cihlar.
U.S. Appl. No. 18/735,429, filed Jun. 6, 2024, Tomas Cihlar.
U.S. Appl. No. 17/198,829, filed Mar. 11, 2021, Pavel R. Badalov.
U.S. Appl. No. 18/108,480, filed Feb. 10, 2023, Pavel R. Badalov.
U.S. Appl. No. 18/655,876, filed May 6, 2024, Pavel R. Badalov.
U.S. Appl. No. 16/031,620, filed Jul. 10, 2018, Nate Larson.
U.S. Appl. No. 16/865,209, filed May 1, 2020, Nate Larson.
U.S. Appl. No. 17/585,651, filed Jan. 27, 2022, Nate Larson.
U.S. Appl. No. 18/241,303, filed Sep. 1, 2023, Nate Larson.
U.S. Appl. No. 15/919,750, filed Mar. 13, 2018, Michel Joseph Perron.
U.S. Appl. No. 16/852,102, filed Apr. 17, 2020, Michel Joseph Perron.
U.S. Appl. No. 17/578,682, filed Jan. 19, 2022, Michel Joseph Perron.
U.S. Appl. No. 17/895,123, filed Aug. 25, 2022, Michel Joseph Perron.
U.S. Appl. No. 18/133,612, filed Apr. 12, 2023, Michel Joseph Perron.
U.S. Appl. No. 18/519,194, filed Nov. 27, 2023, Michel Joseph Perron.
U.S. Appl. No. 18/761,601, filed Jul. 2, 2024, Michel Joseph Perron.
U.S. Appl. No. 15/964,597, filed Apr. 27, 2018, Katrien Brak.
U.S. Appl. No. 17/069,248, filed Oct. 13, 2020, Katrien Brak.
U.S. Appl. No. 18/099,477, filed Jan. 20, 2023, Katrien Brak.
U.S. Appl. No. 18/673,406, filed May 24, 2024, Katrien Brak.
U.S. Appl. No. 15/267,433, filed Sep. 16, 2016, Michael O'Neil Hanrahan Clarke.
U.S. Appl. No. 16/265,016, filed Feb. 1, 2019, Michael O'Neil Hanrahan Clarke.
U.S. Appl. No. 16/863,566, filed Apr. 30, 2020, Michael O'Neil Hanrahan Clarke.
U.S. Appl. No. 17/222,066, filed Apr. 5, 2021, Michael O'Neil Hanrahan Clarke.
U.S. Appl. No. 17/748,400, filed May 19, 2022, Michael O'Neil Hanrahan Clarke.
U.S. Appl. No. 18/402,949, filed Jan. 3, 2024, Michael O'Neil Hanrahan Clarke.
U.S. Appl. No. 14/926,063, filed Oct. 29, 2015, Steven Donald Axt.
U.S. Appl. No. 16/692,966, filed Nov. 22, 2019, Steven Axt.

(56) References Cited

OTHER PUBLICATIONS

U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 17/579,650, filed Jan. 20, 2022, Byoung Kwon Chun.
U.S. Appl. No. 17/897,380, filed Aug. 29, 2022, Byoung Kwon Chun.
U.S. Appl. No. 18/134,792, filed Apr. 14, 2023, Byoung Kwon Chun.
U.S. Appl. No. 18/523,984, filed Nov. 30, 2023, Byoung Kwon Chun
U.S. Appl. No. 18/773,661, filed Jul. 16, 2024, Byoung Kwon Chun.
U.S. Appl. No. 14/746,430, filed Jun. 22, 2015, Aesop Cho.
U.S. Appl. No. 13/813,886, filed Jun. 25, 2013, Aesop Cho.
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2021, Thomas Butler.
U.S. Appl. No. 12/428,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 18/286,971, filed Oct. 13, 2023, Stacy Bremner.
U.S. Appl. No. 17/458,023, filed Aug. 26, 2021, Elaine Bunyan.
U.S. Appl. No. 18/098,950, filed Jan. 19, 2023, Elaine Bunyan.
U.S. Appl. No. 18/410,236, filed Jan. 11, 2024, Elaine Bunyan.
U.S. Appl. No. 18/115,895, filed Mar. 1, 2023, Rao V. Kalla.
U.S. Appl. No. 18/115,955, filed Mar. 1, 2023, Mark J. Bartlett.
U.S. Appl. No. 18/117,858, filed Mar. 6, 2023, Mark J. Bartlett.
U.S. Appl. No. 18/117,878, filed Mar. 6, 2023, Mark J. Bartlett.
U.S. Appl. No. 18/117,913, filed Mar. 6, 2023, Mark J. Bartlett.
U.S. Appl. No. 18/237,152, filed Aug. 25, 2023, Mark J. Bartlett.
U.S. Appl. No. 18/601,528, filed Mar. 11, 2024, Mark J. Bartlett.
U.S. Appl. No. 17/355,813, filed Jun. 23, 2021, Daniel H. Byun.
U.S. Appl. No. 18/544,561, filed Dec. 19, 2023, Daniel H. Byun.
U.S. Appl. No. 18/205,745, filed Jun. 5, 2023, Roy Maxim Bannister.
U.S. Appl. No. 18/243,812, filed Sep. 8, 2023, Casey B. Davis.
U.S. Appl. No. 18/394,488, filed Dec. 22, 2023, Casey B. Davis.
U.S. Appl. No. 18/512,088, filed Nov. 17, 2023, John Philip Bilello.
U.S. Appl. No. 18/215,881, filed Jun. 29, 2023, Kassibla E. Dempah.
U.S. Appl. No. 18/384,060, filed Oct. 26, 2023, Kimberly T. Barrett.
U.S. Appl. No. 18/431,038, filed Feb. 2, 2024, Kimberly T. Barrett.
U.S. Appl. No. 18/215,217, filed Jun. 28, 2023, Kassibla E. Dempah.
U.S. Appl. No. 18/884,419, filed Sep. 13, 2024, Mark J. Bartlett.
U.S. Appl. No. 18/825,549, filed Sep. 5, 2024, Kassibla E. Dempah.
U.S. Appl. No. 18/645671, filed Apr. 25, 2024, Mark J. Bartlett.

* cited by examiner

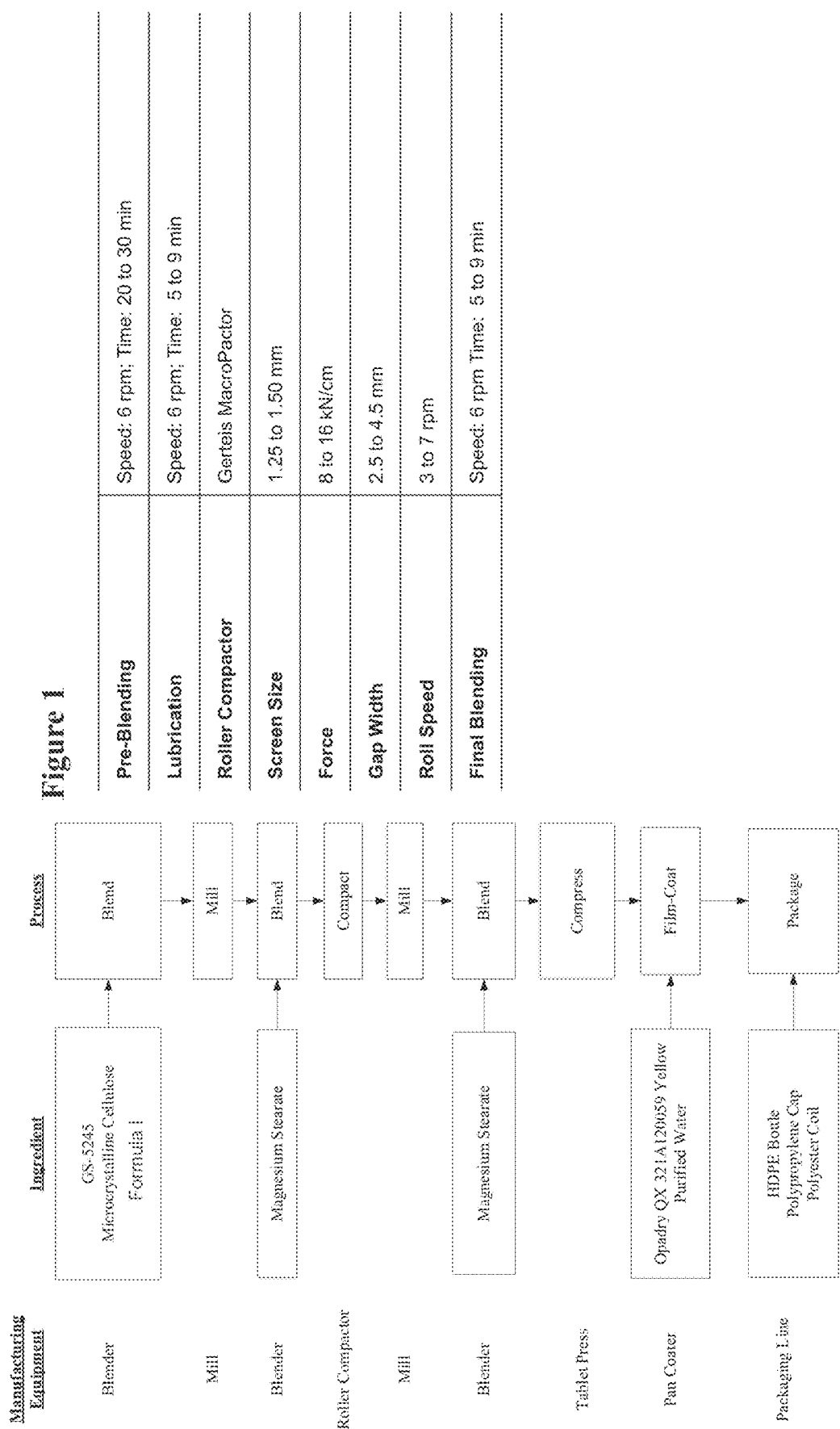

Figure 2

| Test / Time | Formulation F1, 100 mg | | | Formulation F2, 500 mg | | | Formulation F3, 100 mg | | | Formulation F4, 500 mg | | |
| --- | --- | --- | --- | --- | --- | --- | --- | --- | --- | --- | --- | --- |
| | T0 | 30°C/75% RH 9M | 40°C/75% RH 6M | T0 | 30°C/75% RH 9M | 40°C/75% RH 6M | T0 | 30°C/75% RH 6M | 40°C/75% RH 6M | T0 | 30°C/75% RH 6M | 40°C/75% RH 6M |
| Appearance | Conforms | Conforms | Conforms | Conforms | Conforms | Conforms | Conforms | Conforms | Conforms | Conforms | Conforms | Conforms |
| Water Content % | 3.1 | 3.7 | 4.0 | 2.7 | 2.7 | 3.2 | 2.5 | 3.5 | 3.8 | 2.2 | 2.7 | 3.0 |
| Assay (%LC) | 101.6 | 100.9 | 99.6 | 102.4 | 101.3 | 101.3 | 104.3 | 104.0 | 103.2 | 103.9 | 102.9 | 102.2 |
| Total Imp. | 1.1 | 1.1 | 1.1 | 1.1 | 1.1 | 1.1 | 1.2 | 1.2 | 1.2 | 1.2 | 1.2 | 1.2 |
| GS-441524 | 1.13 | 1.10 | 1.11 | 1.13 | 1.10 | 1.13 | 1.22 | 1.21 | 1.19 | 1.20 | 1.19 | 1.19 |
| Compound A | | Tr (0.027) | Tr (0.026) | | Tr (0.027) | Tr (0.026) | | | | | | |
| RRT 0.56 (Compound B) | | | Tr (0.033) | | | | | | | | | |
| %Dissolved at 45 mins | 101 | 97 | 95 | 102 | 99 | 99 | 96 | 97 | 94 | 98 | 98 | 98 |

Empty space: ND (<0.025%)
Tr: trace (<0.05%)

Figure 3

| Test / Time | Formulation F5 350 mg, open dish | | Formulation F6 700 mg, in 6 mil Aclar | | 700 mg, open dish | Formulation F7 500 mg, in 60 mL bottle, no desiccant | |
|---|---|---|---|---|---|---|---|
| | Initial T=0 | 40°C/75% RH 1 Month | Initial T=0 | 40°C/75% RH 3 Month | 40°C/75% RH 3 Month | Initial T=0 | 40°C/75% RH 1 Month |
| Appearance | * | * | ** | ** | ** | ** | ** |
| Water Content % | 2.0 | 4.5 | 2.6 | 2.7 | 4.5 | 2.1 | 2.3 |
| Assay (%LC) | 101.1 | 98.9 | 100.3 | 100.3 | 100.3 | 99.1 | 99.6 |
| Total Imp. | 0.0 | 0.1 | 0.3 | 0.2 | 0.3 | 0.0 | 0.1 |
|   GS-441524 | Trace | 0.06 | Trace | Trace | 0.09 | Trace | 0.06 |
|   Compound C | Trace | Trace | Trace | Trace | Trace | Trace | Trace |
|   Compound D | | | 0.28 | 0.18 | 0.17 | | |
| %Dissolved at 45 mins | 101 | 100 | 98 | 100 | 97 | 100 | 100 |

- 500 mg strength staged in bottles, with and without 1 g desiccant, up to 3M at 40°C/75% RH showed modest water content changes (NMT ±0.4%)

*Oval-shaped, film-coated light yellow
**Capsule-shaped, film-coated light yellow
Empty space: ND Dissolution methods: Type 2 apparatus, 20 mM sodium acetate, pH 4.5 with 0.5% tween 20, 75 rpm, 900 mL (350 mg) or 1000 mL (500 mg)
700 mg: Type 2 apparatus, 25 mM sodium acetate, pH 4.5 w/ 0.25% SLS, 1000 mL

Figure 4

| | T0 | 30 °C/75% RH, 0g Desiccant | | 40 °C/75% RH, 0g Desiccant | | |
|---|---|---|---|---|---|---|
| | | 3M | 6M | 1M | 3M | 6M |
| Water Content % | 1.8 | 2.4 | 2.6 | 2.2 | 2.7 | 3.2 |
| Assay (%LC) | 100.9 | 100.8 | 98.7 | 100.0 | 100.4 | 98.4 |
| Total Imp. | 0.0 | 0.0 | 0.0 | 0.1 | 0.0 | 0.0 |
| GS-441524 (%) | tr (0.0706) | tr (0.0917) | tr (0.0941) | tr (0.0924) | tr (0.0983) | tr (0.0972) |
| Compound D (%) | tr (0.0718) | tr (0.0861) | tr (0.0839) | 0.10 | tr (0.0905) | tr (0.0860) |
| %Dissolved at 30 min | 98 | 100 | 98 | 99 | 99 | 99 |

ND: not detected, < 0.05 %
tr: trace ≥0.05 % but <0.10 %
*Note: Single tablet used for Assay/Imp testing

Figure 5

| | T0 | 30 °C/75% RH, 0g Desiccant | 40 °C/75% RH, 0g Desiccant | |
|---|---|---|---|---|
| | | 3M | 1M | 3M |
| Water Content % | 2.1 | 2.5 | 2.4 | 2.9 |
| Assay (%LC) | 98.3 | 100.0 | 99.4 | 100.0 |
| Total Imp. | 0.0 | 0.0 | 0.0 | 0.0 |
| GS-441524 (%) | trace (0.0765) | trace (0.0918) | trace (0.0838) | trace (0.0991) |
| Compound D (%) | trace (0.0835) | trace (0.0915) | trace (0.0933) | trace (0.0972) |
| %Dissolved at 30 min | 98 | 98 | 97 | 98 |

ND: not detected, < 0.05 %
tr: trace ≥0.05 % but <0.10 %
*Note: Single tablet used for Assay/Imp testing

Figure 6

| Test | T0 | 40 °C/75% RH, 0g Desiccant |
|---|---|---|
| | | 1M |
| Water Content % | 2.4 | 2.6 |
| Assay (%LC) | 101.7 | 99.5 |
| Total Imp. | 0.0 | 0.0 |
| GS-441524 (%) | trace (0.0723) | trace (0.0753) |
| Compound D (%) | trace (0.0839) | trace (0.0770) |
| %Dissolved at 30 min | 99 | 99 |

ND: not detected, < 0.05 %
tr: trace ≥0.05 % but <0.10 %
*Note: Single tablet used for Assay/Imp testing

PHARMACEUTICAL FORMULATIONS AND USES THEREOF

CROSS REFERENCE TO RELATED APPLICATIONS

This application is a continuation of U.S. Ser. No. 18/384,060, filed Oct. 26, 2023, which claims priority to U.S. Provisional Application No. 63/381,272, filed Oct. 27, 2022 and U.S. Provisional Application 63/508,567, filed Jun. 16, 2023, and each application is hereby incorporated by reference in its entirety for all purposes.

TECHNICAL FIELD

Pharmaceutical formulations suitable for treating viral infections such as coronavirus infections, pneumoviridae virus infections, picornaviridae virus infections, flaviviridae virus infections, orthomyxovirus infections, and paramyxoviridae virus infections are provided. In particular solid oral dosage forms comprising the compound of Formula I, and uses thereof are provided.

BACKGROUND

The compound of Formula I is an antiviral agent,

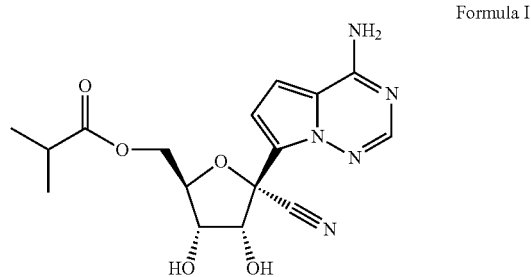 [SMILES: CC(C)C(=O)OC[C@H]1O[C@@](C#N)(c2ccc3c(N)ncnn23)[C@H](O)[C@@H]1O]

Formula I

The compound of Formula I, methods of making it, as well as its salts and polymorph forms are described in WO 2022/047065 (Compound 15). CN114869893 describes solid dosage forms, in particular tablets, of the compound of Formula I. The solid dosage forms disclosed in CN114869893 are obtained by wet granulation process and are characterized by low loading of the compound of Formula I (24.4%). The issue of low dose loading, i.e., percent Formula I content of the formulation, is not addressed in CN114869893.

Thus, there is a need for developing solid dosage forms (e.g. tablet/capsule dosage forms) comprising higher loading of the compound of Formula I. High drug loading enables the tablets/capsules to have suitable size in order to allow the patient to easily swallow the tablets/capsules. Higher drug load also helps minimize the number of tablets/capsules required per dose, which may lead to better patient compliance.

The overall physical properties and manufacturability of low drug loading formulations is determined predominantly by the inactive ingredients or excipients in the formulation. However, at high drug loading, the contribution of the physical properties of the active pharmaceutical ingredient ("API") to the manufacturability of a formulation becomes predominant. Not all APIs possess the necessary properties with respect to compressibility that are required in order to obtain a high load tablet using a dry granulation process.

Generally, most small molecule API's, can be formulated in low dose forms because the physical properties of the excipients utilized in the formulations dominate the properties of the solid composition, rather than the physical properties of the API itself. As drug loading increases the physicochemical characteristics of the drug substance become increasing dominant in the tablet manufacturing process. It is common to include filler excipients in a single formulation that possess brittle characteristics and others that possess ductile/plastic characteristics. The combination of the brittle and plastic type materials in a given formulation are important to the "manufacturability" of that formulation. However, because API's can have a full spectrum of physical properties and are not selected based on these physical properties, it is not to be expected that a particular API would have the physical properties to favorably contribute to an overall formulation in terms of manufacturability and stability. In fact, it is not infrequent that it is the physical properties of the API that actually present the largest obstacle to creating a workable formulation. It is therefore surprising and unanticipated where it is found that an API can be formulated in a dry granulating manufacturing process with drug loads in excess of 40%. The ability to prepare Formula I tablets at a drug loading in excess of 40%, for example using a dry granulation process, as described below is a surprising observation.

SUMMARY

In one aspect, the present disclosure provides a pharmaceutical formulation, comprising: (i) a compound expressed by formula I:

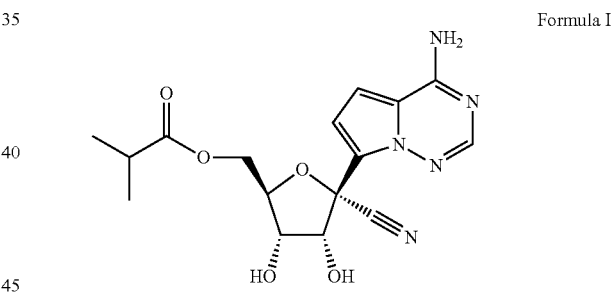

Formula I or a pharmaceutically acceptable salt thereof; (ii) a filler; (iii) a disintegrating agent; and (iv) a lubricant; wherein the compound of Formula I is present in an amount of about 40 wt % to about 70 wt %. In some embodiments, the pharmaceutical formulation comprises the filler in an amount of about 20 wt % to about 60 wt %; the disintegrating agent in an amount of about 1 wt % to about 10% wt %; and the lubricant in an amount of about 0.5 wt % to about 5% wt %. In some embodiments, the pharmaceutical formulation comprises the filler in an amount of about 40 wt % to about 50 wt %; the disintegrating agent in an amount of about 1 wt % to about 10 wt %; and the lubricant in an amount of about 0.5 wt % to about 5 wt %. In some embodiments, the pharmaceutical formulation comprises: (i) the compound of Formula I in an amount of about 45 wt % to about 55 wt %; (ii) the filler in an amount of about 44 wt % to about 46 wt %; (iii) the disintegrating agent in an amount of about 3 wt % to about 5 wt %; and (iv) the lubricant in an amount of about 0.5 wt % to about 2 wt %. In some embodiments, the pharmaceutical formulation comprises: (i) the compound of Formula I in an amount of about 50 wt %; (ii) the filler in an amount of about 44 wt % to about 46 wt %; (iii) the disintegrating agent in an amount of about 3 wt % to about 5 wt %; and (iv) the lubricant in an amount of about 0.5 wt % to about 2 wt %. In some embodiments, the filler is microcrystalline cellulose, lactose, mannitol, or dicalcium phosphate. In some embodiments, the filler is microcrystalline cellulose. In some embodiments, the disintegrating agent is starch, pre-gelatinized starch, hydroxypropyl starch, celluloses, cross-linked PVP (crospovidone), sodium starch glycolate, or croscarmellose sodium. In some embodiments, the disintegrating agent is crospovidone. In some embodiments, the lubricant is stearic acid, sodium stearyl fumarate, or magnesium stearate. In some embodiments, the lubricant is magnesium stearate. In some embodiments, the pharmaceutical formulation comprises about 100 mg to about 700 mg of the compound of Formula I. In some embodiments, the pharmaceutical formulation comprises about 100 mg of the compound of Formula I. In some embodiments, the pharmaceutical formulation comprises about 350 mg of the compound of Formula I. In some embodiments, the pharmaceutical formulation comprises about 500 mg of the compound of Formula I.

In one aspect, the current disclosure provides a tablet comprising: (i) a compound of Formula I, or a pharmaceutically acceptable salt thereof (ii) a filler, (iii) a disintegrating agent, and (iv) a lubricant; wherein the compound of Formula I is present in an amount of about 40 wt % to about 70 wt %. In some embodiments, the tablet comprises the filler in an amount of about 20 wt % to about 60% wt %, the disintegrating agent in an amount of about 1 wt % to about 10 wt %, and the lubricant in an amount of about 0.5 wt % to about 5% wt %. In some embodiments, the tablet comprises the filler in an amount of about 40 wt % to about 50 wt %, the disintegrating agent in an amount of about 1 wt % to about 10% wt %, and the lubricant in an amount of about 0.5 wt % to about 5 wt %. In some embodiments, the tablet comprises (i) the compound of Formula I in an amount of about 45 wt % to about 55 wt %, (ii) the filler in an amount of about 44 wt % to about 46 wt %, (iii) the disintegrating agent in an amount of about 3 wt % to about 5 wt %, and (iv) the lubricant in an amount of about 0.5 wt % to about 2 wt %. In some embodiments, the tablet comprises (i) the compound of Formula I in an amount of about 50 wt %, (ii) the filler in an amount of about 44 wt % to about 46 wt %, (iii) the disintegrating agent in an amount of about 3 wt % to about 5 wt %, and (iv) the lubricant in an amount of about 0.5 wt % to about 2 wt %. In some embodiments, the filler is microcrystalline cellulose, lactose, mannitol, or dicalcium phosphate. In some embodiments, the filler is microcrystalline cellulose. In some embodiments, the disintegrating agent is starch, pre-gelatinized starch, hydroxypropyl starch, celluloses, cross-linked PVP (crospovidone), sodium starch glycolate, or croscarmellose sodium. In some embodiments, the disintegrating agent is crospovidone. In some embodiments, the lubricant is stearic acid, sodium stearyl fumarate, magnesium stearate, or a combination thereof. In some embodiments, the lubricant is magnesium stearate. In some embodiments, the tablet comprises about 100 mg to about 700 mg of the compound of Formula I. In some embodiments, the tablet comprises about 100 mg of the compound of Formula I. In some embodiments, the tablet comprises about 350 mg of the compound of Formula I. In some embodiments, the tablet comprises about 500 mg of the compound of Formula I.

In one aspect, the present disclosure provides tablet comprising (i) the compound of Formula I in an amount of about 50-700 mg, (ii) microcrystalline cellulose in an amount of about 50 mg to about 500 mg, (iii) crospovidone in an amount of about 5 mg to 50 mg, and (iv) magnesium stearate in an amount of about 1 mg to about 20 mg. In some embodiments, the tablet comprises (i) the compound of Formula I in an amount of about 100 mg, (ii) microcrystalline cellulose in an amount of about 89 mg, (iii) crospovidone in an amount of about 8 mg, and (iv) magnesium stearate in an amount of about 3 mg. In some embodiments, the tablet comprises (i) the compound of Formula I in an amount of about 500 mg, (ii) microcrystalline cellulose in an amount of about 445 mg, (iii) crospovidone in an amount of about 40 mg; and (iv) magnesium stearate in an amount of about 10 mg. In some embodiments, the tablet comprises (i) the compound of Formula I in an amount of about 350 mg, (ii) microcrystalline cellulose in an amount of about 315 mg, (iii) crospovidone in an amount of about 28 mg. and (iv) magnesium stearate in an amount of about 7 mg.

In one aspect the disclosure provides a tablet comprising (a) a tablet core and (b) a film coat; wherein the tablet core comprises (i) a compound of Formula I, or a pharmaceutically acceptable salt thereof, (ii) a filler, (iii) a disintegrating agent; and (iv) a lubricant; wherein the compound of Formula I is present in an amount of about 40 wt % to about 70 wt %. In some embodiments, the tablet comprises the filler in an amount of about 20 wt % to about 60 wt %; the disintegrating agent in an amount of about 1 wt % to about 10 wt %; and the lubricant in an amount of about 0.5 wt % to about 5 wt %. In some embodiments, the tablet core comprises the filler in an amount of about 40% to about 50% by weight, the disintegrating agent in an amount of about T % to about 10% by weight (wt %), and the lubricant in an amount of about 0.5% to about 5% by weight (wt %). In some embodiments, the tablet core comprises (i) the compound of Formula I in an amount of about 45-55 wt %, (ii) the filler in an amount of about 44% to about 46% by weight, (iii) the disintegrating agent in an amount of about 3% to about 5% by weight (wt %), (iii) the lubricant in an amount of about 0.5 wt % to about 2 wt %. In some embodiments, the tablet core comprises (i) the compound of Formula I in an amount of about 50 wt %, (ii) the filler in an amount of about 44 wt % to about 46 wt %, (iii) the disintegrating agent in an amount of about 3 wt % to about 5 wt %; and (iv) the lubricant in an amount of about 0.5 wt % to about 2 wt %. In some embodiments, the film coat comprises Opadry® II. In some embodiments, the film coat comprises Opadry® QX. In some embodiments, the film coat comprises Opadry® II purple. In some embodiments, the film coat comprises Opadry® II yellow. In some embodiments, the film coat comprises Opadry® QX yellow. In some embodiments, the film coat comprises titanium free variants of Opadry®. In some embodiments, the filler is microcrystalline cellulose, lactose, mannitol, or dicalcium phosphate. In some embodiments, the filler is microcrystalline cellulose. In some embodiments, the disintegrating agent is starch, pre-gelatinized starch, hydroxypropyl starch, celluloses, cross-linked PVP (crospovidone), sodium starch glycolate, or croscarmellose sodium. In some embodiments, the disintegrating agent is crospovidone. In some embodiments, the lubricant is stearic acid, sodium stearyl fumarate, or magnesium stearate. In some embodiments, the lubricant is magnesium stearate. In some embodiments, the tablet comprises about 100 mg to about 700 mg of the compound of Formula I. In some embodiments, about 100 mg of the compound of Formula I. In some embodiments, the tablet comprises about 350 mg of the compound of Formula I. In some embodiments, the tablet comprises about 500 mg of the compound of Formula I.

In one aspect, the disclosure provides a method of treating a viral infection in a patient in need thereof, the method comprising administering to the human a pharmaceutical formulation or a tablet provided herein. In some embodiments, the method comprises administering to the human at least one additional therapeutic or prophylactic agent. In some embodiments, the viral infection is a coronavirus infection. In some embodiments, the viral infection is a zoonotic coronavirus infection. In some embodiments, the viral infection is caused by a virus having at least 70% sequence homology to a viral polymerase selected from the group consisting of SARS-CoV polymerase, MERS-CoV polymerase and SARS-CoV-2. In some embodiments, the viral infection is caused by a virus having at least 80% sequence homology to a viral polymerase selected from the group consisting of SARS-CoV polymerase, MERS-CoV polymerase and SARS-CoV-2. In some embodiments, the viral infection is caused by a virus having at least 90% sequence homology to a viral polymerase selected from the group consisting of SARS-CoV polymerase, MERS-CoV polymerase and SARS-CoV-2. In some embodiments, the viral infection is caused by a virus having at least 95% sequence homology to a viral polymerase selected from the group consisting of SARS-CoV polymerase, MERS-CoV polymerase and SARS-CoV-2. In some embodiments, the viral infection is selected form the group consisting of 229E virus infection, NL63 virus infection, OC43 virus infection, and HKU1 virus infection. In some embodiments, the viral infection is SARS-CoV-2 infection (COVID-19). In some embodiments, the viral infection is a SARS-CoV virus infection. In some embodiments, the viral infection is a MERS-CoV virus infection. In some embodiments, the viral infection is a pneumoviridae virus infection. In some embodiments, the pneumoviridae virus infection is respiratory syncytial virus infection. In some embodiments, the pneumoviridae virus infection is human metapneumovirus infection. In some embodiments, the viral infection is a picornaviridae virus infection. In some embodiments, the viral infection is an enterovirus infection. In some embodiments, the viral infection is selected from the group consisting of Coxsackie A virus infection, Coxsackie A virus infection, enterovirus D68 infection, enterovirus B69 infection, enterovirus D70 infection, enterovirus A71 infection, and poliovirus infection. In some embodiments, the picornaviridae virus infection is human rhinovirus infection (HRV). In some embodiments, the picomaviridae virus infection is HRV-A, HRV-B, or HRV-C infection. In some embodiments, the viral infection is a flaviviridae virus infection. In some embodiments, the flaviviridae virus infection is a dengue virus infection, yellow fever virus infection, West Nile virus infection, tick borne encephalitis, Kunjin Japanese encephalitis, St. Louis encephalitis, Murray valley encephalitis, Omsk hemorrhagic fever, bovine viral diarrhea, zika virus infection, or a HCV infection. In some embodiments, the viral infection is a filoviridae virus infection. In some embodiments, the filoviridae virus infection is an ebola virus infection or a Marburg virus infection. In some embodiments, the viral infection is an orthomyxovirus infection. In some embodiments, the viral infection is an influenza virus infection. In some embodiments, the viral infection is an influenza A virus infection or influenza B virus infection. In some embodiments, the viral infection is a paramyxoviridae virus infection. In some embodiments, the viral infection is a human parainfluenza virus, Nipah virus, Hendra virus, measles, or mumps infection.

In one aspect, the disclosure provides a method for manufacturing a medicament for treating or preventing a viral infection in a human in need thereof, characterized in that a pharmaceutical formulation provided herein is used.

In one aspect, the disclosure provides a use of the pharmaceutical formulation provided herein for the manufacture of a medicament for the treatment or prevention of a viral infection in a human in need thereof. In some embodiments, the medicament is used with at least one additional therapeutic or prophylactic agent.

In one aspect, the disclosure provides a pharmaceutical formulation or a tablet disclosed herein for use in treatment or prevention of a viral infection in a human in need thereof. In some embodiments, the pharmaceutical formulation or the tablet for use with at least one additional therapeutic agent.

BRIEF DESCRIPTION OF DRAWINGS

FIG. 1 shows a flow diagram illustrating exemplary preparation of the solid oral dosage forms disclosed herein.

FIG. 2 shows the results of the stability studies carried out on exemplary formulations disclosed herein.

FIG. 3 shows the results of the stability studies carried out on exemplary formulations disclosed herein.

FIG. 4 shows results of stability studies carried out on Formulation 8.

FIG. 5 shows results of stability studies carried out on Formulation 8.

FIG. 6 shows results of stability studies carried out on Formulation 8.

DETAILED DESCRIPTION

Described herein are pharmaceutical formulations, in particular solid dosage forms (e.g., tablets and capsules) of the compound of Formula I.

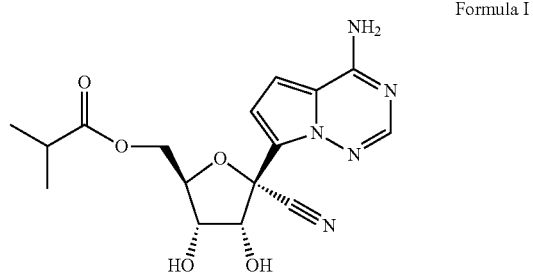 [SMILES: CC(C)C(=O)OC[C@H]1O[C@@](C#N)(c2ccc3c(N)ncnn23)[C@H](O)[C@@H]1O]

Formula I

The compound of Formula I was disclosed in WO 2022/047065 as Compound 15. The IUPAC name of the compound of Formula I is ((2R,3S,4R,5R)-5-(4-aminopyrrolo[2,1-f][1,2,4]triazin-7-yl)-5-cyano-3,4-dihydroxytetrahydrofuran-2-yl)methyl isobutyrate. Its CAS Registry Number is 2647441-36-7.

The compounds described herein, exemplified by Formula I, have chiral centers, e.g., chiral carbon. The pharmaceutical formulations, for example the solid oral dosage forms (e.g. tablets) disclosed herein thus include embodiments, where the compound having the chemical structure of Formula I is present as a racemic mixtures of all stereoisomers, including enantiomers, diastereomers, and atropisomers. In addition, the pharmaceutical formulations, for example the solid oral dosage forms (e.g., tablets) disclosed herein include embodiments wherein the compound of Formula I is enriched or resolved optical isomers at any or all asymmetric, chiral atoms. In other words, the chiral centers apparent from the depictions are provided as the chiral isomers or racemic mixtures. Pharmaceutical formulations, for example the solid oral dosage forms (e.g., tablets) comprising racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In some embodiments, the compound of Formula I is a substantially pure enantiomer.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compound of Formula I may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including compounds of Formula I, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The pharmaceutical formulations, for example the solid oral dosage forms (e.g., tablets) of disclosure also include embodiments, wherein the pharmaceutical formulations comprise compounds of the chemical structure of Formula I, but in which from 1 to n hydrogens attached to a carbon atom is/are replaced by deuterium, in which n is the number of hydrogens in the compound of Formula I. Such compounds may exhibit increased resistance to metabolism and are thus useful for increasing the half-life of the compound of Formula I when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium. As such, in some embodiments, the pharmaceutical formulations disclosed herein comprise the compound of

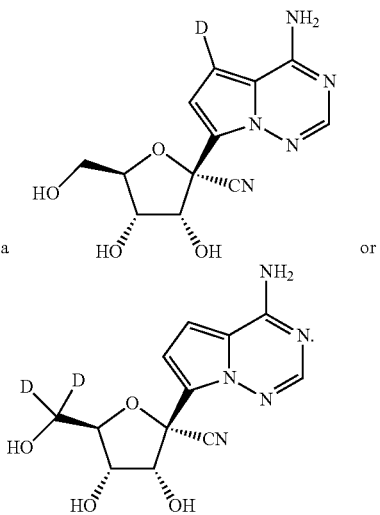

Formula or

Deuterium labeled or substituted therapeutic compounds used in the pharmaceutical formulations, for example solid oral dosage forms (e.g. tablets) disclosed herein may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The "X-ray powder diffraction pattern" or "XRPD pattern" as described herein preferably refers to the X-ray powder diffraction pattern obtained using CuKα radiation.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compositions may, in some embodiments, be administered to a subject (including a human) who is at risk or has a family history of the disease or condition.

As used herein the term "excipient" or "excipients" is intended to refer to inter alia basifying agents, solubilisers, glidants, fillers, binders, lubricant, diluents, preservatives, surface active agents, dispersing agents and the like. The term also comprises agents such as sweetening agents, flavoring agents, coloring agents, preserving agents, and coating agents. Such components will generally be present in admixture within the solid oral dosage forms (e.g., tablets).

As used herein, "mild renal impairment," used in reference to a patient, means that the patient has mild kidney damage. Mild renal impairment can also be referred to as "mild CKD." A patient can be classified as having mild renal impairment using known methods, such as determining an eGFR of the patient (e.g., using an equation suitable for the patient's population) and comparing the eGFR to suitable guidelines (e.g., current medical guidelines for a given eGFR calculation equation and/or patient population). For example, an eGFR of at least 60 mL/min/1.73 m² to less than 90 mL/min/1.73 m² can indicate mild renal impairment.

As used herein, "moderate renal impairment," used in reference to a patient, means that the patient has moderate kidney damage. Moderate renal impairment can also be referred to as "moderate CKD." A patient can be classified as having moderate renal impairment using known methods, such as determining an eGFR of the patient (e.g., using an equation suitable for the patient's population) and comparing the eGFR to suitable guidelines (e.g., current medical guidelines for a given eGFR calculation equation and/or patient population). For example, an eGFR of at least 30 mL/min/1.73 m² to less than 60 mL/min/1.73 m² can indicate moderate renal impairment.

As used herein, "severe renal impairment," used in reference to a patient, means that the patient has severe kidney damage. Severe renal impairment can also be referred to as "severe CKD." A patient can be classified as having severe renal impairment using known methods, such as determining an eGFR of the patient (e.g., using an equation suitable for the patient's population) and comparing the eGFR to suitable guidelines (e.g., current medical guidelines for a given eGFR calculation equation and/or patient population). For example, an eGFR of at least 15 mL/min/1.73 m² to less than 30 mL/min/1.73 m² can indicate severe renal impairment.

As used herein, "$d_n$" refers to particle size distribution by volume where n is between 0 and 100. For example, $d_{90}$ of less than 800 μm means 90% of the particles by volume are smaller than 800 μm.

PHARMACEUTICAL FORMULATIONS

All pharmaceutical formulations described here comprise the compound of Formula I, or a pharmaceutically acceptable salt thereof, and a pharmaceutically acceptable excipient. In some embodiments, the pharmaceutical formulations disclosed herein comprise the compound of Formula I, or a pharmaceutically acceptable salt thereof, and one or more components selected from a filler, a lubricant, and a disintegrating agent. In some embodiments, the pharmaceutical formulations disclosed herein comprise (i) the compound of Formula I, or a pharmaceutically acceptable salt thereof, (ii) a filler, (iii) a lubricant, and (iv) a disintegrating agent.

In some embodiments, the pharmaceutical formulations disclosed herein are a solid dosage form. The solid dosage form disclosed herein will include one or more excipients. Excipients should be compatible with the other ingredients of the formulation and physiologically innocuous to the recipient thereof. Examples of suitable excipients may be found e.g., in Handbook of Pharmaceutical Excipients (eds. Rowe, Sheskey & Quinn), 6th edition 2009.

The pharmaceutical formulations disclosed herein are for oral administration to a subject (for e.g., a human). As such, provided herein are solid dosage forms of the compound of Formula I for oral administration ("solid oral dosage forms"). In some embodiment, the solid oral dosage forms disclosed herein comprise one or more excipients selected from (i) a filler, (ii) a disintegrating agent, and (iii) a lubricant. In some embodiment, the solid oral dosage forms disclosed herein comprise (i) a filler, (ii) a disintegrating agent, and (iii) a lubricant.

Typically, pharmaceutical compositions may have desirable properties for medical or pharmaceutical use. Such properties include manufacturability (e.g., compressibility, ease of handling, ability to constantly prepare doses of the same strength, etc.), physical stability (e.g., thermal stability, shelf life, etc.), chemical stability, drug loading, dissolution rate (e.g., bioavailability) and process control. Thus, the present pharmaceutical compositions (e.g. tablets) may provide advantages such as improving the manufacturing process of the compound, improving the stability or storability of a drug product form of the compound, or improving drug loading of the compound.

The Compound of Formula I

The solid oral dosage forms disclosed herein may comprise any suitable amount of the compound of Formula I, for example about 0.1 mg to about 1000 mg of the compound of Formula I. In some embodiments, the solid oral dosage forms disclosed herein comprise about 10 mg to about 800 mg, about 10 mg to about 600 mg, about 10 mg to about 500 mg, about 10 mg to about 400 mg, about 10 mg to about 200 mg, about 10 mg to about 100 mg, about 10 mg to about 50 mg, about 10 mg to about 30 mg, about 50 mg to about 1000 mg, about 50 mg to about 800 mg, about 50 mg to about 600 mg, about 50 mg to about 400 mg, about 50 mg to about 200 mg, about 50 mg to about 100 mg, about 100 mg to about 1000 mg, about 100 mg to about 800 mg, about 100 mg to about 600 mg, about 100 mg to about 400 mg, about 100 mg to about 200 mg, about 200 mg to about 1000 mg, about 200 mg to about 800 mg, about 200 mg to about 600 mg, about 200 mg to about 400 mg, about 300 mg to about 1000 mg, about 300 mg to about 800 mg, about 300 mg to about 600 mg, about 300 mg to about 400 mg, about 400 mg to about 1000 mg, about 400 mg to about 800 mg, about 400 mg to about 600 mg, about 400 mg to about 500 mg, about 500 mg to about 1000 mg, about 500 mg to about 800 mg, about 500 mg to about 600 mg, about 600 mg to about 1000 mg, about 600 mg to about 900 mg, about 600 mg to about 800 mg, about 600 mg to about 700 mg, about 700 mg to about 1000 mg, about 700 mg to about 900 mg, about 700 mg to about 800 mg, about 800 mg to about 1000 mg, about 800 mg to about 900 mg, or about 900 mg to about 1000 mg of the compound of Formula I. In some embodiments, the solid oral dosage forms disclosed herein comprise about 50 to about 800 mg of the compound of Formula I. In some embodiments, the solid oral dosage forms disclosed herein comprise about 100 to about 700 mg of the compound of Formula I, for example from about 100 mg, about 350 mg, about 500 mg, or about 700 mg of the compound of Formula I. In some embodiments, the solid oral dosage forms disclosed herein comprise about 100 mg of the compound of Formula I. In some embodiments, the solid oral dosage forms disclosed herein comprise about 350 mg of the compound of Formula I. In some embodiments, the solid oral dosage forms disclosed herein comprise about 500 mg of the compound of Formula I. In some embodiments, the solid oral dosage forms disclosed herein comprise about 700 mg of the compound of Formula I. In some embodiments, the solid oral dosage forms disclosed herein comprise about 175 mg of the compound of Formula I.

The solid oral dosage forms disclosed herein may comprise any suitable amount of the compound of Formula I, for example about 1 mg to about 1000 mg of the compound of Formula I.

The compound of Formula I can be used in any suitable form. For example, the compound of Formula I can be amorphous or crystalline. In some embodiments, the compound of Formula I is amorphous. In some embodiments, the compound of Formula I is crystalline. In some embodiments, the compound of Formula I is the freebase form.

Crystalline forms of the compound of Formula I useful in the formulations and methods of the present disclosure are described for example in International Patent Application Publication No. WO 2022/047065. For example, the compound of Formula I can be crystalline freebase Form I, freebase Form II, freebase Form III, xinafoate material A, HCl salt Form I, HCl salt material A, HCl salt material B, HCl salt material C as described in WO 2022/047065, or a combination thereof. In some embodiments, the compound of Formula I is crystalline. Unless specifically mentioned otherwise, when a pharmaceutically acceptable salt of the compound of Formula I is used in the pharmaceutical formulations described herein, the % wt of Formula I would be adjusted accordingly based on salt correction factor.

The salt correction factor is calculated by taking the molar mass of the pharmaceutically acceptable salt of the compound of Formula I and dividing it by the molar mass of the freebase form of the compound of Formula I. For example, for the hydrochloride salt of the compound of Formula I, the salt correction factor is 1.10. Therefore, the % wt of the hydrochloride salt of Formula I will be 1.10 multiplied by the % wt specified for the compound of Formula I.

In some embodiments, the compound of Formula I is crystalline freebase Form III as described in International Patent Application Publication No. WO 2022/047065. In some embodiments, crystalline compound of Formula I is characterized by an X-ray powder diffraction (XRPD) pattern comprising degree 2θ-reflections (+/−0.2 degrees 2θ) at 9.8°, 16.0°, and 25.4°. In some embodiments, crystalline compound of Formula I has an XRPD pattern comprising degree 2θ-reflections (+/−0.2 degrees 2θ) at 9.8°, 16.0°, and 25.4°, and one, two or three of the degree 2θ-reflections (+/−0.2 degrees 2θ) at 10.2°, 19.1°, and 26.9°. In some embodiments, crystalline compound of Formula I has an XRPD pattern comprising degree 2θ-reflections (+/−0.2 degrees 2θ) at 9.8°, 16.0°, and 25.4°, and one or two of the degree 2θ-reflections (+/−0.2 degrees 2θ) at 10.2°, 19.1°, and 26.9°. In some embodiments, crystalline compound of Formula I has an XRPD pattern comprising degree 2θ-reflections (+/−0.2 degrees 2θ) at 9.8°, 16.0°, and 25.4°, and one of the degree 2θ-reflections (+/−0.2 degrees 2θ) at 10.2°, 19.1°, and 26.9°. In some embodiments, crystalline compound of Formula I has an XRPD pattern comprising degree 2θ-reflections (+/−0.2 degrees 2θ) at 9.8°, 16.0°, and 25.4°, and two of the degree 2θ-reflections (+/−0.2 degrees 2θ) at 10.2°, 19.1°, and 26.9°. In some embodiments, crystalline compound of Formula I has an XRPD pattern comprising degree 2θ-reflections (+/−0.2 degrees 2θ) at 9.8°, 10.2°, 16.0°, 19.1°, 25.4°, and 26.9°. In some embodiments, crystalline compound of Formula I has an XRPD pattern comprising any three of the degree 2θ-reflections (+/−0.2 degrees 2θ) at 9.8°, 10.2°, 16.0°, 19.1°, 25.4°, and 26.9°.

In some embodiments, crystalline compound of Formula I has an XRPD pattern comprising degree 2θ-reflections (+/−0.2 degrees 2θ) at 9.8°, 10.2°, 16.0°, 19.10, 25.4°, and 26.9°, and one, two or three of the degree 2θ-reflections (+/−0.2 degrees 2θ) at 10.4°, 19.8°, and 20.7°. In some embodiments, crystalline compound of Formula I has an XRPD pattern comprising degree 2θ-reflections (+/−0.2 degrees 2θ) at 9.8°, 10.2°, 16.0°, 19.10, 25.4°, and 26.9°, and one or two of the degree 2θ-reflections (+/−0.2 degrees 2θ) at 10.4°, 19.8°, and 20.7°. In some embodiments, crystalline compound of Formula I has an XRPD pattern comprising degree 2θ-reflections (+/−0.2 degrees 2θ) at 9.8°, 10.2°, 16.0°, 19.10, 25.4°, and 26.9°, and one of the degree 2θ-reflections (+/−0.2 degrees 2θ) at 10.4°, 19.8°, and 20.7°. In some embodiments, crystalline compound of Formula I has an XRPD pattern comprising degree 2θ-reflections (+/−0.2 degrees 2θ) at 9.8°, 10.2°, 16.0°, 19.1°, 25.4°, and 26.9°, and two of the degree 2θ-reflections (+/−0.2 degrees 2θ) at 10.4°, 19.8°, and 20.7°. In some embodiments, crystalline compound of Formula I has an XRPD pattern comprising degree 2θ-reflections (+/−0.2 degrees 2θ) at 9.8°, 10.2°, 10.4°, 16.0°, 19.1°, 19.8°, 20.7°, 25.4°, and 26.9°. In some embodiments, crystalline compound of Formula I has an XRPD pattern comprising any three of the degree 2θ-reflections (+/−0.2 degrees 2θ) at 9.8°, 10.2°, 10.4°, 16.0°, 19.1°, 19.8°, 20.7°, 25.4°, and 26.9°.

The compound of Formula I can have any suitable purity. For example, the compound of Formula I can have a purity of at least about 90%, or at least about 91%, about 92%, about 93%, about 94%, about 95%, about 96%, about 97%, about 98%, about 99%, or at least about 99.1%, about 99.2%, about 99.3%, about 99.4%, about 99.5%, about 99.6%, about 99.7%, about 99.8% or at least about 99.9%. In some embodiments, the compound of Formula I has a purity of at least about 99.10%. In some embodiments, the compound of Formula I has a purity of at least about 99.3%.

In some embodiments, the compound of Formula I has a purity of at least about 99.5%. In some embodiments, the compound of Formula I has a purity of at least about 99.7%. In some embodiments, the compound of Formula I has a purity of at least about 99.5%. In some embodiments, the compound of Formula I has a purity of at least about 99.9%.

In some embodiments, the compound of Formula I has a $d_{90}$ of less than about 800 µm. For example, the form has a $d_{90}$ of less than about 750 µm, about 700 µm, about 650 µm, about 600 µm, about 550 µm, about 500 µm, about 450 µm, about 400 µm, about 350 µm, about 300 µm, about 250 µm, about 200 µm, about 150 µm, about 100 µm, about 50 µm, about 40 µm, about 30 µm, about 20 µm or about 10 µm. In some embodiments, the form has a $d_{90}$ of about 10 µm-500 µm, for example, about 10 µm-450 µm, about 10 µm-400 µm, about 10 µm-350 µm, about 10 µm-300 µm, about 10 µm-250 µm, about 10 µm-200 µm, about 10 µm-150 µm, about 10 µm-100 µm, about 40 µm-800 µm, about 40 µm-750 µm, about 40 µm-700 µm, about 40 µm-650 µm, about 40 µm-600 µm, about 40 µm-550 µm, about 40 µm-500 µm, about 40 µm-450 µm, about 40 µm-400 µm, about 40 µm-350 µm, about 40 µm-300 µm, about 40 µm-250 µm, about 40 µm-200 µm, about 40 µm-150 µm, or about 40 µm-100 µm. In some embodiments, the form has a $d_{90}$ of about 10 µm-500 µm, for example about 40 µm-500 µm, or about 100 µm-500 µm.

In some embodiments, the compound of Formula I has a $d_{50}$ of less than about 300 µm. For example, the compound of Formula I has a $d_{50}$ of less than about 250 µm, about 200 µm, about 150 µm, about 100 µm, about 90 µm, about 80 µm, about 70 µm, about 60 µm, about 50 µm, about 40 µm, about 35 µm, about 30 µm, about 25 µm, about 20 µm, about 15 µm, about 10 µm, about 9 µm, about 8 µm, about 7 µm, about 6 µm, about 5 µm, about 4 µm, about 3 µm, about 2 µm, or about 1 µm. In some embodiments, the compound of Formula I has a $d_{50}$ of about 0.1 µm-300 µm. In some embodiments, the form has a $d_{50}$ of about 1 µm-300 µm. In some embodiments, the compound of Formula I has a $d_{50}$ of about 10 µm-300 µm. In some embodiments, the form has a $d_{50}$ of about 10 µm-2500 µm.

In some embodiments, the compound of Formula I form has a $d_{10}$ of less than about 100 µm. For example, the compound of Formula I has a $d_{10}$ of less than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 9 µm, 8 µm, 7 µm, 6 µm, 5 µm, 4 µm, 3 µm, 2 µm, or 1 µm, 0.5 µm, 0.4 µm, 0.3 µm, 0.2 µm, or 0.1 µm. In some embodiments, the form has a $d_{10}$ of about 0.1 µm-90 µm, for example, about 1 µm-90 µm, 1 µm-80 µm, 1 µm-70 µm, 1 µm-60 µm, 1 µm-50 µm, 1 µm-40 µm, 1 µm-30 µm, about 1 µm-20 µm, 1 µm-15 µm, 1 µm-10 µm, 1 µm-9 µm, 1 µm-8 µm, 1 µm-7 µm, 1 µm-6 µm, 1 µm-5 µm, 1 µm-4 µm, 1 µm-3 µm, 1 µm-2 µm, 0.1 µm-15 µm, 0.1 µm-10 µm, 0.1 µm-9 µm, 0.1 µm-8 µm, 0.1 µm-7 µm, 0.1 µm-6 µm, 0.1 µm-5 µm, 0.1 µm-4 µm, 0.1 µm-3 µm, 0.1 µm-2 µm, or 0.1 µm-1 µm. In some embodiments, the form has a $d_{10}$ of about 1 µm-60 µm.

In some embodiments, the compound of Formula I is micronized.

Lubricant

Examples of lubricants that can be used in the solid oral dosage forms disclosed herein include, but are not limited to, magnesium stearate, calcium stearate, stearic acid, hydrogenated vegetable oil, glyceryl palmitostearate, glyceryl behenate, sodium stearyl fumarate, colloidal silicon dioxide, carnauba wax, polyethylene glycol, and talc powder. In some embodiments, the lubricant is selected from the group consisting of stearic acid, sodium stearyl fumarate, magnesium stearate, and combinations thereof. In some embodiments, the lubricant is stearic acid. In some embodiments, the lubricant is sodium stearyl fumarate. In some embodiments, the lubricant is magnesium stearate.

The amount of lubricant in the solid oral dosage forms disclosed herein is generally between about 0.5 to about 5% by weight. In some embodiments, the amount of lubricant is about 0.5 to about 4.5% by weight. In some embodiments, the amount of lubricant is about 0.5 to about 4.0% by weight. In some embodiments, the amount of lubricant is about 0.5 to about 3.5% by weight. In some embodiments, the amount of lubricant is about 0.5 to about 3.0% by weight. In some embodiments, the amount of lubricant is about 0.5 to about 2.5% by weight. In some embodiments, the amount of lubricant is about 0.5 to about 2.0% by weight. In some embodiments, the amount of lubricant is about 0.5% by weight. In some embodiments, the amount of lubricant is about 1.0% by weight. In some embodiments, the amount of lubricant is about 1.5% by weight. In some embodiments, the amount of lubricant is about 2% by weight. In some embodiments, the amount of lubricant is about 2.5% by weight. In some embodiments, the amount of lubricant is about 3.0% by weight. In some embodiments, the amount of lubricant is about 3.5% by weight. In some embodiments, the amount of lubricant is about 4.0% by weight. In some embodiments, the amount of lubricant is about 4.5% by weight. In some embodiments, the amount of lubricant is about 5.0% by weight. In some embodiments, the amount of lubricant in a tablet is about 1.0% to about 1.5% by weight. In some embodiments, the amount of lubricant in a tablet is about 1.0% by weight. In some embodiments, the amount of lubricant in a tablet is about 1.5% by weight.

In some embodiments, the solid oral dosage form comprises less than about 100 mg of lubricant. For example, the solid oral dosage form comprises about 90 mg, about 80 mg, about 70 mg, about 60 mg, about 50 mg, less than about 40 mg, less than about 30 mg, less than about 20 mg, less than about 15 mg, or less than about 10 mg of lubricant. In some embodiments, the solid oral dosage form comprises about 1 mg to about 100 mg, about 1 mg to about 90 mg, about 1 mg to about 80 mg, about 1 mg to about 70 mg of lubricant, or about 1 mg to about 60 mg of lubricant. In some embodiments, the solid oral dosage form comprises about 1 mg to about 50 mg of lubricant, about 1 mg to about 40 mg, 1 mg to about 30 mg, 1 mg to about 20 mg, or about 1 mg to about 10 mg of lubricant. In some embodiments, the tablet comprises about 1 mg to about 20 mg lubricant.

In some embodiments, the solid oral dosage forms disclosed herein comprise magnesium stearate. In some embodiments, the amount of magnesium stearate in a solid oral dosage form is about 1.0% to about 1.5% by weight. In some embodiments, the amount of magnesium stearate in a solid oral dosage form is about 1.0% by weight. In some embodiments, the amount of magnesium stearate in a solid oral dosage form is about 1.5% by weight. In some embodiments, the solid oral dosage form comprises less than about 50 mg, less than about 40 mg, less than about 30 mg, less than about 20 mg, less than about 15 mg, or less than about 10 mg magnesium stearate. In some embodiments, the solid oral dosage form comprises about 1 mg to about 50 mg lubricant, or about 1 mg to about 40 mg, 1 mg to about 30 mg, 1 mg to about 20 mg, or 1 mg to about 10 mg of magnesium stearate. In some embodiments, the solid oral dosage form comprises about 1 mg to about 20 mg magnesium stearate.

In some embodiments, the solid oral dosage form comprises 100 mg of the compound of Formula I and about 0.5 mg to about 5 mg of the lubricant. In some embodiments, the solid oral dosage form comprises about 100 mg of the compound of Formula I and about 0.5 mg to about 5 mg of the lubricant. In some embodiments, the solid oral dosage form comprises about 100 mg of the compound of Formula I and about 1 to about 4 mg of the lubricant. In some embodiments, the solid oral dosage form comprises about 100 mg of the compound of Formula I and about 3 mg of the lubricant. In some embodiments, the lubricant is magnesium stearate. In some embodiments, the solid oral dosage form is a tablet.

In some embodiments, the solid oral dosage form comprises about 350 mg of the compound of Formula I and about 1.8 mg to about 18 mg of the lubricant. In some embodiments, the solid oral dosage form comprises about 350 mg of the compound of Formula I and about 5 mg to about 10 mg of the lubricant. In some embodiments, the solid oral dosage form comprises about 350 mg of the compound of Formula I and about 6 mg to about 8 mg of the lubricant. In some embodiments, the solid oral dosage form comprises about 350 mg of the compound of Formula I and about 7 mg of the lubricant. In some embodiments, the lubricant is magnesium stearate. In some embodiments, the solid oral dosage form is a tablet.

In some embodiments, the solid oral dosage form comprises about 500 mg of the compound of Formula I and about 2.5 mg to about 25 mg of the lubricant. In some embodiments, the solid oral dosage form comprises about 500 mg of the compound of Formula I and about 5 mg to about 15 mg of the lubricant. In some embodiments, the solid oral dosage form comprises about 500 mg of the compound of Formula I and about 1 to about 8 mg to about 12 mg of the lubricant. In some embodiments, the solid oral dosage form comprises about 500 mg of the compound of Formula I and about 10 mg of the lubricant. In some embodiments, the lubricant is magnesium stearate. In some embodiments, the solid oral dosage form is a tablet.

In some embodiments, the solid oral dosage form comprises about 700 mg of the compound of Formula I and about 3.6 mg to about 36 mg of the lubricant. In some embodiments, the solid oral dosage form comprises about 700 mg of the compound of Formula I and about 10 mg to about 20 mg of the lubricant. In some embodiments, the solid oral dosage form comprises about 700 mg of the compound of Formula I and about 12 mg to about 16 mg of the lubricant. In some embodiments, the solid oral dosage form comprises about 700 mg of the compound of Formula I and about 14 mg of the lubricant. In some embodiments, the lubricant is magnesium stearate. In some embodiments, the solid oral dosage form is a tablet.

In some embodiments, the solid oral dosage form comprises 175 mg of the compound of Formula I and about 0.5 mg to about 5 mg of the lubricant. In some embodiments, the solid oral dosage form comprises about 175 mg of the compound of Formula I and about 2 to about 4 mg of the lubricant. In some embodiments, the solid oral dosage form comprises about 175 mg of the compound of Formula I and about 3.5 mg of the lubricant. In some embodiments, the lubricant is magnesium stearate. In some embodiments, the solid oral dosage form is a tablet.

Disintegrating Agent (Disintegrant)

Examples of disintegrating agents that can be used in the solid oral dosage forms described herein include, but are not limited to, starches, pre-gelatinized starch, hydroxypropyl starch, celluloses (e.g., microcrystalline cellulose and low substituted hydroxypropyl cellulose), cross-linked PVP (crospovidone), sodium starch glycolate, croscarmellose sodium, etc. In some embodiments, the disintegrating agent is croscarmellose sodium. In some embodiments, the disintegrating agent is starch. In some embodiments, the disintegrating agent is pre-gelatinized starch. In some embodiments, the disintegrating agent is cellulose. In some embodiments, the disintegrating agent is microcrystalline cellulose. In some embodiments, the disintegrating agent is low substituted hydroxypropyl cellulose. In some embodiments, the disintegrating agent is cross-linked PVP (crospovidone). In some embodiments, the disintegrating agent is sodium starch glycolate. In some embodiments, the disintegrating agent is croscarmellose sodium.

In some embodiments, the lubricant is magnesium stearate and the disintegrating agent is crospovidone.

In some embodiments, the disintegrating agent is Polyplasdone™ xl-10 crospovidone.

In some embodiments, the amount of disintegrating agent in a solid oral dosage form is about 1% to about 10% by weight. In some embodiments, the amount of disintegrating agent in a tablet is about 10% to about 9%, about 10% to about 8%, about 10% to about 7%, about 10% to about 6%, about 10% to about 5%, about 10% to about 4%, about 10% to about 3%, about 10% to about 2%, about 2% to about 10%, 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% by weight. In some embodiments, the amount of disintegrating agent in a solid oral dosage forms is about 3% to about 5% by weight.

In some embodiments, the solid oral dosage form comprises about 5 mg to about 200 mg of disintegrating agent. In some embodiments, the solid oral dosage form comprises about 5 mg to about 190 mg, 5 mg to about 180 mg, 5 mg to about 170 mg, 5 mg to about 160 mg, 5 mg to about 150 mg, 5 mg to about 140 mg, 5 mg to about 130 mg, 5 mg to about 120 mg, 5 mg to about 110 mg, 5 mg to about 100 mg, 5 mg to about 90 mg, 5 mg to about 80 mg, 5 mg to about 70 mg, 5 mg to about 60 mg, 5 mg to about 50 mg, 5 mg to about 40 mg, about 5 mg to about 30 mg, about 5 mg to about 20 mg, about 5 mg to about 10 mg, about 10 mg to about 50 mg, about 10 mg to about 40 mg, about 10 mg to about 30 mg, about 10 mg to about 20 mg, about 20 mg to about 50 mg, about 20 mg to about 40 mg, about 20 mg to about 30 mg, about 30 mg to about 50 mg, or about 30 mg to about 40 mg of disintegrating agent. In some embodiments, the solid oral dosage form comprises about 5 mg to about 50 mg of disintegrating agent. In some embodiments, the solid oral dosage form comprises about 40 mg to about 50 mg of disintegrating agent.

In some embodiments, the disintegrating agent is crospovidone. In some embodiments, the amount of crospovidone in a solid oral dosage form is about 1% to about 10% by weight. In some embodiments, the amount of crospovidone in a solid oral dosage form is about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% by weight. In some embodiments, the amount of crospovidone in a solid oral dosage form is about 3% to about 5%. In some embodiments, solid oral dosage form is a tablet.

In some embodiments, the solid oral dosage form comprises about 5 mg to about 50 mg of crospovidone. In some embodiments, the solid oral dosage form comprises about 5 mg to about 40 mg, about 5 mg to about 30 mg, about 5 mg to about 20 mg, about 5 mg to about 10 mg, about 10 mg to about 50 mg, about 10 mg to about 40 mg, about 10 mg to about 30 mg, about 10 mg to about 20 mg, about 20 mg to about 50 mg, about 20 mg to about 40 mg, about 20 mg to about 30 mg, about 30 mg to about 50 mg, about 30 mg to about 40 mg, or about 40 mg to about 50 mg of crospovidone. In some embodiments, solid oral dosage form is a tablet.

In some embodiments, the solid oral dosage form comprises about 100 mg of the compound of Formula I and about 1 to about 10 mg of the disintegrating agent. In some embodiments, the solid oral dosage form comprises about 100 mg of the compound of Formula I and about 5 to about 10 mg of the disintegrating agent. In some embodiments, the solid oral dosage form comprises about 100 mg of the compound of Formula I and about 8 mg of the disintegrating agent. In some embodiments, the solid oral dosage form comprises about 100 mg of the compound of Formula I and about 1 to about 10 mg of crospovidone. In some embodiments, the solid oral dosage form comprises about 100 mg of the compound of Formula I and about 5 to about 10 mg of crospovidone. In some embodiments, the solid oral dosage form comprises about 100 mg of the compound of Formula I and about 8 mg of crospovidone. In some embodiments, solid oral dosage form is a tablet.

In some embodiments, the solid oral dosage form comprises about 500 mg of the compound of Formula I and about 5 to about 50 mg of the disintegrating agent. In some embodiments, the solid oral dosage form comprises about 500 mg of the compound of Formula I and about 25 to about 50 mg of the disintegrating agent. In some embodiments, the solid oral dosage form comprises about 500 mg of the compound of Formula I and about 40 mg of the disintegrating agent. In some embodiments, the solid oral dosage form comprises about 500 mg of the compound of Formula I and about 5 to about 50 mg of crospovidone. In some embodiments, the solid oral dosage form comprises about 500 mg of the compound of Formula I and about 25 to about 50 mg of crospovidone. In some embodiments, the solid oral dosage form comprises about 500 mg of the compound of Formula I and about 40 mg of crospovidone. In some embodiments, solid oral dosage form is a tablet.

In some embodiments, the solid oral dosage form comprises about 350 mg of the compound of Formula I and about 3.5 to about 35 mg of the disintegrating agent. In some embodiments, the solid oral dosage form comprises about 350 mg of the compound of Formula I and about 18 to about 35 mg of the disintegrating agent. In some embodiments, the solid oral dosage form comprises 350 mg of the compound of Formula I and about 28 mg of the disintegrating agent. In some embodiments, the solid oral dosage form comprises about 350 mg of the compound of Formula I and about 3.5 to about 35 mg of crospovidone. In some embodiments, the solid oral dosage form comprises about 350 mg of the compound of Formula I and about 18 to about 35 mg of crospovidone. In some embodiments, the solid oral dosage form comprises about 350 mg of the compound of Formula I and about 28 mg of crospovidone. In some embodiments, solid oral dosage form is a tablet. In some embodiments, the solid oral dosage form comprises about 700 mg of the compound of Formula I and about 7 to about 70 mg of the disintegrating agent. In some embodiments, the solid oral dosage form comprises about 700 mg of the compound of Formula I and about 36 to about 70 mg of the disintegrating agent. In some embodiments, the solid oral dosage form comprises 700 mg of the compound of Formula I and about 56 mg of the disintegrating agent.

In some embodiments, the solid oral dosage form comprises about 700 mg of the compound of Formula I and about 7 to about 70 mg of crospovidone. In some embodiments, the solid oral dosage form comprises about 700 mg of the compound of Formula I and about 36 to about 70 mg of crospovidone. In some embodiments, the solid oral dosage form comprises about 700 mg of the compound of Formula I and about 56 mg of crospovidone. In some embodiments, solid oral dosage form is a tablet.

In some embodiments, the solid oral dosage form comprises about 175 mg of the compound of Formula I and about 2 to about 18 mg of the disintegrating agent. In some embodiments, the solid oral dosage form comprises about 175 mg of the compound of Formula I and about 9 to about 18 mg of the disintegrating agent. In some embodiments, the solid oral dosage form comprises 175 mg of the compound of Formula I and about 14 mg of the disintegrating agent.

In some embodiments, the solid oral dosage form comprises about 175 mg of the compound of Formula I and about 2 to about 18 mg of crospovidone. In some embodiments, the solid oral dosage form comprises about 175 mg of the compound of Formula I and about 9 to about 18 mg of crospovidone. In some embodiments, the solid oral dosage form comprises about 175 mg of the compound of Formula I and about 14 mg of crospovidone. In some embodiments, solid oral dosage form is a tablet.

Filler

Examples of fillers (also known as bulking agents or diluents) that can be used in the solid oral dosage forms disclosed herein include, but are not limited to, starches, maltodextrins, polyols (such as lactose), and celluloses. In some embodiments, the filler is microcrystalline cellulose. In some embodiments, the filler is lactose. In some embodiments, the filler is mannitol. In some embodiments, the filler is dicalcium phosphate.

In some embodiments, the amount of filler in a solid oral dosage form is about 20% to about 60% by weight. some embodiments, the amount of filler in a solid oral dosage form is about 20% to about 50%, about 20% to about 40%, about 20% to about 30%, about 30% to about 60% by weight, about 30% to about 50%, about 30% to about 40%, about 40% to about 60%, or about 40% to about 50% by weight.

In some embodiments, the amount of filler in a solid oral dosage form is about 40% to about 50% by weight. In some embodiments, the amount of filler in a solid oral dosage form is about 40% to about 48%, about 40% to about 46%, about 40% to about 44%, about 40% to about 42%, about 42% to about 50%, about 42% to about 48%, about 42% to about 46%, about 42% to about 44%, about 44% to about 50%, about 44% to about 48%, about 44% to about 46%, about 46% to about 50%, about 46% to about 48%, or about 48% to about 50%. In some embodiments, the amount of filler in a solid oral dosage form is about 44% to about 46% by weight.

In some embodiments, the amount of filler in a solid oral dosage form is about 50 mg to about 1000 mg. In some embodiments, the amount of filler in a solid oral dosage form is about 50 mg to about 950 mg, about 50 mg to about 900 mg, about 50 mg to about 850 mg, about 50 mg to about 800 mg, about 50 mg to about 750 mg, about 50 mg to about 700 mg, about 50 mg to about 650 mg, about 50 mg to about 600 mg, about 50 mg to about 550 mg, about 50 mg to about 500 mg, about 50 mg to about 450 mg, about 50 mg to about 400 mg, about 50 mg to about 350 mg, about 50 mg to about 300 mg, about 50 mg to about 250 mg, about 50 mg to about 200 mg, about 50 mg to about 150 mg, about 50 mg to about 100 mg, about 100 mg to about 500 mg, about 100 mg to about 450 mg, about 100 mg to about 400 mg, about 100 mg to about 350 mg, about 100 mg to about 300 mg, about 100 mg to about 250 mg, about 100 mg to about 200 mg, about 100 mg to about 150 mg, about 150 mg to about 500 mg, about 150 mg to about 450 mg, about 150 mg to about 400 mg, about 150 mg to about 350 mg, about 150 mg to about 300 mg, about 150 mg to about 250 mg, about 150 mg to about 200 mg, about 200 mg to about 500 mg, about 200 mg to about 450 mg, about 200 mg to about 400 mg, about 200 mg to about 350 mg, about 200 mg to about 300 mg, about 200 mg to about 250 mg, about 250 mg to about 500 mg, about 250 mg to about 450 mg, about 250 mg to about 400 mg, about 250 mg to about 350 mg, about 250 mg to about 300 mg, about 300 mg to about 500 mg, about 300 mg to about 450 mg, about 300 mg to about 400 mg, about 300 mg to about 350 mg, about 350 mg to about 500 mg, about 350 mg to about 450 mg, about 350 mg to about 400 mg, about 400 mg to about 500 mg, about 400 mg to about 450 mg, or about 450 mg to about 500 mg. In some embodiments, the amount of filler in a solid oral dosage form is about 50 mg to about 500 mg.

In some embodiments, the filler is microcrystalline cellulose. In some embodiments, the amount of microcrystalline cellulose in a solid dosage form is about 40% to about 50% by weight. In some embodiments, the amount of microcrystalline cellulose in a solid dosage form is about 40% to about 48%, about 40% to about 46%, about 40% to about 44%, about 40% to about 42%, about 42% to about 50%, about 42% to about 48%, about 42% to about 46%, about 42% to about 44%, about 44% to about 50%, about 44% to about 48%, about 44% to about 46%, about 46% to about 50%, about 46% to about 48%, or about 48% to about 50%. In some embodiments, the amount of microcrystalline cellulose in a solid dosage form is about 44% to about 46% by weight.

In some embodiments, the amount of microcrystalline cellulose in a solid dosage form is about 50 mg to about 1000 mg. In some embodiments, the amount of microcrystalline cellulose in a solid dosage form is about 50 mg to about 950 mg, about 50 mg to about 900 mg, about 50 mg to about 850 mg, about 50 mg to about 800 mg, about 50 mg to about 750 mg, about 50 mg to about 700 mg, about 50 mg to about 650 mg, about 50 mg to about 600 mg, about 50 mg to about 550 mg, about 50 mg to about 500 mg, 50 mg to about 450 mg, about 50 mg to about 400 mg, about 50 mg to about 350 mg, about 50 mg to about 300 mg, about 50 mg to about 250 mg, about 50 mg to about 200 mg, about 50 mg to about 150 mg, about 50 mg to about 100 mg, about 100 mg to about 500 mg, about 100 mg to about 450 mg, about 100 mg to about 400 mg, about 100 mg to about 350 mg, about 100 mg to about 300 mg, about 100 mg to about 250 mg, about 100 mg to about 200 mg, about 100 mg to about 150 mg, about 150 mg to about 500 mg, about 150 mg to about 450 mg, about 150 mg to about 400 mg, about 150 mg to about 350 mg, about 150 mg to about 300 mg, about 150 mg to about 250 mg, about 150 mg to about 200 mg, about 200 mg to about 500 mg, about 200 mg to about 450 mg, about 200 mg to about 400 mg, about 200 mg to about 350 mg, about 200 mg to about 300 mg, about 200 mg to about 250 mg, about 250 mg to about 500 mg, about 250 mg to about 450 mg, about 250 mg to about 400 mg, about 250 mg to about 350 mg, about 250 mg to about 300 mg, about 300 mg to about 500 mg, about 300 mg to about 450 mg, about 300 mg to about 400 mg, about 300 mg to about 350 mg, about 350 mg to about 500 mg, about 350 mg to about 450 mg, about 350 mg to about 400 mg, about 400 mg to about 500 mg, about 400 mg to about 450 mg, about 450 mg to about 500 mg. In some embodiments, the amount of microcrystalline cellulose in a solid dosage form is about 50 mg to about 500 mg.

In some embodiments, the solid dosage form comprises about 100 mg of the compound of Formula I and about 40 mg to about 120 mg of the filler. In some embodiments, the solid dosage form comprises about 100 mg of the compound of Formula I and about 80 mg to about 100 mg of the filler. In some embodiments, the solid dosage form comprises about 100 mg of the compound of Formula I and about 85 mg to about 95 mg of the filler. In some embodiments, the solid dosage form comprises about 100 mg of the compound of Formula I and about 89 mg of the filler. In some embodiments, the solid dosage form is a tablet.

In some embodiments, the solid dosage form comprises about 500 mg of the compound of Formula I and about 200 mg to about 600 mg of the filler. In some embodiments, the solid dosage form comprises about 500 mg of the compound of Formula I and about 400 mg to about 500 mg of the filler. In some embodiments, the solid dosage form comprises about 500 mg of the compound of Formula I and about 425 mg to about 475 mg of the filler. In some embodiments, the solid dosage form comprises about 500 mg of the compound of Formula I and about 450 mg of the filler. In some embodiments, the solid dosage form is a tablet.

In some embodiments, the solid dosage form comprises about 350 mg of the compound of Formula I and about 140 mg to about 420 mg of the filler. In some embodiments, the solid dosage form comprises about 350 mg of the compound of Formula I and about 280 mg to about 350 mg of the filler. In some embodiments, the solid dosage form comprises about 350 mg of the compound of Formula I and about 298 mg to about 333 mg of the filler. In some embodiments, the solid dosage form comprises about 350 mg of the compound of Formula I and about 315 mg of the filler. In some embodiments, the solid dosage form is a tablet.

In some embodiments, the solid dosage form comprises about 175 mg of the compound of Formula I and about 70 mg to about 210 mg of the filler. In some embodiments, the solid dosage form comprises about 175 mg of the compound of Formula I and about 140 mg to about 175 mg of the filler. In some embodiments, the solid dosage form comprises about 175 mg of the compound of Formula I and about 149 mg to about 167 mg of the filler. In some embodiments, the solid dosage form comprises about 175 mg of the compound of Formula I and about 157.5 mg of the filler. In some embodiments, the solid dosage form is a tablet.

In some embodiments, the solid dosage form comprises about 700 mg of the compound of Formula I and about 280 mg to about 840 mg of the filler. In some embodiments, the solid dosage form comprises about 700 mg of the compound of Formula I and about 560 mg to about 700 mg of the filler. In some embodiments, the solid dosage form comprises about 700 mg of the compound of Formula I and about 600 mg to about 670 mg of the filler. In some embodiments, the solid dosage form comprises about 700 mg of the compound of Formula I and about 630 mg of the filler. In some embodiments, the solid dosage form is a tablet.

In some embodiments, the filler is microcrystalline cellulose. In some embodiments, the solid dosage form comprises about 100 mg of the compound of Formula I and about 40 mg to about 120 mg of microcrystalline cellulose. In some embodiments, the solid dosage form comprises about 100 mg of the compound of Formula I and about 80 mg to about 100 mg of microcrystalline cellulose. In some embodiments, the solid dosage form comprises about 100 mg of the compound of Formula I and about 85 mg to about 95 mg of microcrystalline cellulose. In some embodiments, the solid dosage form comprises about 100 mg of the compound of Formula I and about 89 mg of microcrystalline cellulose. In some embodiments, the solid dosage form is a tablet.

In some embodiments, the solid dosage form comprises about 500 mg of the compound of Formula I and about 200 mg to about 600 mg of microcrystalline cellulose. In some embodiments, the solid dosage form comprises about 500 mg of the compound of Formula I and about 400 mg to about 500 mg of microcrystalline cellulose. In some embodiments, the solid dosage form comprises about 500 mg of the compound of Formula I and about 425 mg to about 475 mg of microcrystalline cellulose. In some embodiments, the solid dosage form comprises about 500 mg of the compound of Formula I and about 450 mg of microcrystalline cellulose. In some embodiments, the solid dosage form is a tablet.

In some embodiments, the solid dosage form comprises about 350 mg of the compound of Formula I and about 140 mg to about 420 mg of microcrystalline cellulose. In some embodiments, the solid dosage form comprises about 350 mg of the compound of Formula I and about 280 mg to about 350 mg of microcrystalline cellulose. In some embodiments, the solid dosage form comprises about 350 mg of the compound of Formula I and about 298 mg to about 333 mg of microcrystalline cellulose. In some embodiments, the solid dosage form comprises about 350 mg of the compound of Formula I and about 315 mg of microcrystalline cellulose. In some embodiments, the solid dosage form is a tablet.

In some embodiments, the solid dosage form comprises about 700 mg of the compound of Formula I and about 280 mg to about 840 mg of microcrystalline cellulose. In some embodiments, the solid dosage form comprises about 700 mg of the compound of Formula I and about 560 mg to about 700 mg of microcrystalline cellulose. In some embodiments, the solid dosage form comprises about 700 mg of the compound of Formula I and about 600 mg to about 670 mg of microcrystalline cellulose. In some embodiments, the solid dosage form comprises about 700 mg of the compound of Formula I and about 630 mg of microcrystalline cellulose. In some embodiments, the solid dosage form is a tablet.

In some embodiments, the solid dosage form comprises about 175 mg of the compound of Formula I and about 70 mg to about 210 mg of microcrystalline cellulose. In some embodiments, the solid dosage form comprises about 175 mg of the compound of Formula I and about 140 mg to about 175 mg of microcrystalline cellulose. In some embodiments, the solid dosage form comprises about 175 mg of the compound of Formula I and about 150 mg to about 168 mg of microcrystalline cellulose. In some embodiments, the solid dosage form comprises about 175 mg of the compound of Formula I and about 149 mg to about 167 mg of the filler. In some embodiments, the solid dosage form comprises about 175 mg of the compound of Formula I and about 157.5 mg of microcrystalline cellulose. In some embodiments, the solid dosage form is a tablet.

Film Coating

In some embodiments, solid dosage forms (e.g. tablets) provided herein are uncoated. In certain other embodiments, solid dosage forms (e.g. tablets) provided herein are coated (in which case they include a coating). Although uncoated solid dosage forms (e.g. tablets) may be used, it is more usual in the clinical setting to provide a coated solid dosage forms (e.g. tablets), in which case a conventional non-enteric coating may be used. Film coatings can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though in some embodiments the water soluble material included in the film coating of the embodiments disclosed herein comprises a single polymer material, in certain other embodiments it is formed using a mixture of more than one polymer.

In some embodiments, the coating is yellow or purple. Suitable coatings include, but are not limited to, polymeric film coatings such as those comprising polyvinyl alcohol e.g. 'Opadry® II' (which comprises part-hydrolysed PVA, titanium dioxide, macrogol 3350 (PEG) and talc, with optional coloring such as iron oxide (e.g., iron oxide red or iron oxide black) or indigo carmine or iron oxide yellow or FD&C yellow #6) and Opadry® QX (which comprises polyethylene glycol/macrogol polyvinyl alcohol graft copolymer, talc, titanium dioxide, glyceryl mono and dicaprylocaprate (glyceryl monocaprylocaprate type I), polyvinyl alcohol, and with optional coloring such as iron oxide (e.g., iron oxide red or iron oxide black) or indigo carmine or iron oxide yellow or FD&C yellow #6). In some embodiments, the film coating is Opadry® II purple or yellow. In some embodiments, the film coating is Opadry® QX yellow. The amount of coating is generally between about 2-4% of the tablet core weight. In some embodiments, the amount of the coating is about 3% by weight (based on the tablet core weight).

In some embodiments, the film coating is white. In some embodiments, the coating is Opadry® QX white. The amount of coating is generally between about 2-4% of the tablet core weight. In some embodiments, the amount of the coating is about 3% by weight (based on the tablet core weight).

In some embodiments, the film coating does not comprise $TiO_2$. In some embodiments, the film coating comprises CaCO3. In some embodiments, the film coating comprises a $TiO_2$ free variant of Opadry®.

Unless specifically stated otherwise, where the dosage form is coated, it is to be understood that a reference to % weight is calculated with respect to the tablet core weight.

The "tablet core weight" as calculated herein is the sum total of (i) the compound of Formula I, (ii) the filler, (iii) the disintegrating agent, and (iv) the lubricant. The core tablet weight does not include the weight of the film coating.

The "tablet weight" as calculated herein is the sum total of (i) the compound of Formula I, (ii) the filler, (iii) the disintegrating agent, (iv) the lubricant, and (v) the film coating.

In some embodiments, the solid dosage form comprises:

| Ingredient | % w/w |
|---|---|
| Compound of Formula I | 50% |
| Filler | 44.5% |
| Disintegrating agent | 4.0% |
| Lubricant | 1.5% |
| Film Coat | 3% |

In some embodiments, the solid dosage form is a tablet comprising:

| Ingredient | % w/w |
|---|---|
| Compound of Formula I | 50% |
| Filler | 44.5% |
| Disintegrating agent | 4.0% |
| Lubricant | 1.5% |
| Film Coat | 3% |

In some embodiments, the solid dosage form comprises:

| Ingredient | % w/w |
|---|---|
| Compound of Formula I | 50% |
| Filler | 45% |
| Disintegrating agent | 4% |
| Lubricant | 1% |
| Film Coat | 3% |

In some embodiments, the solid dosage form is a tablet comprising:

| Ingredient | % w/w |
|---|---|
| Compound of Formula I | 50% |
| Filler | 45% |
| Disintegrating agent | 4% |
| Lubricant | 1% |
| Film Coat | 3% |

In some embodiments, the solid dosage form comprises:

| Ingredient | % w/w | Amount (mg) |
|---|---|---|
| Compound of Formula I | 50% | 100 mg |
| Filler | 44.5% | 89 mg |
| Disintegrating agent | 4.0% | 8 mg |
| Lubricant | 1.5% | 3 mg |
| Tablet core weight | | 200 mg |
| Film Coat | 3% | 6 mg |
| Tablet weight | | 206 mg |

In some embodiments, the solid oral dosage form is a tablet comprising:

| Ingredient | % w/w | Amount (mg) |
|---|---|---|
| Compound of Formula I | 50% | 100 mg |
| Filler | 44.5% | 89 mg |
| Disintegrating agent | 4.0% | 8 mg |
| Lubricant | 1.5% | 3 mg |
| Tablet core weight | | 200 mg |
| Film Coat | 3% | 6 mg |
| Tablet weight | | 206 mg |

In some embodiments, the solid dosage form comprises:

| Ingredient | % w/w | Amount (mg) |
|---|---|---|
| Compound of Formula I | 50% | 500 mg |
| Filler | 45% | 450 mg |
| Disintegrating agent | 4% | 40 mg |
| Lubricant | 1% | 5 mg |
| Tablet core weight | | 1000 mg |
| Film Coat | 3% | 30 mg |
| Tablet weight | | 1030 mg |

In some embodiments, the solid dosage form is a tablet comprising:

| Ingredient | % w/w | Amount (mg) |
|---|---|---|
| Compound of Formula I | 50% | 500 mg |
| Filler | 45% | 450 mg |
| Disintegrating agent | 4% | 40 mg |
| Lubricant | 1% | 5 mg |
| Tablet core weight | | 1000 mg |
| Film Coat | 3% | 30 mg |
| Tablet weight | | 1030 mg |

In some embodiments, the solid dosage form is a tablet comprising:

| Ingredient | % w/w | Amount (mg) |
|---|---|---|
| Compound of Formula I | 50% | 500 mg |
| Filler | 45% | 450 mg |
| Disintegrating agent | 4% | 40 mg |
| Lubricant | 1% | 5 mg |
| Tablet core weight | | 1000 mg |
| Film Coat | 3% | 30 mg |
| Tablet weight | | 1030 mg |

In some embodiments, the solid dosage form comprises:

| Ingredient | % w/w | Amount (mg) |
|---|---|---|
| Compound of Formula I | 50% | 350 mg |
| Filler | 45% | 315 mg |
| Disintegrating agent | 4% | 28 mg |
| Lubricant | 1% | 7 mg |
| Tablet core weight | | 700 mg |
| Film Coat | 3% | 21 mg |
| Tablet weight | | 721 mg |

In some embodiments, the solid dosage form comprises:

| Ingredient | % w/w | Amount (mg) |
|---|---|---|
| Compound of Formula I | 50% | 700 mg |
| Filler | 45% | 630 mg |
| Disintegrating agent | 4% | 56 mg |
| Lubricant | 1% | 14 mg |
| Tablet core weight | | 1400 mg |
| Film Coat | 3% | 42 mg |
| Tablet weight | | 1442 mg |

In some embodiments, the solid oral dosage form is a tablet comprising:

| Ingredient | % w/w | Amount (mg) |
|---|---|---|
| Compound of Formula I | 50% | 350 mg |
| Filler | 45% | 315 mg |
| Disintegrating agent | 4% | 28 mg |
| Lubricant | 1% | 7 mg |
| Tablet core weight | | 700 mg |
| Film Coat | 3% | 21 mg |
| Tablet weight | | 721 mg |

In some embodiments, the solid oral dosage form is a tablet comprising:

| Ingredient | % w/w | Amount (mg) |
|---|---|---|
| Compound of Formula I | 50% | 700 mg |
| Filler | 45% | 630 mg |
| Disintegrating agent | 4% | 56 mg |
| Lubricant | 1% | 14 mg |
| Tablet core weight | | 1400 mg |
| Film Coat | 3% | 42 mg |
| Tablet weight | | 1442 mg |

In some embodiments, the solid oral dosage comprises:

| Ingredient | % w/w | Amount (mg |
|---|---|---|
| Compound of Formula I | 50% | 175.0 mg |
| Filler | 45% | 157.5 mg |
| Disintegrating agent | 4% | 14.0 mg |
| Lubricant | 1% | 3.5 mg |
| Tablet core weight | | 350.0 mg |
| Film Coat | 3% | 10.5 mg |
| Tablet weight | | 360.5 mg |

In some embodiments, the solid oral dosage form is a tablet comprising:

| Ingredient | % w/w | Amount (mg) |
|---|---|---|
| Compound of Formula I | 50% | 175.0 mg |
| Filler | 45% | 157.5 mg |
| Disintegrating agent | 4% | 14.0 mg |
| Lubricant | 1% | 3.5 mg |
| Tablet core weight | | 350.0 mg |
| Film Coat | 3% | 10.5 mg |
| Tablet weight | | 360.5 mg |

In some embodiments, the tablet comprises:

| Ingredient | % w/w | Amount (mg) |
|---|---|---|
| Compound of Formula I | 50% | 100 mg |
| Filler (microcrystalline cellulose) | 44.5% | 89 mg |
| Disintegrating agent (crospovidone) | 4.0% | 8 mg |
| Lubricant (magnesium stearate) | 1.5% | 3 mg |
| Tablet core weight | 100% | 200 mg |
| Film Coat | 3% | 6 mg |
| Tablet weight | | 206 mg |

In some embodiments, the tablet comprises:

| Ingredient | % w/w | Amount (mg) |
|---|---|---|
| Compound of Formula I | 50% | 500 mg |
| Filler (microcrystalline cellulose) | 45% | 450 mg |
| Disintegrating agent (crospovidone) | 4% | 40 mg |
| Lubricant (magnesium stearate) | 1% | 10 mg |
| Tablet core weight | | 1000 mg |
| Film Coat | 3% | 30 mg |
| Tablet weight | | 1030 mg |

In some embodiments, the tablet comprises:

| Ingredient | % w/w | Amount (mg) |
|---|---|---|
| Compound of Formula I | 0 | 350 mg |
| Filler (microcrystalline cellulose) | 45% | 315 mg |
| Disintegrating agent (crospovidone) | 4% | 28 mg |
| Lubricant (magnesium stearate) | 1% | 7 mg |
| Tablet core weight | | 700 mg |
| Film Coat | 3% | 21 mg |
| Tablet weight | | 721 mg |

In some embodiments, the tablet comprises:

| Ingredient | % w/w | Amount (mg) |
|---|---|---|
| Compound of Formula I | 50% | 700 mg |
| Filler (microcrystalline cellulose) | 45% | 630 mg |
| Disintegrating agent (crospovidone) | 4% | 56 mg |
| Lubricant (magnesium stearate) | 1% | 14 mg |
| Tablet core weight | | 1400 mg |
| Film Coat | 3% | 42 mg |
| Tablet weight | | 1442 mg |

In some embodiments, the tablet comprises:

| Ingredient | % w/w | Amount (mg) |
|---|---|---|
| Compound of Formula I | 50% | 175.0 mg |
| Filler (microcrystalline cellulose) | 45% | 157.5 mg |
| Disintegrating agent (crospovidone) | 4% | 14.0 mg |
| Lubricant (magnesium stearate) | 1% | 3.5 mg |
| Tablet core weight | | 350.0 mg |
| Film Coat | 3% | 10.5 mg |
| Tablet weight | | 360.5 mg |

In some embodiments, the tablet comprises:

| Ingredient | % w/w | Amount (mg) |
|---|---|---|
| Intragranular | | |
| Compound of Formula I | 50% | 100 mg |
| Filler (microcrystalline cellulose) | 44.5% | 89 mg |
| Disintegrating agent (crospovidone) | 4% | 8 mg |
| Lubricant (magnesium stearate) | 0.5% | 1 mg |
| Extragranular | | |
| Lubricant (magnesium stearate) | 1% | 2 mg |
| Tablet core weight | 100% | 200 mg |
| Film Coat | 3% | 6 mg |
| Tablet weight | | 206 mg |

In some embodiments, the tablet comprises:

| Ingredient | % w/w | Amount (mg) |
|---|---|---|
| Intragranular | | |
| Compound of Formula I | 50% | 500 mg |
| Filler (microcrystalline cellulose) | 45% | 450 mg |
| Disintegrating agent (crospovidone) | 4% | 40 mg |
| Lubricant (magnesium stearate) | 0.5% | 5 mg |
| Extragranular | | |
| Lubricant (magnesium stearate) | 0.5% | 5 mg |
| Tablet core weight | 100% | 1000 mg |
| Film Coat | 3% | 30 mg |
| Tablet weight | | 1030 mg |

In some embodiments, the tablet comprises:

| Ingredient | % w/w | Amount (mg) |
|---|---|---|
| Intragranular | | |
| Compound of Formula I | 50% | 350 mg |
| Filler (microcrystalline cellulose) | 45% | 315 mg |
| Disintegrating agent (crospovidone) | 4% | 28 mg |
| Lubricant (magnesium stearate) | 0.5% | 3.5 mg |
| Extragranular | | |
| Lubricant (magnesium stearate) | 0.5% | 3.5 mg |
| Tablet core weight | 100% | 700 mg |
| Film Coat | 3% | 21 mg |
| Tablet weight | | 721 mg |

In some embodiments, the tablet comprises:

| Ingredient | % w/w | Amount (mg) |
|---|---|---|
| Intragranular | | |
| Compound of Formula I | 50% | 700 mg |
| Filler (microcrystalline cellulose) | 45% | 630 mg |
| Disintegrating agent (crospovidone) | 4% | 56 mg |
| Lubricant (magnesium stearate) | 0.5% | 7.0 mg |
| Extragranular | | |
| Lubricant (magnesium stearate) | 0.5% | 7.0 mg |
| Tablet core weight | 100% | 1400 mg |
| Film Coat | 3% | 42 mg |
| Tablet weight | | 1442 mg |

In some embodiments, the tablet comprises:

| Ingredient | % w/w | Amount (mg) |
|---|---|---|
| Intragranular | | |
| Compound of Formula I | 50% | 175.00 mg |
| Filler (microcrystalline cellulose) | 45% | 157.50 mg |
| Disintegrating agent (crospovidone) | 4% | 14.00 mg |
| Lubricant (magnesium stearate) | 0.5% | 1.75 mg |
| Extragranular | | |
| Lubricant (magnesium stearate) | 0.5% | 1.75 mg |
| Tablet core weight | 100% | 350.0 mg |
| Film Coat | 3% | 10.5 mg |
| Tablet weight | | 360.5 mg |

In some embodiments, the solid dosage form comprises 175 mg of the compound of Formula I, microcrystalline cellulose, crospovidone, magnesium stearate, and a film coat. In some embodiments, the solid dosage form comprises 175 mg of the compound of Formula I, microcrystalline cellulose, crospovidone, magnesium stearate, and Opadry® QX White.

In some embodiments, the solid dosage form comprises 350 mg of the compound of Formula I, microcrystalline cellulose, crospovidone, magnesium stearate, and a film coat. In some embodiments, the solid dosage form comprises 350 mg of the compound of Formula I, microcrystalline cellulose, crospovidone, magnesium stearate, and Opadry® QX Yellow.

Pharmaceutical Compositions and Tablets

The application also provides pharmaceutical compositions, in particular tablets, that comprise a compound expressed by formula I or a pharmaceutically acceptable salt thereof in which the compound of Formula I is present in an amount of about 40 wt % to 70 wt %. In certain embodiments, the compound is present in an amount of about 45 wt % to about 70 wt %. In certain embodiments, the compound is present in an amount of about 45 wt % to about 55 wt %. In certain embodiments, the compound is present in an amount of about 50 wt %.

The application also provides pharmaceutical compositions, in particular tablets, that comprise a compound expressed by formula I or a pharmaceutically acceptable salt thereof in which the drug loading of the compound of Formula I in the pharmaceutical composition (e.g., tablet) is greater than 40%. In certain embodiments, the drug loading of the compound of Formula I in the pharmaceutical composition or tablet is equal to or less than 70%. In certain embodiments, the drug loading of the compound of Formula I in the pharmaceutical composition or tablet is greater than 40% and equal to or less than 70%. In certain embodiments, the drug loading of the compound of Formula I in the pharmaceutical composition or tablet is equal to or greater than 45% and equal to or less than 70%. In certain embodiments, the drug loading of the compound of Formula I in the pharmaceutical composition or tablet is greater than 45%. In certain embodiments, the drug loading of the compound of Formula I in the pharmaceutical composition or tablet is equal to or less than 55%. In certain embodiments, the drug loading of the compound of Formula I in the pharmaceutical composition or tablet is equal to or greater than 45% and equal to or less than 55%. In certain embodiments, the drug loading of the compound of Formula I in the pharmaceutical composition or tablet is about 50%.

In certain embodiments, the compound is the freebase form of the compound of Formula I. In particularly certain embodiments, the compound is the crystalline freebase form characterized by an X-ray powder diffraction (XRPD) pattern comprising degree 2θ-reflections (+/−0.2 degrees 2θ) at 9.8°, 16.0°, and 25.4°.

The pharmaceutical composition or tablet may further comprise a filler. In certain embodiments, the filler is present in an amount of about 20 to about 60 wt %. In certain embodiments, the filler is present in an amount of about 40 to about 50 wt %. In certain embodiments, the filler is present in an amount of about 44 to about 46 wt %.

In certain embodiments, the filler is microcrystalline cellulose. In certain embodiments, the pharmaceutical composition comprises microcrystalline cellulose in an amount of about 20 to about 60 wt %. In certain embodiments, the microcrystalline cellulose is present in an amount of about 40 to about 50 wt %. In certain embodiments, the microcrystalline cellulose is present in an amount of about 44 to about 46 wt %.

In certain embodiments, the pharmaceutical composition comprises the compound of Formula I or a pharmaceutically acceptable salt thereof in an amount of about 40 wt % to 70 wt % and microcrystalline cellulose in an amount of about 20 wt % to about 60 wt %. Preferably, the pharmaceutical composition comprises the compound of Formula I or a pharmaceutically acceptable salt thereof in an amount of about 45 wt % to 70 wt % and microcrystalline cellulose in an amount of about 20 wt % to about 60 wt %. Preferably, the pharmaceutical composition comprises the compound of Formula I or a pharmaceutically acceptable salt thereof in an amount of about 45 wt % to 55 wt % and microcrystalline cellulose in an amount of about 20 wt % to about 60 wt %. Preferably, the pharmaceutical composition comprises the compound of Formula I or a pharmaceutically acceptable salt thereof in an amount of about 40 wt % to 70 wt % and microcrystalline cellulose in an amount of about 40 wt % to about 50 wt %. Preferably, the pharmaceutical composition comprises the compound of Formula I or a pharmaceutically acceptable salt thereof in an amount of about 45 wt % to 55 wt % and microcrystalline cellulose in an amount of about 40 wt % to about 50 wt %.

The pharmaceutical composition or tablet may further comprise a disintegrating agent. In certain embodiments, the disintegrating agent is present in an amount of about 1 wt % to about 10 wt %. In certain embodiments, the disintegrating agent is present in an amount of about 3 wt % to about 5 wt %.

In certain embodiments, the disintegrating agent is crospovidone. In certain embodiments, the pharmaceutical composition comprises crospovidone in an amount of about 1 wt % to about 10 wt %. In certain embodiments, the pharmaceutical composition comprises crospovidone in an amount of about 3 wt % to about 5 wt %.

The pharmaceutical composition or tablet may further comprise a lubricant. In certain embodiments, the lubricant is present in an amount of about 0.5 wt % to about 5 wt %. In certain embodiments, the lubricant is present in an amount of about 0.5 wt % to about 2 wt %.

In certain embodiments, the lubricant is magnesium stearate. In certain embodiments, the pharmaceutical composition comprises magnesium stearate in an amount of about 0.5 wt % to about 5 wt %. In certain embodiments, the pharmaceutical composition comprises magnesium stearate in an amount of about 0.5 wt % to about 2 wt %.

The pharmaceutical composition or tablet may comprise the compound of Formula I or a pharmaceutically acceptable salt thereof, a filler, a disintegrating agent and a lubricant. In certain embodiments, the filler is microcrystalline cellulose and the disintegrating agent is crospovidone. In certain embodiments, the filler is microcrystalline cellulose and the lubricant is magnesium stearate. In certain embodiments, the disintegrating agent is crospovidone and the lubricant is magnesium stearate. In certain embodiments, the filler is microcrystalline cellulose, the disintegrating agent is crospovidone and the lubricant is magnesium stearate. In certain embodiments, the compound is the freebase form of the compound of Formula I, the filler is microcrystalline cellulose, the disintegrating agent is crospovidone and the lubricant is magnesium stearate.

The pharmaceutical composition or tablet may comprise (i) a compound of Formula I, or a pharmaceutically acceptable salt thereof in an amount of about 40 wt % to about 70 wt %, (ii) microcrystalline cellulose in an amount of about 20 wt % to about 60 wt %, (iii) crospovidone in an amount of about 1 wt % to about 10 wt %; and (iv) magnesium stearate in an amount of about 0.5 wt % to about 5 wt %.

In certain embodiments, the pharmaceutical composition or tablet may comprise (i) a compound of Formula I, or a pharmaceutically acceptable salt thereof in an amount of about 45 wt % to about 70 wt %, (ii) microcrystalline cellulose in an amount of about 20 wt % to about 60 wt %, (iii) crospovidone in an amount of about 1 wt % to about 10 wt %; and (iv) magnesium stearate in an amount of about 0.5 wt % to about 5 wt %. In certain embodiments, the pharmaceutical composition or tablet may comprise (i) a compound of Formula I, or a pharmaceutically acceptable salt thereof in an amount of about 45 wt % to about 55 wt %, (ii) microcrystalline cellulose in an amount of about 20 wt % to about 60 wt %, (iii) crospovidone in an amount of about 1 wt % to about 10 wt %; and (iv) magnesium stearate in an amount of about 0.5 wt % to about 5 wt %. In certain embodiments, the pharmaceutical composition or tablet may comprise (i) a compound of Formula I, or a pharmaceutically acceptable salt thereof in an amount of about 50 wt %, (ii) microcrystalline cellulose in an amount of about 20 wt % to about 60 wt %, (iii) crospovidone in an amount of about 1 wt % to about 10 wt %; and (iv) magnesium stearate in an amount of about 0.5 wt % to about 5 wt %.

In certain embodiments, the pharmaceutical composition or tablet comprises (i) a compound of Formula I, or a pharmaceutically acceptable salt thereof in an amount of about 40 wt % to about 70 wt %, (ii) microcrystalline cellulose in an amount of about 40 wt % to about 50 wt %, (iii) crospovidone in an amount of about 1 wt % to about 10 wt %; and (iv) magnesium stearate in an amount of about 0.5 wt % to about 5 wt %. In certain embodiments, the pharmaceutical composition or tablet may comprise (i) a compound of Formula I, or a pharmaceutically acceptable salt thereof in an amount of about 40 wt % to about 70 wt %, (ii) microcrystalline cellulose in an amount of about 44 wt % to about 66 wt %, (iii) crospovidone in an amount of about 1 wt % to about 10 wt %; and (iv) magnesium stearate in an amount of about 0.5 wt % to about 5 wt %.

In certain embodiments, the pharmaceutical composition or tablet comprises (i) a compound of Formula I, or a pharmaceutically acceptable salt thereof in an amount of about 40 wt % to about 70 wt %, (ii) microcrystalline cellulose in an amount of about 20 wt % to about 60 wt %, (iii) crospovidone in an amount of about 3 wt % to about 5 wt %; and (iv) magnesium stearate in an amount of about 0.5 wt % to about 5 wt %. In certain embodiments, the pharmaceutical composition or tablet may comprise (i) a compound of Formula I, or a pharmaceutically acceptable salt thereof in an amount of about 40 wt % to about 70 wt %, (ii) microcrystalline cellulose in an amount of about 20 wt % to about 60 wt %, (iii) crospovidone in an amount of about 1 wt % to about 10 wt %; and (iv) magnesium stearate in an amount of about 0.5 wt % to about 2 wt %.

In certain embodiments, the pharmaceutical composition or tablet is manufactured by dry granulation. In certain embodiments, the dry granulation is carried out using a roller compaction process.

Administration

The pharmaceutical formulations described herein are for oral administration. The frequency of dosage of a compound described herein will be determined by the needs of the individual patient and can be, for example, once per day or twice, or more times, per day. Administration of the compound continues for as long as necessary to treat the viral infection.

In some embodiments, a single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound described herein is administered once daily in a method described herein. In some embodiments, a compound described herein is administered twice daily in a method described herein. In some embodiments, a compound described herein is administered three times daily in a method described herein. In some embodiments, the pharmaceutical formulations, for example a solid dosage form (e.g., tablet) described herein comprises 350 mg of the compound of Formula I and is administered twice daily. In some embodiments, the pharmaceutical formulations, for example a solid dosage form (e.g., tablet) described herein comprises 700 mg of the compound of Formula I and is administered once daily. In some embodiments, the pharmaceutical formulations, for example a solid dosage form (e.g., tablet) described herein comprises 500 mg of the compound of Formula I and is administered once daily. In some embodiments, the pharmaceutical formulations, for example a solid dosage form (e.g., tablet) described herein comprises 175 mg of the compound of Formula I and is administered twice daily.

In some embodiments, the pharmaceutical formulations, for example a solid dosage form (e.g. tablet) described herein comprises 175 mg of the compound of Formula I and is administered twice daily on day one and then once daily on days 2, 3, 4, and 5. In some embodiments, the pharmaceutical formulations, for example a solid dosage form (e.g. tablet) described herein comprises 350 mg of the compound of Formula I and is administered one daily for day 1, 2, 3, 4, and 5.

In some embodiments, the pharmaceutical formulations described herein are administered to a patient, wherein the patient has mild kidney impairment, moderate kidney impairment, or severe kidney impairment.

In some embodiments, the patient has mild kidney impairment, and the pharmaceutical formulation comprises 350 mg of the compound of Formula I and is administered twice daily. In some embodiments, the patient has mild kidney impairment, and the pharmaceutical formulation comprises 350 mg of the compound of Formula I and is administered twice daily for five days.

In some embodiments, the patient has moderate kidney impairment, and the pharmaceutical formulation comprises 350 mg of the compound of Formula I and is administered once daily. In some embodiments, the patient has moderate kidney impairment, and the pharmaceutical formulation comprises 350 mg of the compound of Formula I and is administered once daily for five days.

In some embodiments, the patient has severe kidney impairment, and the pharmaceutical formulation comprises 350 mg of the compound of Formula I and is administered once daily. In some embodiments, the patient has severe kidney impairment, and the pharmaceutical formulation comprises 175 mg of the compound of Formula I and is administered once daily. In some embodiments, the patient has severe kidney impairment, and the pharmaceutical formulation comprises 350 mg of the compound of Formula I and is administered once daily for one day. In some embodiments, the patient has severe kidney impairment, and the pharmaceutical formulation comprises 175 mg of the compound of Formula I and is administered once daily for four days.

Manufacturing Methods

Methods for producing the pharmaceutical formulations, for example the solid oral dosage forms (e.g., tablets) disclosed herein are also provided.

In general, tableting methods are well known in the art of pharmacy. Techniques and formulations generally are found in Remington's Pharmaceutical Sciences (Mack Publishing Co., Easton, PA), which is hereby incorporated by reference herein in its entirety.

A tablet can be made by compression or molding, optionally with one or more excipients. Compressed tablets may be prepared by compressing in a suitable machine the active ingredient in a free-flowing form such as a powder or granules, optionally mixed with excipients.

In some embodiments, the pharmaceutical composition or tablet is manufactured using a method comprising dry granulation. The dry granulation may be carried out by roller compaction. The dry granulation may be performed on a blend of the compound of Formula I, the filler, the disintegrating agent and the lubricant. In some embodiments, the composition comprises microcrystalline cellulose as a filler, crospovidone as a disintegrating agent and magnesium stearate as a lubricant.

In some embodiments, the manufacturing method includes the following steps:
1. blend the compound of Formula I, filler and disintegrating agent;
2. add lubricant and blend; and
3. dry granulate the resulting blend.

Also provided herein is a method of manufacturing a tablet comprising:
1. blending a compound of Formula I, a filler, and a disintegrating agent to form mixture 1;
2. adding a lubricant to mixture 1 to form mixture 2;
3. blending mixture 2 to form mixture 3; and
3. dry granulating mixture 4 to form the tablet.

In some embodiments, the method comprises mixing the drug substance with the excipients. In some embodiments the manufacturing process comprises co-blending and lubricating the compound of Formula I with intragranular excipients. In some embodiments, the method further comprises roller compaction and/or milling. The resulting Formula I granules are then blended with extragranular excipients. The resulting mixture is then compressed into core tablets. In some embodiments, the tablets are further coated with a film coat. An exemplary manufacturing process is shown in FIG. 1.

Therapeutic Methods

The pharmaceutical formulations, for e.g. the solid oral dosage forms (e.g. tablets) disclosed herein are used for treatment of viral infections. In some embodiments, the solid oral dosage forms (e.g. tablets) disclosed herein are used for pre-exposure prophylaxis (PrEP) to reduce the risk of viral infections.

Accordingly, methods for treating a viral infection in a subject are provided, comprising administering a solid oral dosage form disclosed herein to the subject. Similarly, a solid oral dosage form is provided for use in such treatment methods. Also provided is the use of a solid oral dosage form in the manufacture of an oral dosage form disclosed herein for treatment of viral infections.

In some embodiments, the solid oral dosage forms disclosed herein are used for pre-exposure prophylaxis (PrEP) to reduce the risk viral infections. Accordingly, methods for preventing infection in a subject at risk of infection are provided, comprising administering a solid oral dosage form disclosed herein to the subject. Similarly, a solid oral dosage form disclosed herein is provided for use in such treatment methods. The invention also provides the use of a solid oral dosage form in the manufacture of an oral dosage form disclosed herein for prevention of viral infection in a subject at risk for infection.

The methods involve administering a solid oral dosage form disclosed herein to the subject, typically a human, and will generally involve repeated administrations, typically once daily or twice. In some embodiments, the administration is once daily. In some embodiments, the administration is twice daily. The treatment may be prophylactic or therapeutic treatment.

In some embodiments, the viral infection is a paramyxoviridae virus infection. As such, in some embodiments, the present disclosure provides methods for treating a paramyxoviridae infection in a subject (e.g., a human) in need thereof, the method comprising administering to the subject a solid oral dosage form (in particular a tablet) disclosed herein. Paramyxoviridae viruses include, but are not limited to Nipah virus, Hendra virus, measles, mumps, and parainfluenze virus.

In some embodiments, the viral infection is a human parainfluenza virus, Nipah virus, Hendra virus, measles, or mumps infection.

In some embodiments, the viral infection is a pneumoviridae virus infection. As such, in some embodiments, the present disclosure provides a method of treating a pneumoviridae virus infection in a human in need thereof, the method comprising administering to the human a solid oral dosage form (in particular a tablet) provided herein. Pneumoviridae viruses include, but are not limited to, respiratory snycytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a solid oral dosage form (in particular a tablet) disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a solid oral dosage form (in particular a tablet) provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a solid oral dosage form (in particular a tablet) disclosed herein, wherein the administration is by inhalation.

In some embodiments, the present disclosure provides a method for reducing the viral load associated with RSV infection, wherein the method comprises administering to a human infected with RSV a solid oral dosage form (in particular a tablet) disclosed herein.

In some embodiments, the viral infection is a picornaviridae virus infection. As such, in some embodiments, the present disclosure provides a method of treating a picomaviridae virus infection in a human in need thereof, the method comprising administering to the human a solid oral dosage form (in particular a tablet) of the present disclosure. Picomaviridae viruses are eneteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection (HRV). In some embodiments, the Picornaviridae virus infection is HRV-A, HRV-B, or HRV-C infection.

In some embodiments, the viral infection is selected from the group consisting of Coxsackie A virus infection, Coxsackie A virus infection, enterovirus D68 infection, enterovirus B69 infection, enterovirus D70 infection, enterovirus A71 infection, and poliovirus infection.

In some embodiments, the present disclosure provides a solid oral dosage form (in particular a tablet), for use in the treatment of a picornaviridae virus infection in a human in need thereof. In some embodiments, the picomaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to the human a solid oral dosage form (in particular a tablet) described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a Japanese ensephalitis virus infection. In some embodiments, the flaviviridae virus infection is a hepatitis C virus infection.

In some embodiments, the flaviviridae virus infection is a dengue virus infection, yellow fever virus infection, West Nile virus infection, tick borne encephalitis, Kunjin Japanese encephalitis, St. Louis encephalitis, Murray valley encephalitis, Omsk hemorrhagic fever, bovine viral diarrhea, zika virus infection, or a HCV infection.

In some embodiments, the present disclosure provides use of a solid oral dosage form (in particular a tablet) disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human a solid oral dosage form (in particular a tablet) disclosed herein. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a solid oral dosage form (in particular a tablet) for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a solid oral dosage form (in particular a tablet) provided herein. In some embodiments, the coronavirus infection is a Severe Acute Respiratory Syndrome (SARS-CoV) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. In some embodiments, the viral infection is a zoonotic coronavirus infection, In some embodiments, the viral infection is caused by a virus having at least 70% sequence homology to a viral polymerase selected from the group consisting of SARS-CoV polymerase, MERS-CoV polymerase and SARS-CoV-2. In some embodiments, the viral infection is caused by a virus having at least 80% sequence homology to a viral polymerase selected from the group consisting of SARS-CoV polymerase, MERS-CoV polymerase and SARS-CoV-2. In some embodiments, the viral infection is caused by a virus having at least 90% sequence homology to a viral polymerase selected from the group consisting of SARS-CoV polymerase, MERS-CoV polymerase and SARS-CoV-2. In some embodiments, the viral infection is caused by a virus having at least 95% sequence homology to a viral polymerase selected from the group consisting of SARS-CoV polymerase, MERS-CoV polymerase and SARS-CoV-2.

In some embodiments, the viral infection is caused by a variant of SARS-CoV-2, for example by the B.1.1.7 variant (the UK variant), B.1.351 variant (the South African variant), P.1 variant (the Brazil variant), B.1.1.7 with E484K variant, B.1.1.207 variant, B.1.1.317 variant, B.1.1.318 variant, B.1.429 variant, B.1.525 variant, or P.3 variant. In some embodiments, the viral infection is caused by the B.1.1.7 variant of SARS-CoV-2. In some embodiments, the viral infection is caused by the B.1.351 variant of SARS-CoV-2. In some embodiments, the viral infection is caused by the P.1 variant of SARS-CoV-2.

In some embodiments, the present disclosure provides a solid oral dosage form (in particular a tablet) for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, and zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

In some embodiments, the viral infection is an arenaviridae virus infection. As such, in some embodiments, the disclosure provides a method of treating an arenaviridae virus infection in a human in need thereof, the method comprising administering to the human a solid oral dosage form (in particular a tablet) disclosed herein. In some embodiments, the arenaviridae virus infection is a Lassa infection or a Junin infection.

In some embodiments, the present disclosure provides a compound for use in the treatment of an arenaviridae virus infection in a human in need thereof. In some embodiments, the arenaviridae virus infection is a Lassa infection or a Junin infection.

In some embodiments, the viral infection is an orthomyxovirus infection, for example, an influenza virus infection. In some embodiments, the viral infection is an influenza virus A, influenza virus B, or influenza virus C infection.

As described more fully herein, the solid oral dosage form (in particular a tablet) described herein can be administered with one or more additional therapeutic agent(s) to an individual (e.g., a human) infected with a viral infection. The additional therapeutic agent(s) can be administered to the infected individual at the same time as the compound of the present disclosure or before or after administration of the compound of the present disclosure.

Combination Therapy

The pharmaceutical formulation, for example the solid oral dosage forms described herein, can also be used in combination with one or more additional therapeutic agents. As such, also provided herein are methods of treatment of a viral infection in a subject in need thereof, wherein the methods comprise administering to the subject a solid oral dosage form disclosed therein and a therapeutically effective amount of one or more additional therapeutic or prophylactic agents.

In some embodiments, the additional therapeutic agent is an antiviral agent. Any suitable antiviral agent can be used in the methods described herein.

In some embodiments, the additional therapeutic agent a 2,5-Oligoadenylate synthetase stimulator, 5-HT 2a receptor antagonist, 5-Lipoxygenase inhibitor, ABL family tyrosine kinase inhibitor, Abl tyrosine kinase inhibitor, Acetaldehyde dehydrogenase inhibitor, Acetyl CoA carboxylase inhibitor, Actin antagonist, Actin modulator, Activity-dependent neuroprotector modulator, Adenosine A3 receptor agonist, Adrenergic receptor antagonist, Adrenomedullin ligand, Adrenomedullin ligand inhibitor, Advanced glycosylation product receptor antagonist, Advanced glycosylation product receptor modulator, AKT protein kinase inhibitor, Alanine proline rich secreted protein stimulator, Aldose reductase inhibitor, Alkaline phosphatase stimulator, Alpha 2 adrenoceptor antagonist, Alpha 2B adrenoceptor agonist, AMP activated protein kinase stimulator, AMPA receptor modulator, Amyloid protein deposition inhibitor, Androgen receptor antagonist, Angiotensin II AT-1 receptor antagonist, Angiotensin II AT-2 receptor agonist, Angiotensin II receptor modulator, Angiotensin converting enzyme 2 inhibitor, Angiotensin converting enzyme 2 modulator, Angiotensin converting enzyme 2 stimulator, Angiotensin receptor modulator, Annexin A5 stimulator, Anoctamin 1 inhibitor, Anti-coagulant, Anti-histamine, Anti-hypoxic, Anti-thrombotic, AP1 transcription factor modulator, Apelin receptor agonist, APOA1 gene stimulator, Apolipoprotein A1 agonist, Apolipoprotein B antagonist, Apolipoprotein B modulator, Apolipoprotein C3 antagonist, Aryl hydrocarbon receptor agonist, Aryl hydrocarbon receptor antagonist, ATP binding cassette transporter B5 modulator, Axl tyrosine kinase receptor inhibitor, Bactericidal permeability protein inhibitor, Basigin inhibitor, Basigin modulator, BCL2 gene inhibitor, BCL2L11 gene stimulator, Bcr protein inhibitor, Beta 1 adrenoceptor modulator, Beta 2 adrenoceptor agonist, Beta adrenoceptor agonist, Beta-arrestin stimulator, Blood clotting modulator, BMP10 gene inhibitor, BMP15 gene inhibitor, Bone morphogenetic protein-10 ligand inhibitor, Bone morphogenetic protein-15 ligand inhibitor, Bradykinin B2 receptor antagonist, Brain derived neurotrophic factor ligand, Bromodomain containing protein 2 inhibitor, Bromodomain containing protein 4 inhibitor, Btk tyrosine kinase inhibitor, C-reactive protein modulator, Ca2+ release activated Ca2+ channel 1 inhibitor, Cadherin-5 modulator, Calcium activated chloride channel inhibitor, Calcium channel modulator, Calpain-I inhibitor, Calpain-II inhibitor, Calpain-IX inhibitor, Cannabinoid CB2 receptor agonist, Cannabinoid receptor modulator, Casein kinase II inhibitor, CASP8-FADD-like regulator inhibitor, Caspase inhibitor, Catalase stimulator, CCL26 gene inhibitor, CCR2 chemokine antagonist, CCR5 chemokine antagonist, CD11a agonist, CD122 agonist, CD3 antagonist, CD4 agonist, CD40 ligand, CD40 ligand modulator, CD40 ligand receptor agonist, CD40 ligand receptor modulator, CD49d agonist, CD70 antigen modulator, CD73 agonist, CD73 antagonist, CD95 antagonist, CFTR inhibitor, CGRP receptor antagonist, Chemokine receptor-like 1 agonist, Chloride channel inhibitor, Chloride channel modulator, Cholera enterotoxin subunit B inhibitor, Cholesterol ester transfer protein inhibitor, Collagen modulator, Complement CIs subcomponent inhibitor, Complement C3 inhibitor, Complement C5 factor inhibitor, Complement C5a factor inhibitor, Complement Factor H stimulator, Complement cascade inhibitor, Complement factor C2 inhibitor, Complement factor D inhibitor, Connective tissue growth factor ligand inhibitor, Coronavirus nucleoprotein modulator, Coronavirus small envelope protein modulator, Coronavirus spike glycoprotein inhibitor, Coronavirus spike glycoprotein modulator, COVID19 envelope small membrane protein modulator, COVID19 non-structural protein 8 modulator, COVID19 nucleoprotein modulator, COVID19 Protein 3a inhibitor, COVID19 replicase polyprotein 1a inhibitor, COVID19 replicase polyprotein 1a modulator, COVID19 replicase polyprotein 1ab inhibitor, COVID19 replicase polyprotein 1ab modulator, COVID19 Spike glycoprotein inhibitor, COVID19 Spike glycoprotein modulator, COVID19 structural glycoprotein modulator, CRF-2 receptor agonist, CSF-1 agonist, CSF-1 antagonist, CX3CR1 chemokine antagonist, CXC10 chemokine ligand inhibitor, CXC5 chemokine ligand inhibitor, CXCL1 gene modulator, CXCL2 gene modulator, CXCL3 gene modulator, CXCR1 chemokine antagonist, CXCR2 chemokine antagonist, CXCR4 chemokine antagonist, Cyclin D1 inhibitor, Cyclin E inhibitor, Cyclin-dependent kinase-1 inhibitor, Cyclin-dependent kinase-2 inhibitor, Cyclin-dependent kinase-5 inhibitor, Cyclin-dependent kinase-7 inhibitor, Cyclin-dependent kinase-9 inhibitor, Cyclooxygenase 2 inhibitor, Cyclooxygenase inhibitor, Cyclophilin inhibitor, Cysteine protease inhibitor, Cytochrome P450 3A4 inhibitor, Cytokine receptor antagonist, Cytotoxic T lymphocyte protein gene modulator, Cytotoxic T-lymphocyte protein-4 inhibitor, Cytotoxic T-lymphocyte protein-4 stimulator, DDX3 inhibitor, Dehydrogenase inhibitor, Dehydropeptidase-1 modulator, Deoxyribonuclease I stimulator, Deoxyribonuclease gamma stimulator, Deoxyribonuclease stimulator, Dihydroceramide delta 4 desaturase inhibitor, Dihydroorotate dehydrogenase inhibitor, Dipeptidyl peptidase I inhibitor, Dipeptidyl peptidase III inhibitor, Diuretic, DNA binding protein inhibitor, DNA methyltransferase inhibitor, Dopamine transporter inhibitor, E selectin antagonist, Ecto NOX disulfide thiol exchanger 2 inhibitor, EGFR gene inhibitor, Elongation factor 1 alpha 2 modulator, Endoplasmin modulator, Endoribonuclease DICER modulator, Endothelin ET-A receptor antagonist, Epidermal growth factor receptor antagonist, E-selectin antagonist, Estrogen receptor beta agonist, Estrogen receptor modulator, Eukaryotic initiation factor 4A-I inhibitor, Exo-alpha sialidase modulator, Exportin 1 inhibitor, Factor Ia modulator, Factor IIa modulator, Factor VII antagonist, Factor Xa antagonist, Factor XIa antagonist, FGF receptor antagonist, FGF-1 ligand, FGF-1 ligand inhibitor, FGF-2 ligand inhibitor, FGF1 receptor antagonist, FGF2 receptor antagonist, FGF3 receptor antagonist, Flt3 tyrosine kinase inhibitor, Fractalkine ligand inhibitor, Free fatty acid receptor 2 agonist, Free fatty acid receptor 3 agonist, furin inhibitors, Fyn tyrosine kinase inhibitor, FYVE finger phosphoinositide kinase inhibitor, G-protein coupled bile acid receptor 1 agonist, GABA A receptor modulator, Galectin-3 inhibitor, Gamma-secretase inhibitor, GDF agonist, Gelsolin stimulator, Glial cell neurotrophic factor ligand, Glucocorticoid receptor agonist, Glutathione peroxidase stimulator, GM-CSF ligand inhibitor, GM-CSF receptor agonist, GM-CSF receptor modulator, Griffithsin modulator, Growth regulated protein alpha ligand inhibitor, Grp78 calcium binding protein inhibitor, Heat shock protein HSP90 alpha inhibitor, Heat shock protein HSP90 beta inhibitor, Heat shock protein inhibitor, Heat shock protein stimulator, Hemagglutinin modulator, Hemoglobin modulator, Hemolysin alpha inhibitor, Heparanase inhibitor, Heparin agonist, Hepatitis B structural protein inhibitor, Hepatitis C virus NS5B polymerase inhibitor, HIF prolyl hydroxylase inhibitor, HIF prolyl hydroxylase-2 inhibitor, High mobility group protein B1 inhibitor, Histamine H1 receptor antagonist, Histamine H2 receptor antagonist, Histone deacetylase-6 inhibitor, Histone inhibitor, HIV protease inhibitor, HIV-1 gp120 protein inhibitor, HIV-1 protease inhibitor, HIV-1 reverse transcriptase inhibitor, HLA class I antigen modulator, HLA class II antigen modulator, Host cell factor modulator, Hsp 90 inhibitor, Human papillomavirus E6 protein modulator, Human papillomavirus E7 protein modulator, Hypoxia inducible factor inhibitor gene inhibitor, Hypoxia inducible factor-2 alpha modulator, I-kappa B kinase inhibitor, I-kappa B kinase modulator, ICAM-1 stimulator, IgG receptor FcRn large subunit p51 modulator, IL-12 receptor antagonist, IL-15 receptor agonist, IL-15 receptor modulator, IL-17 antagonist, IL-18 receptor accessory protein antagonist, IL-2 receptor agonist, IL-22 agonist, IL-23 antagonist, IL-6 receptor agonist, IL-6 receptor antagonist, IL-6 receptor modulator, IL-7 receptor agonist, IL-8 receptor antagonist, IL12 gene stimulator, IL8 gene modulator, Immunoglobulin G modulator, Immunoglobulin GI agonist, Immunoglobulin GI modulator, Immunoglobulin agonist, Immunoglobulin gamma Fc receptor I modulator, Immunoglobulin kappa modulator, Inosine monophosphate dehydrogenase inhibitor, Insulin sensitizer, Integrin agonist, Integrin alpha-4/beta-7 antagonist, Integrin alpha-V/beta-1 antagonist, Integrin alpha-V/beta-6 antagonist, Interferon agonist, Interferon alpha 14 ligand, Interferon alpha 2 ligand, Interferon alpha 2 ligand modulator, Interferon alpha ligand, Interferon alpha ligand inhibitor, Interferon alpha ligand modulator, Interferon beta ligand, Interferon gamma ligand inhibitor, Interferon gamma receptor agonist, Interferon gamma receptor antagonist, Interferon receptor modulator, Interferon type I receptor agonist, Interleukin 17A ligand inhibitor, Interleukin 17F ligand inhibitor, Interleukin 18 ligand inhibitor, Interleukin 22 ligand, Interleukin-1 beta ligand inhibitor, Interleukin-1 beta ligand modulator, Interleukin-1 ligand inhibitor, Interleukin-2 ligand, Interleukin-29 ligand, Interleukin-6 ligand inhibitor, Interleukin-7 ligand, Interleukin-8 ligand inhibitor, IRAK-4 protein kinase inhibitor, JAK tyrosine kinase inhibitor, Jak1 tyrosine kinase inhibitor, Jak2 tyrosine kinase inhibitor, Jak3 tyrosine kinase inhibitor, Jun N terminal kinase inhibitor, Jun N terminal kinase modulator, Kallikrein modulator, Kelch like ECH associated protein 1 modulator, Kit tyrosine kinase inhibitor, KLKB1 gene inhibitor, Lactoferrin stimulator, Lanosterol-14 demethylase inhibitor, Lck tyrosine kinase inhibitor, Leukocyte Ig like receptor A4 modulator, Leukocyte elastase inhibitor, Leukotriene BLT receptor antagonist, Leukotriene D4 antagonist, Leukotriene receptor antagonist, Listeriolysin stimulator, Liver X receptor antagonist, Low molecular weight heparin, Lung surfactant associated protein B stimulator, Lung surfactant associated protein D modulator, Lyn tyrosine kinase inhibitor, Lyn tyrosine kinase stimulator, Lysine specific histone demethylase 1 inhibitor, Macrophage migration inhibitory factor inhibitor, Mannan-binding lectin serine protease inhibitor, Mannan-binding lectin serine protease-2 inhibitor, MAO B inhibitor, MAP kinase inhibitor, MAPK gene modulator, Matrix metalloprotease modulator, Maxi K potassium channel inhibitor, MCL1 gene inhibitor, MEK protein kinase inhibitor, MEK-1 protein kinase inhibitor, Melanocortin MC1 receptor agonist, Melanocortin MC3 receptor agonist, Metalloprotease-12 inhibitor, METTL3 gene inhibitor, Moesin inhibitor, Moesin modulator, Monocyte chemotactic protein 1 ligand inhibitor, Monocyte differentiation antigen CD14 inhibitor, mRNA cap guanine N7 methyltransferase modulator, mTOR complex 1 inhibitor, mTOR complex 2 inhibitor, mTOR inhibitor, Mucolipin modulator, Muscarinic receptor antagonist, Myeloperoxidase inhibitor, NACHT LRR PYD domain protein 3 inhibitor, NAD synthase modulator, NADPH oxidase inhibitor, Neuropilin 2 modulator, Neuroplastin inhibitor, NFE2L2 gene stimulator, NK cell receptor agonist, NK1 receptor antagonist, NMDA receptor antagonist, NMDA receptor epsilon 2 subunit inhibitor, Non receptor tyrosine kinase TYK2 antagonist, Non-nucleoside reverse transcriptase inhibitor, Nuclear erythroid 2-related factor 2 stimulator, Nuclear factor kappa B inhibitor, Nuclear factor kappa B modulator, Nuclease stimulator, Nucleolin inhibitor, Nucleoprotein inhibitor, Nucleoprotein modulator, Nucleoside reverse transcriptase inhibitor, Opioid receptor agonist, Opioid receptor antagonist, Opioid receptor mu modulator, Opioid receptor sigma antagonist 1, Ornithine decarboxylase inhibitor, Outer membrane protein inhibitor, OX40 ligand, p38 MAP kinase alpha inhibitor, p38 MAP kinase inhibitor, p38 MAP kinase modulator, p53 tumor suppressor protein stimulator, Palmitoyl protein thioesterase 1 inhibitor, Papain inhibitor, PARP inhibitor, PARP modulator, PDE 10 inhibitor, PDE 3 inhibitor, PDE 4 inhibitor, PDGF receptor alpha antagonist, PDGF receptor antagonist, PDGF receptor beta antagonist, Peptidyl-prolyl cis-trans isomerase A inhibitor, Peroxiredoxin 6 modulator, PGD2 antagonist, PGI2 agonist, P-glycoprotein inhibitor, Phosphoinositide 3-kinase inhibitor, Phosphoinositide-3 kinase delta inhibitor, Phosphoinositide-3 kinase gamma inhibitor, Phospholipase A2 inhibitor, Plasma kallikrein inhibitor, Plasminogen activator inhibitor 1 inhibitor, Platelet inhibitor, Platelet glycoprotein VI inhibitor, Polo-like kinase 1 inhibitor, Poly ADP ribose polymerase 1 inhibitor, Poly ADP ribose polymerase 2 inhibitor, Polymerase cofactor VP35 inhibitor, PPAR alpha agonist, Progesterone receptor agonist, Programmed cell death protein 1 modulator, Prolyl hydroxylase inhibitor, Prostaglandin E synthase-1 inhibitor, Protease inhibitor, Proteasome inhibitor, Protein arginine deiminase IV inhibitor, Protein tyrosine kinase inhibitor, Protein tyrosine phosphatase beta inhibitor, Protein tyrosine phosphatase-2C inhibitor, Proto-oncogene Mas agonist, Purinoceptor antagonist, Raf protein kinase inhibitor, RANTES ligand, Ras gene inhibitor, Retinoate receptor responder protein 2 stimulator, Rev protein modulator, Ribonuclease stimulator, RIP-1 kinase inhibitor, RNA helicase inhibitor, RNA polymerase inhibitor, RNA polymerase modulator, S phase kinase associated protein 2 inhibitor, SARS coronavirus 3C protease like inhibitor, Serine protease inhibitor, Serine threonine protein kinase ATR inhibitor, Serine threonine protein kinase TBK1 inhibitor, Serum amyloid A protein modulator, Signal transducer CD24 stimulator, Sodium channel stimulator, Sodium glucose transporter-2 inhibitor, Sphingosine kinase 1 inhibitor, Sphingosine kinase 2 inhibitor, Sphingosine kinase inhibitor, Sphingosine-1-phosphate receptor-1 agonist, Sphingosine-1-phosphate receptor-1 antagonist, Sphingosine-1-phosphate receptor-1 modulator, Sphingosine-1-phosphate receptor-5 agonist, Sphingosine-1-phosphate receptor-5 modulator, Spike glycoprotein inhibitor, Src tyrosine kinase inhibitor, STAT-1 modulator, STAT-3 inhibitor, STAT-5 inhibitor, STAT3 gene inhibitor, Stem cell antigen-1 inhibitor, Stimulator of interferon genes protein stimulator, Sulfatase inhibitor, Superoxide dismutase modulator, Superoxide dismutase stimulator, Syk tyrosine kinase inhibitor, T cell immunoreceptor Ig ITIM protein inhibitor, T cell receptor agonist, T cell surface glycoprotein CD28 inhibitor, T-cell differentiation antigen CD6 inhibitor, T-cell surface glycoprotein CD8 stimulator, T-cell transcription factor NFAT modulator, Tankyrase-1 inhibitor, Tankyrase-2 inhibitor, Tek tyrosine kinase receptor stimulator, Telomerase modulator, Tetanus toxin modulator, TGF beta receptor antagonist, TGFB2 gene inhibitor, Thymosin beta 4 ligand, Thyroid hormone receptor beta agonist, Tissue factor inhibitor, Tissue plasminogen activator modulator, Tissue plasminogen activator stimulator, TLR agonist, TLR modulator, TLR-2 agonist, TLR-2 antagonist, TLR-3 agonist, TLR-4 agonist, TLR-4 antagonist, TLR-6 agonist, TLR-7 agonist, TLR-7 antagonist, TLR-8 antagonist, TLR-9 agonist, TMPRSS2 gene inhibitor, TNF alpha ligand inhibitor, TNF alpha ligand modulator, TNF binding agent, TNF gene inhibitor, Topoisomerase inhibitor, Transcription factor EB stimulator, Transferrin modulator, Transketolase inhibitor, Translocation associated protein inhibitor, Transmembrane serine protease 2 inhibitor, Transthyretin modulator, TREM receptor 1 antagonist, TRP cation channel C1 modulator, TRP cation channel C6 inhibitor, TRP cation channel V6 inhibitor, Trypsin 1 inhibitor, Trypsin 2 inhibitor, Trypsin 3 inhibitor, Trypsin inhibitor, Tubulin alpha inhibitor, Tubulin beta inhibitor, Tumor necrosis factor 14 ligand inhibitor, TYK2 gene inhibitor, Type I IL-1 receptor antagonist, Tyrosine protein kinase ABL1 inhibitor, Ubiquinol cytochrome C reductase 14 kDa inhibitor, Ubiquitin ligase modulator, Unspecified GPCR agonist, Unspecified cytokine receptor modulator, Unspecified enzyme stimulator, Unspecified gene inhibitor, Unspecified receptor modulator, Urokinase plasminogen activator inhibitor, Vascular cell adhesion protein 1 agonist, Vasodilator, VEGF ligand inhibitor, VEGF receptor antagonist, VEGF-1 receptor antagonist, VEGF-1 receptor modulator, VEGF-2 receptor antagonist, VEGF-3 receptor antagonist, Vimentin inhibitor, Vimentin modulator, VIP receptor agonist, Viral envelope protein inhibitor, Viral protease inhibitor, Viral protease modulator, Viral protein target modulator, Viral ribonuclease inhibitor, Viral structural protein modulator, Vitamin D3 receptor agonist, X-linked inhibitor of apoptosis protein inhibitor, Xanthine oxidase inhibitor, or Zonulin inhibitor.

In some embodiments, the solid oral dosage forms of the present disclosure may be administered in combination with a Sars-Cov-2 treatment, such as parenteral fluids (including dextrose saline and Ringer's lactate), nutrition, antibiotics (including azithromycin, metronidazole, amphotericin B, amoxicillin/clavulanate, trimethoprim/sulfamethoxazole, R-327 and cephalosporin antibiotics, such as ceftriaxone and cefuroxime), antifungal prophylaxis, fever and pain medication, antiemetic (such as metoclopramide) and/or antidiarrheal agents, vitamin and mineral supplements (including Vitamin K, vitamin D, cholecalciferol, vitamin C and zinc sulfate), anti-inflammatory agents (such as ibuprofen or steroids), corticosteroids such as dexamethasone, methylprednisolone, prednisone, mometasone, immunomodulatory medications (eg interferon), vaccines, and pain medications.

In some embodiments, the additional therapeutic agent is an Abl tyrosine kinase inhibitor, such as radotinib or imatinib.

In some embodiments, the additional therapeutic agent is an acetaldehyde dehydrogenase inhibitor, such as ADX-629.

In some embodiments, the additional therapeutic agent is an adenosine A3 receptor agonist, such as piclidenoson.

In some embodiments, the additional therapeutic agent is an adrenomedullin ligand such as adrenomedullin.

In some embodiments, the additional therapeutic agent is a p38 MAPK+PPAR gamma agonist/insulin sensitizer such as KIN-001.

In some embodiments, the additional therapeutic agent is a PPAR alpha agonist such as DWTC-5101 (fenofibrate choline).

In some embodiments, the additional therapeutic agent is a cyclophilin inhibitor such as rencofilstat.

In some embodiments, the additional therapeutic is a p38 MAP kinase inhibitor such as PRX-201 or Gen-1124.

In some embodiments, the additional therapeutic agent is an aldose reductase inhibitor, such as caficrestat.

In some embodiments, the additional therapeutic agent is an AMPA receptor modulator, such as traneurocin.

In some embodiments, the additional therapeutic agent is an annexin A5 stimulator, such as AP-01 or SY-005.

In some embodiments, the additional therapeutic agent is an apelin receptor agonist, such as CB-5064MM.

In some embodiments, the additional therapeutic agent is an anti-coagulant, such as heparins (heparin and low molecular weight heparin), aspirin, apixaban, dabigatran, edoxaban, argatroban, enoxaparin, or fondaparinux.

In some embodiments, the additional therapeutic agent is an androgen receptor antagonist such as bicalutamide, enzalutamide, or pruxelutamide (proxalutamide).

In some embodiments, the additional therapeutic agent is anti-hypoxic, such as trans-sodium crocetinate.

In some embodiments, the additional therapeutic agent is an anti-thrombotic, such as defibrotide, rivaroxaban, alteplase, tirofiban, clopidogrel, prasugrel, bemiparin, bivalirudin, sulodexide, or tenecteplase.

In some embodiments, the additional therapeutic agent is an antihistamine, such as cloroperastine or clemastine.

In some embodiments, the additional therapeutic agent is an apolipoprotein A1 agonist, such as CER-001.

In some embodiments, the additional therapeutic agent is a phospholipase A2 inhibitor, such as icosapent ethyl.

In some embodiments, the additional therapeutic agent is an axl tyrosine kinase receptor inhibitor, such as bemcentinib.

In some embodiments, the additional therapeutic agent is a corticosteroid/beta 2 adrenoceptor agonist, such as budesonide+formoterol fumarate.

In some embodiments, the additional therapeutic agent is a BET bromodomain inhibitor/APOA1 gene stimulator such as apabetalone.

In some embodiments, the additional therapeutic agent is a blood clotting modulator, such as lanadelumab.

In some embodiments, the additional therapeutic agent is a bradykinin B2 receptor antagonist, such as icatibant.

In some embodiments, the additional therapeutic agent is an EGFR gene inhibitor/Btk tyrosine kinase inhibitor, such as abivertinib.

In some embodiments, the additional therapeutic agent is a Btk tyrosine kinase inhibitor, such as ibrutinib or zanubrutinib.

In some embodiments, the additional therapeutic agent is a calpain-I/II/IX inhibitor, such as BLD-2660.

In some embodiments, the additional therapeutic agent is a cannabinoid CB2 receptor agonist, such as ontemabez or PPP-003.

In some embodiments, the additional therapeutic agent is a Ca2+ release activated Ca2+ channel 1 inhibitor, such as zegocractin (CM-4620).

In some embodiments, the additional therapeutic agent is an ATR inhibitor, such as berzosertib.

In some embodiments, the additional therapeutic agent is a cadherin-5 modulator, such as FX-06.

In some embodiments, the additional therapeutic agent is a casein kinase II inhibitor, such as silmitasertib.

In some embodiments, the additional therapeutic agent is a caspase inhibitor, such as emncasan.

In some embodiments, the additional therapeutic agent is a catalase stimulator/superoxide dismutase stimulator, such as MP-1032.

In some embodiments, the additional therapeutic agent is a CCR2 chemokine antagonist/CCR5 chemokine antagonist such as cenicriviroc.

In some embodiments, the additional therapeutic agent is a CCR5 chemokine antagonist, such as maraviroc or leronlimab.

In some embodiments, the additional therapeutic agent is a CD122 agonist/IL-2 receptor agonist, such as bempegaldesleukin.

In some embodiments, the additional therapeutic agent is a CD73 agonist/interferon beta ligand, such as FP-1201.

In some embodiments, the additional therapeutic agent is a cholesterol ester transfer protein inhibitor, such as dalcetrapib.

In some embodiments, the additional therapeutic agent is a Mannan-binding lectin serine protease/complement CIs subcomponent inhibitor/myeloperoxidase inhibitor, such as RLS-0071.

In some embodiments, the additional therapeutic agent is a complement C5 factor inhibitor/leukotriene BLT receptor antagonist, such as nomacopan.

In some embodiments, the additional therapeutic agent is a complement C5 factor inhibitor, such as eculizumab, STSA-1002, zilucoplan.

In some embodiments, the additional therapeutic agent is a CXCR4 chemokine antagonist, such as plerixafor or motixafortide.

In some embodiments, the additional therapeutic agent is a cytochrome P450 3A4 inhibitor/peptidyl-prolyl cis-trans isomerase A inhibitor, such as alisporivir.

In some embodiments, the additional therapeutic agent is a cysteine protease inhibitor, such as SLV-213.

In some embodiments, the additional therapeutic agent is a dihydroorotate dehydrogenase inhibitor, such as Meds-433, brequinar, RP-7214, or emvododstat.

In some embodiments, the additional therapeutic agent is a dehydropeptidase-1 modulator, such as Metablok.

In some embodiments, the additional therapeutic agent is a dihydroorotate dehydrogenase inhibitor/IL-17 antagonist, such as vidofludimus.

In some embodiments, the additional therapeutic agent is a diuretic, such as an aldosterone antagonist, such as spironolactone.

In some embodiments, the additional therapeutic agent is a deoxyribonuclease I stimulator, such as GNR-039 or domase alfa.

In some embodiments, the additional therapeutic agent is a NET inhibitor, such as NTR-441.

In some embodiments, the additional therapeutic agent is a dihydroceramide delta 4 desaturase inhibitor/sphingosine kinase 2 inhibitor, such as opaganib.

In some embodiments, the additional therapeutic agent is a DNA methyltransferase inhibitor, such as azacytidine.

In some embodiments, the additional therapeutic agent is an LXR antagonist, such as larsucosterol.

In some embodiments, the additional therapeutic agent is a dipeptidyl peptidase I inhibitor, such as brensocatib.

In some embodiments, the additional therapeutic agent is a protein arginine deiminase IV inhibitor, such as JBI-1044.

In some embodiments, the additional therapeutic agent is an elongation factor 1 alpha 2 modulator, such as plitidepsin.

In some embodiments, the additional therapeutic agent is a eukaryotic initiation factor 4A-I inhibitor, such as zotatifin.

In some embodiments, the additional therapeutic agent is an exo-alpha sialidase modulator, such as DAS-181.

In some embodiments, the additional therapeutic agent is an exportin 1 inhibitor, such as selinexor.

In some embodiments, the additional therapeutic agent is a fractalkine ligand inhibitor, such as KAND-567.

In some embodiments, the additional therapeutic agent is a FYVE finger phosphoinositide kinase inhibitor/IL-12 receptor antagonist/IL-23 antagonist, such as apilimod dimesylate.

In some embodiments, the additional therapeutic agent is a GABA A receptor modulator, such as brexanolone.

In some embodiments, the additional therapeutic agent is a glucocorticoid receptor agonist, such as ciclesonide, hydrocortisone, dexamethasone, dexamethasone phosphate, or 101-PGC-005.

In some embodiments, the additional therapeutic agent is a GM-CSF receptor agonist, such as sargramostim.

In some embodiments, the additional therapeutic agent is a GPCR agonist, such as esuberaprost sodium.

In some embodiments, the additional therapeutic agent is a Griffithsin modulator, such as Q-Griffithsin.

In some embodiments, the additional therapeutic agent is a leukotriene D4 antagonist, such as montelukast.

In some embodiments, the additional therapeutic agent is a histamine H1 receptor antagonist, such as ebastine, tranilast, levocetirizine dihydrochloride.

In some embodiments, the additional therapeutic agent is a histamine H2 receptor antagonist, such as famotidine.

In some embodiments, the additional therapeutic agent is a heat shock protein stimulator/insulin sensitizer/PARP inhibitor, such as BGP-15.

In some embodiments, the additional therapeutic agent is a histone inhibitor, such as STC-3141.

In some embodiments, the additional therapeutic agent is a histone deacetylase-6 inhibitor, such as CKD-506.

In some embodiments, the additional therapeutic agent is a HIF prolyl hydroxylase-2 inhibitor, such as desidustat.

In some embodiments, the additional therapeutic agent is an HIF prolyl hydroxylase inhibitor, such as vadadustat.

In some embodiments, the additional therapeutic agent is an IL-8 receptor antagonist, such as reparixin.

In some embodiments, the additional therapeutic agent is an IL-7 receptor agonist, such as CYT-107.

In some embodiments, the additional therapeutic agent is an IL-7 receptor agonist/interleukin-7 ligand, such as efineptakin alfa.

In some embodiments, the additional therapeutic agent is an IL-22 agonist, such as efmarodocokin alfa.

In some embodiments, the additional therapeutic agent is an IL-22 agonist/interleukin 22 ligand, such as F-652.

In some embodiments, the additional therapeutic agent is targeted to IL-33, such as tozorakimab.

In some embodiments, the additional therapeutic is an IL-15 agonist such as nogapendekin alfa.

In some embodiments, the additional therapeutic agent is an integrin alpha-V/beta-1 antagonist/integrin alpha-V/beta-6 antagonist, such as bexotegrast.

In some embodiments, the additional therapeutic agent is an interferon alpha 2 ligand, such as interferon alfa-2b or Virafin.

In some embodiments, the additional therapeutic agent is an interferon beta ligand, such as interferon beta-1a follow-on biologic, interferon beta-1b, or SNG-001.

In some embodiments, the additional therapeutic agent is an interferon receptor modulator, such as peginterferon lambda-1a.

In some embodiments, the additional therapeutic agent is an interleukin-2 ligand, such as aldesleukin.

In some embodiments, the additional therapeutic agent is an IRAK-4 protein kinase inhibitor, such as zimlovisertib.

In some embodiments, the additional therapeutic agent is a JAK inhibitor, for example the additional therapeutic agent is baricitinib, filgotinib, jaktinib, tofacitinib, or nezulcitinib (TD-0903).

In some embodiments, the additional therapeutic agent is a neutrophil elastase inhibitor, such as alvelestat.

In some embodiments, the additional therapeutic agent is a lung surfactant associated protein D modulator, such as AT-100.

In some embodiments, the additional therapeutic agent is a plasma kallikrein inhibitor, such as donidalorsen.

In some embodiments, the additional therapeutic agent is a lysine specific histone demethylase 1/MAO B inhibitor, such as vafidemstat.

In some embodiments, the additional therapeutic agent is a Mannan-binding lectin serine protease inhibitor, such as conestat alfa.

In some embodiments, the additional therapeutic agent is a maxi K potassium channel inhibitor, such as ENA-001.

In some embodiments, the additional therapeutic agent is a MEK protein kinase inhibitor, such as zapnometinib.

In some embodiments, the additional therapeutic agent is a MEK-1 protein kinase inhibitor/Ras gene inhibitor, such as antroquinonol.

In some embodiments, the additional therapeutic agent is a melanocortin MC1 receptor agonist, such as PL-8177.

In some embodiments, the additional therapeutic agent is a melanocortin MC1/MC3 receptor agonist, such as resomelagon acetate.

In some embodiments, the additional therapeutic agent is a matrix metalloprotease-12 inhibitor, such as FP-025.

In some embodiments, the additional therapeutic agent is a NACHT LRR PYD domain protein 3 inhibitor, such as dapansutrile, DFV-890, or ZYIL-1.

In some embodiments, the additional therapeutic agent is a NADPH oxidase inhibitor, such as isuzinaxib.

In some embodiments, the additional therapeutic agent is a neuropilin 2 modulator, such as efzofitimod.

In some embodiments, the additional therapeutic agent is an NK1 receptor antagonist, such as aprepitant or tradipitant.

In some embodiments, the additional therapeutic agent is an NMDA receptor antagonist, such as transcrocetin or ifenprodil.

In some embodiments, the additional therapeutic agent is a nuclear factor kappa B inhibitor/p38 MAP kinase inhibitor, such as zenuzolac.

In some embodiments, the additional therapeutic agent is an ornithine decarboxylase inhibitor, such as eflornithine.

In some embodiments, the additional therapeutic agent is an opioid receptor sigma antagonist 1, such as MR-309.

In some embodiments, the additional therapeutic agent is a PGD2 antagonist, such as asapiprant.

In some embodiments, the additional therapeutic agent is a PDGF receptor antagonist/TGF beta receptor antagonist/p38 MAP kinase inhibitor, such as deupirfenidone.

In some embodiments, the additional therapeutic agent is a phospholipase A2 inhibitor, such as varespladib methyl.

In some embodiments, the additional therapeutic agent is a phosphoinositide 3-kinase inhibitor/mTOR complex inhibitor, such as dactolisib.

In some embodiments, the additional therapeutic agent is a mTOR inhibitor, such as sirolimus.

In some embodiments, the additional therapeutic agent is a phosphoinositide-3 kinase delta/gamma inhibitor, such as duvelisib.

In some embodiments, the additional therapeutic agent is a plasminogen activator inhibitor 1 inhibitor, such as TM-5614.

In some embodiments, the additional therapeutic agent is a protein tyrosine phosphatase beta inhibitor, such as razuprotafib.

In some embodiments, the additional therapeutic agent is a RIP-1 kinase inhibitor, such as DNL-758 or SIR-0365.

In some embodiments, the additional therapeutic agent is a Rev protein modulator, such as obefazimod.

In some embodiments, the additional therapeutic agent is an S phase kinase associated protein 2 inhibitor, such as niclosamide, SCAI-502 or DWRX-2003.

In some embodiments, the additional therapeutic agent is a signal transducer CD24 stimulator, such as EXO-CD24.

In some embodiments, the additional therapeutic agent is a sodium glucose transporter-2 inhibitor, such as dapagliflozin propanediol.

In some embodiments, the additional therapeutic agent is a sodium channel stimulator, such as solnatide.

In some embodiments, the additional therapeutic agent is a sphingosine-1-phosphate receptor-1 agonist/sphingosine-1-phosphate receptor-5 agonist, such as ozanimod.

In some embodiments, the additional therapeutic agent is a non-steroidal anti-inflammatory drug, such as Ampion.

In some embodiments, the additional therapeutic agent is a superoxide dismutase stimulator, such as avasopasem manganese.

In some embodiments, the additional therapeutic agent is a Syk tyrosine kinase inhibitor, such as fostamatinib disodium.

In some embodiments, the additional therapeutic agent is a Tie2 tyrosine kinase receptor agonist, such as AV-001.

In some embodiments, the additional therapeutic agent is a TGFB2 gene inhibitor, such as trabedersen.

In some embodiments, the additional therapeutic agent is a tissue factor inhibitor, such as AB-201.

In some embodiments, the additional therapeutic agent is a TLR-3 agonist, such as rintatolimod.

In some embodiments, the additional therapeutic agent is a TLR-4 antagonist, such as ApTLR-4FT, EB-05, or eritoran.

In some embodiments, the additional therapeutic agent is a TLR-7/8 antagonist, such as enpatoran.

In some embodiments, the additional therapeutic agent is a TLR-2/6 agonist, such as INNA-051.

In some embodiments, the additional therapeutic agent is a TLR-7 agonist, such as PRTX-007 or APR-002.

In some embodiments, the additional therapeutic agent is a TLR agonist, such as PUL-042.

In some embodiments, the additional therapeutic agent is a TLR-4 agonist, such as REVTx-99.

In some embodiments, the additional therapeutic agent is a TLR-2/4 antagonist, such as VB-201.

In some embodiments, the additional therapeutic agent is a TNF alpha ligand inhibitor, such as pegipanermin.

In some embodiments, the additional therapeutic agent is a type I IL-1 receptor antagonist, such as anakinra.

In some embodiments, the additional therapeutic agent is a TREM receptor 1 antagonist, such as nangibotide.

In some embodiments, the additional therapeutic agent is a trypsin inhibitor, such as ulinastatin.

In some embodiments, the additional therapeutic agent is a tubulin inhibitor such as sabizabulin, CCI-001, PCNT-13, CR-42-24, albendazole, entasobulin, SAR-132885, or ON-24160.

In some embodiments, the additional therapeutic agent is a VIP receptor agonist, such as aviptadil.

In some embodiments, the additional therapeutic agent is a xanthine oxidase inhibitor, such as oxypurinol.

In some embodiments, the additional therapeutic agent is a vasodilator, such as iloprost, epoprostenol (VentaProst), zavegepant, TXA-127, USB-002, ambrisentan, nitric oxide nasal spray (NORS), pentoxifylline, propranolol, RESP301, sodium nitrite, or dipyridamole.

In some embodiments, the additional therapeutic agent is a vitamin D3 receptor agonist, such as cholecalciferol.

In some embodiments, the additional therapeutic agent is a zonulin inhibitor, such as larazotide acetate.

In some embodiments, the additional therapeutic agent is a synthetic retinoid derivative, such as fenretinide.

In some embodiments, the additional therapeutic agent is a glucose metabolism inhibitor such as WP-1122 or WP-1096.

In some embodiments, the additional therapeutic agent is adalimumab, AT-H201, 2-deoxy-D-glucose, AD-17002, AIC-649, AMTX-100, astodrimer, AZD-1656, belapectin, bitespiramycin, bucillamine, budesonide, CNM-AgZn-17, Codivir, CT-38, danicopan, didodecyl methotrexate, DW-2008S (DW-2008), EDP-1815, EG-009A, Fabencov, Gamunex, genistein, GLS-1200, hzVSF-v13, imidazolyl ethanamide pentandioic acid, IMM-101, MAS-825, MRG-001, Nasitrol, Nylexa, olverembatinib, OP-101, OPN-019, Orynotide rhesus theta defensin-1, pyronaridine+artesunate, dapsone, RPH-104, sodium pyruvate, Sulforadex, tafenoquine, TB-006, telacebec, Tempol, TL-895, thimesoral, trimodulin, XC-221, XC-7, zunsemetinib, metformin glycinate, lucinactant, EOM-613, mosedipimod, ivermectin, leflunomide, ibudilast, RBT-9, raloxifene, prothione, gemcabene, or idronoxil.

In some embodiments, the additional therapeutic agent is a CD73 antagonist, such as AK-119.

In some embodiments, the additional therapeutic agent is a CD95 protein fusion, such as asunercept.

In some embodiments, the additional therapeutic agent is a complement factor C2 modulator, such as ARGX-117.

In some embodiments, the additional therapeutic agent is a complement C3 inhibitor, such as AMY-101 or NGM-621.

In some embodiments, the additional therapeutic agent is a CXC10 chemokine ligand inhibitor, such as EB-06.

In some embodiments, the additional therapeutic agent is a cytotoxic T-lymphocyte protein-4 fusion protein, such as abatacept In some embodiments, the additional therapeutic agent is an anti-S. Aureus antibody, such as tosatoxumab.

In some embodiments, the additional therapeutic agent is an anti-LPS antibody, such as IMM-124-E.

In some embodiments, the additional therapeutic agent is an adrenomedullin ligand inhibitor, such as enibarcimab.

In some embodiments, the additional therapeutic agent is a basigin inhibitor, such as meplazumab.

In some embodiments, the additional therapeutic agent is a CD3 antagonist, such as foralumab.

In some embodiments, the additional therapeutic agent is a connective tissue growth factor ligand inhibitor, such as PRS-220, pamrevlumab.

In some embodiments, the additional therapeutic agent is a complement C5a factor inhibitor, such as BDB-1 or vilobelimab.

In some embodiments, the additional therapeutic agent is a complement C5 factor inhibitor, such as ravulizumab.

In some embodiments, the additional therapeutic agent is a mannan-binding lectin serine protease-2 inhibitor, such as narsoplimab.

In some embodiments, the additional therapeutic agent is a GM-CSF modulator, such as STSA-1005, gimsilumab, namilumab, plonmarlimab, otilimab, or lenzilumab.

In some embodiments, the additional therapeutic agent is a heat shock protein inhibitor/IL-6 receptor antagonist, such as siltuximab.

In some embodiments, the additional therapeutic agent is an IL-6 receptor antagonist, such as clazakizumab, levilimab, olokizumab, tocilizumab, or sirukumab.

In some embodiments, the additional therapeutic agent is an IL-8 receptor antagonist, such as BMS-986253.

In some embodiments, the additional therapeutic agent is an interleukin-1 beta ligand inhibitor, such as canakinumab.

In some embodiments, the additional therapeutic agent is an interferon gamma ligand inhibitor, such as emapalumab.

In some embodiments, the additional therapeutic agent is an anti-ILT7 antibody, such as daxdilimab.

In some embodiments, the additional therapeutic agent is a monocyte differentiation antigen CD14 inhibitor, such as atibuclimab.

In some embodiments, the additional therapeutic agent is a plasma kallikrein inhibitor, such as lanadelumab.

In some embodiments, the additional therapeutic agent is a platelet glycoprotein VI inhibitor, such as glenzocimab.

In some embodiments, the additional therapeutic agent is a T-cell differentiation antigen CD6 inhibitor, such as itolizumab.

In some embodiments, the additional therapeutic agent is a TNF alpha ligand inhibitor/TNF binding agent, such as infliximab.

In some embodiments, the additional therapeutic agent is an anti-LIGHT antibody, such as AVTX-002.

In some embodiments, the additional therapeutic agent is IMC-2 (valacyclovir+celecoxib), or AXA-1125.

In some embodiments, the additional therapeutic agent is COVID-HIG.

In some embodiments, the solid dosage forms of the disclosure are co-administered with one or more agents useful for the treatment and/or prophylaxis of COVID-19.

Non-limiting examples of such agents include corticosteroids, such as dexamethasone, hydrocortisone, methylprednisolone, or prednisone; interleukin-6 (IL-6) receptor blockers, such as tocilizumab or sarilumab; Janus kinase (JAK) inhibitors, such as baricitinib, ruxolitinib, or tofacitinib; and antiviral agents, such as molnupiravir, sotrovimab, or remdesivir.

In further embodiments, the solid oral dosage forms of the disclosure are co-administered with two or more agents useful for the treatment of COVID-19. Agents useful for the treatment and/or prophylaxis of COVID-19 include but are not limited to nirmatrelvir and ritonavir, casirivimab and imdevimab, or ruxolitinib and tofacitinib.

In some embodiments, the additional therapeutic agent is an antiviral agent. In some embodiments, the antiviral agent is an entry inhibitor. In some embodiments, the antiviral agent is a protease inhibitor. In some embodiments, the antiviral agent is an RNA polymerase inhibitor. In some embodiments, the additional therapeutic agent is an RNA-dependent RNA polymerase (RdRp) inhibitor.

In some embodiments, the antiviral agent is selected from angiotensin converting enzyme 2 inhibitors, angiotensin converting enzyme 2 modulators, angiotensin converting enzyme 2 stimulators, angiotensin II AT-2 receptor agonists, angiotensin II AT-2 receptor antagonists, angiotensin II receptor modulators, coronavirus nucleoprotein modulators, coronavirus small envelope protein modulators, coronavirus spike glycoprotein inhibitors, coronavirus spike glycoprotein modulators, SARS-CoV-2 envelope small membrane protein inhibitors, SARS-CoV-2 envelope small membrane protein modulators, SARS-CoV-2 MPro inhibitors, SARS-CoV-2 non-structural protein 8 modulators, SARS-CoV-2 nucleoprotein inhibitors, SARS-CoV-2 nucleoprotein modulators, SARS-CoV-2 protein 3a inhibitors, SARS-CoV-2 replicase polyprotein 1a inhibitors, SARS-CoV-2 replicase polyprotein 1a modulators, SARS-CoV-2 replicase polyprotein 1ab inhibitors, SARS-CoV-2 replicase polyprotein 1ab modulators, SARS-CoV-2 spike glycoprotein inhibitors, SARS-CoV-2 spike glycoprotein modulators, SARS-CoV-2 structural glycoprotein modulators, papain inhibitors, protease inhibitors, protease modulators, RNA polymerase inhibitors, RNA polymerase modulators, RNA-dependent RNA polymerase (RdRp) inhibitors, SARS coronavirus 3C protease like inhibitors, SARS-CoV-2 nsp14 methyltransferase enzyme inhibitor, 3CLpro/Mpro inhibitors, serine protease inhibitors, transmembrane serine protease 2 inhibitors, transmembrane serine protease 2 modulators, viral envelope protein inhibitors, viral protease inhibitors, viral protease modulators, viral protein target modulators, viral ribonuclease inhibitors, and viral structural protein modulators.

In some embodiments, the additional therapeutic agent is an entry inhibitor. For example, in some embodiments the additional therapeutic agent is an ACE2 inhibitor, a fusion inhibitor, or a protease inhibitor.

In some embodiments, the additional therapeutic agent is an angiotensin converting enzyme 2 inhibitor, such as SBK-001.

In some embodiments, the additional therapeutic agent is an angiotensin converting enzyme 2 modulator, such as neumifil or JN-2019.

In some embodiments, the additional therapeutic agent is an entry inhibitor such as MU-UNMC-1.

In some embodiments, the additional therapeutic agent is an angiotensin converting enzyme 2 stimulator, such as alunacedase alfa.

In some embodiments, the additional therapeutic agent is an angiotensin II AT-2 receptor agonist, such as VP-01.

In some embodiments, the additional therapeutic agent is an ACE II receptor antagonist, such as DX-600.

In some embodiments, the additional therapeutic agent is an angiotensin II receptor modulator, such as TXA-127.

In some embodiments, the additional therapeutic agent is a transmembrane serine protease 2 modulator, such as BC-201.

In some embodiments, the additional therapeutic agent is a viral envelope protein inhibitor, such as MXB-9 or MXB-004.

In some embodiments, the additional therapeutic agent is a RNAi agent such as ARO-COV or SNS-812.

In some embodiments, the additional therapeutic agent is a vaccine. For example, in some embodiments, the additional therapeutic agent is a DNA vaccine, RNA vaccine, live-attenuated vaccine, inactivated vaccine (i.e., inactivated SARS-CoV-2 vaccine), therapeutic vaccine, prophylactic vaccine, protein-based vaccine, viral vector vaccine, cellular vaccine, or dendritic cell vaccine.

In some embodiments, the additional therapeutic agent is a vaccine such as tozinameran, NVX-CoV2373, elasomeran, KD-414, Ad26.COV2-S, Vaxzevria, SCB-2019, AKS-452, VLA-2001, HDT-301, 5-268019, MVC-COV1901, mRNA-1273.214, mRNA-1273.213, mRNA-1273.222, NVX-CoV2515, Covaxin, BBIBP-CorV, GBP-510, mRNA-1273.351+mRNA-1273.617 (SARS-CoV-2 multivalent mRNA vaccine, COVID-19), Ad5-nCoV, Omicron-based COVID-19 vaccine (mRNA vaccine, COVID-19), mRNA-1073, mRNA-1273.214, mRNA-1230, mRNA-1283, Omicron-based COVID-19 vaccine, SARS-CoV-2 Protein Subunit Recombinant Vaccine, Sputnik M, ZyCoV-D, COVID-19 XWG-03, mRNA-1273.529, mRNA-1010, CoronaVac, AZD-2816, Sputnik V, inactivated SARS-CoV-2 vaccine (Vero cell, COVID-19), DS-5670, PHH-1V, INO-4800, UB-612, coronavirus vaccine (whole-virion, inactivated/purified), ReCOV, MT-2766, ARCT-154, SP-0253, CORBEVAX, mRNA-1273.211, ZF-2001, Sputnik Light, recombinant protein vaccine (COVID-19/SARS-CoV-2 infection), VSV vector-based vaccine targeting spike glycoprotein (COVID-19), VLA-2101, GRT-R912, GRAd-COV2, VPM-1002, COViran Barekat, Ad5-nCoV-IH, ARCoV, Covax-19, recombinant SARS-CoV-2 vaccine (protein subunit/CHO cell, COVID-19), BBV-154, RAZI Cov Pars, COVID-19 vaccine (inactivated/Vero cells/intramuscular, SARS-CoV-2 infection), COVID-19 vaccine (inactivated, Vero cells/intramuscular), BNT-162b2s01, BNT-162b4, BNT-162b5, BNT-162b2 Omi, BNT-162b2 bivalent, CIGB-66, mRNA-1273.617, *Mycobacterium* w, ERUCOV-VAC, AG-0301-COVID19, fakhravac, AV-COVID-19, peptide vaccine (COVID-19), Nanocovax, SARS-CoV-2 vaccine (inactivated/Vero cells/intramuscular, COVID-19), QAZCOVID-IN, S-875670 nasal vaccine, VTP-500, or BNT162b5.

In some embodiments, the additional therapeutic agent is a protease inhibitor. For example, in some embodiments the additional therapeutic agent is a 3C-like cysteine protease inhibitor (3CLpro, also called Main protease, Mpro), a papain-like protease inhibitor (PLpro), serine protease inhibitor, or transmembrane serine protease 2 inhibitor (TMPRSS2).

In some embodiments, the additional therapeutic agent is a 3CLpro/Mpro inhibitor, such as CDI-873, GC-373, GC-376, PBI-0451, UCI-1, bofutrelvir (FB-2001, DC-402234), DC-402267, GDI-4405, RAY-1216, MPI-8, SH-879, SH-580, EDP-235, VV-993, CDI-988, MI-30, nirmatrelvir, ensitrelvir, ASC-11, EDDC-2214, SIM-0417, CDI-45205, COR-803, ALG-097111, TJC-642, CVD-0013943, eravacycline, cynarine, or prexasertib.

In some embodiments, the additional therapeutic agent is a papain-like protease inhibitor (PLpro), such as SBFM-PL4 or GRL-0617.

In some embodiments, the additional therapeutic agent is a SARS-CoV-2 helicase Nsp13 inhibitor, such as EIS-4363.

In some embodiments, the additional therapeutic agent is a SARS-CoV-2 helicase Nsp14 inhibitor, such as TO-507.

In some embodiments, the additional therapeutic agent is a SARS-CoV-2 spike (S) and protease modulator, such as ENU-200.

In some embodiments, the additional therapeutic agent is a protease inhibitor, such as ALG-097558 or MRX-18.

In some embodiments, the additional therapeutic agent is a serine protease inhibitor, such as upamostat, nafamostat, camostat mesylate, nafamostat mesylate, or camostat.

In some embodiments, the additional therapeutic agent is a 3CLpro/transmembrane serine protease 2 inhibitor, such as SNB-01 (pentarlandir) or SNB-02.

In some embodiments, the additional therapeutic agent is a viral protease inhibitor, such as Pan-Corona, Cov-X, or bepridil.

In some embodiments, the additional therapeutic agent is an RNA polymerase inhibitor. For example, in some embodiments, the additional therapeutic agent is an RNA polymerase inhibitor, or an RNA-dependent RNA polymerase (RdRp) inhibitor.

In some embodiments, the additional therapeutic agent is an RNA-dependent RNA polymerase (RdRp) inhibitor, such as remdesivir, NV-CoV-2-R, NV-CoV-1 encapsulated remdesivir, GS-621763, DEP remdesivir, ATV-006, VV-116, LGN-20, CMX-521 and compounds disclosed in WO2022142477, WO2021213288, WO2022047065.

In some embodiments, the additional therapeutic agent is an RNA polymerase inhibitor, such as molnupiravir (EIDD-2801), favipiravir, bemnifosbuvir, sofosbuvir, ASC-10, or galidesivir.

In some embodiments, the additional therapeutic agent is viral entry inhibitor, such as brilacidin.

In some embodiments, the additional therapeutic agent is an antibody that binds to a coronavirus, for example an antibody that binds to SARS or MERS.

In some embodiments, the additional therapeutic agent is an antibody, for example a monoclonal antibody. For example, the additional therapeutic agent is an antibody against SARS-CoV-2, neutralizing nanobodies, antibodies that target the SARS-CoV-2 spike protein, fusion proteins, multispecific antibodies, and antibodies that can neutralize SARS-CoV-2 (SARS-CoV-2 neutralizing antibodies).

In some embodiments, the additional therapeutic agent is an antibody that targets specific sites on ACE2. In some embodiments, the additional therapeutic agent is a polypeptide targeting SARS-CoV-2 spike protein (S-protein).

In some embodiments, the additional therapeutic agent is a SARS-CoV-2 virus antibody.

In some embodiments, the antibody is ABBV-47D11, COVI-GUARD (STI-1499), C144-LS+C135-LS, DXP-604, JMB-2002, LY-CovMab, bamlanivimab (LY-CoV555), GIGA-2050, IBI-314, S309, SAB-185, etesevimab (CB6), COR-101, JS016, VNAR, VIR-7832, and/or sotrovimab (VIR-7831), casirivimab+imdevimab (REGN-COV2 or REGN10933+RGN10987), BAT2020, BAT2019, 47D11, YBSW-015, or PA-001.

In some embodiments, the additional therapeutic agent is STI-9199 (COVI-SHIELD), STI-9167 or AR-701 (AR-703 and AR-720).

In some embodiments, the additional therapeutic agent is BRII-196, BRII-198, ADG-10, adintrevimab (ADG-20), ABP-300, BA-7208, BI-767551, BHV-1200, CT-P63, JS-026, sotrovimab (GSK-4182136), tixagevimab+cilgavimab (AZD-7442), regdanvimab, SAB-301, AOD-01, plutavimab (COVI-AMG), 9MW-3311 (MW-33), DXP-593, BSVEQAb, anti-SARS-CoV-2 IgY, COVID-EIG, CSL-760, F-61, REGN-3048-3051, SARS-CoV-2 monoclonal antibodies (COVID-19, ADM-03820), enuzovimab (HFB-30132A), INM-005, SCTA01, TY-027, XAV-19, amubarvimab+romlusevimab, SCTA-01, bebtelovimab, beludavimab, IBI-0123, IGM-6268. FYB-207, FS-2101, RBT-0813, REGN-14256, REGN-14284, SPKM-001, XVR-011, TB202-3, TB181-36, TB339-031, LMN-301, LQ-050, COVAB-36, MAD-0004J08, STI-2099, TATX-03, TZLS-501, ZCB-11 or ACV-200-17.

In some embodiments, the additional therapeutic agent is an engineered ACE-2-IgG1-Fc-fusion protein targeting SARS-Cov-2 RBD, such as EU-129, bivalent ACE2-IgG Fc null fusion protein (SI-F019).

In some embodiments, the additional therapeutic agent is an ACE2-Fc receptor fusion protein, such as HLX-71.

In some embodiments, the additional therapeutic agent is ensovibep.

In some embodiments, the additional therapeutic agent is SYZJ-001.

In some embodiments, the additional therapeutic agent is an HIV-1 protease inhibitor, such as ASC-09F (ASC-09+ritonavir) or lopinavir+ritonavir.

In some embodiments, the additional therapeutic agent is a non-nucleoside reverse transcriptase inhibitor, such as elsulfavirine.

In some embodiments, the additional therapeutic agent is a nucleoside reverse transcriptase inhibitor, such as azvudine.

In some embodiments, the additional therapeutic agent is Abbv-990, BAT-2022, NED-260, ALG-097431, bardoxolone, delcetravir, ESFAM-289, ENOB-CV-01, ENOB-CV-11, EIS-10700, beta-521, SIM-0417, molnupiravir, Pan-Corona, Tollovir, nirmatrelvir+ritonavir (Paxlovid®), favipiravir, GC-376, upamostat, LeSoleil-01, LeSoleil-02+, benfovir, VV-116, VV-993, SNB-01, EDP-235, Cov-X, ensitrelvir, MPI-8, masitinib, ALG-097558, ASC-11, PBI-0451, nafamostat, nafamostat mesylate, CDI-45205, COR-803, ALG-097111, BC-201, SH-879, CDI-873, CDI-988, remdesivir, NV-CoV-2-R, NV-CoV-1 encapsulated remdesivir, NA-831+remdesivir, DEP remdesivir, GS-621763, GLS-5310, bemnifosbuvir, QLS-1128, ASC-10, SBFM-PL4, camostat mesylate, UCI-1, FB-2001 (DC-402234), ebselen, SH-580, LeSoleil-01, LeSoleil-02+, MRX-18, MXB-9, MI-09, MI-30, SNB-02, SJP-002C, TJC-642, ENU-200, CVD-0013943, bepridil, MXB-004, eravacycline, GRL-0617, camostat, GC-373, nitazoxanide, cynarine, prexasertib, RAY-1216, SACT-COVID-19, MP-18, EIDD-1931, EDDC-2214, nitric oxide, apabetalone, AnQlar, SBK-001, LQ-050, CG-SpikeDown, bamlanivimab, HLX-71, HT-002, HY-209, HY-3000, FYB-207, ensovibep, SYZJ-001, EU-129, neumifil, JN-2019, AR-701, vostesyl, PLM-402, PJS-539, CTB-ACE2, TB181-36, TB202-3, ABP-300, XVR-011, MSP-008-22, MU-UNMC-1, MU-UNMC-2, alunacedase alfa, VP-01, TRV-027, DX-600, TXA-127, NVX-CoV2515, riamilovir, tozinameran, elasomeran, Ad5-nCoV, BBIBP-CorV, CoronaVac, MVC-COV1901, NVX-CoV2373, sotrovimab, Sputnik V, TEE-001, Tyme-19, Vaxzevria, ZF-2001, or ZyCoV-D.

It is also possible to combine the solid oral dosage forms disclosed herein with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a solid oral forms disclosed herein with one or more other active therapeutic agents generally refers to simultaneous or sequential administration of a the solid oral dosage form disclosed herein and one or more other active therapeutic agents, such that therapeutically effective amounts of the compound of Formula I and one or more other active therapeutic agents are both present in the body of the patient.

Co-administration includes administration of unit dosages of the solid oral dosage forms disclosed herein before or after administration of unit dosages of one or more other active therapeutic agents, for example, administration of the solid oral dosage forms disclosed herein within seconds, minutes, or hours of the administration of one or more other active therapeutic agents. For example, a unit dose of a solid oral dosage forms disclosed herein can be administered first, followed within seconds or minutes by administration of a unit dose of one or more other active therapeutic agents. Alternatively, a unit dose of one or more other therapeutic agents can be administered first, followed by administration of a unit dose of solid oral dosage forms disclosed herein within seconds or minutes. In some cases, it may be desirable to administer a unit dose of a solid oral dosage forms disclosed herein first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of solid oral dosage forms disclosed herein.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect, which is greater than the predicted purely additive effects of the individual compounds of the combination.

General

The term "pharmaceutically acceptable" with respect to a substance refers to that substance which is generally regarded as safe and suitable for use without undue toxicity, irritation, allergic response, and the like, commensurate with a reasonable benefit/risk ratio. "Pharmaceutically acceptable" with regard to excipients includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, PA, (2005), at p. 732, Table 38-5, both of which are hereby incorporated by reference herein.

The term "comprise" and variations thereof, such as "comprises" and "comprising", are to be construed in an open, inclusive sense, that is as "including, but not limited to".

The term "about" used in connection with a quantity is inclusive of the stated value and has the meaning dictated by the context (e.g., includes the degree of error associated with measurement of the particular quantity). For example, in certain nonlimiting example the term "about" in relation to a numerical value x refers to x±5% or x±1%.

"% w/w" or "wt %" means the weight of a component as a percentage of the total weight of e.g. a dosage form in which the component is present. For example, a composition comprising "5% w/w X" refers to a composition in which the weight of component X is 5% of the total weight of the composition. Unless specifically stated otherwise, where the dosage form is coated, it is to be understood that a reference to % weight is calculated with respect to the tablet core weight. It will be appreciated that where ranges of % weight are provided for different components of the composition, the total % weight of the components will add up to 100%. In particular, when the upper limits of each range, when added together, exceed 100%, it will be understood that the actual amounts of components present in the composition will be selected so that the total weight % totals 100% and does not exceed it.

The "tablet core weight" as calculated herein is the sum total of (i) the compound of Formula I, (ii) the filler, (iii) the disintegrating agent, and (iv) the lubricant. The core tablet weight does not include the weight of the film coating.

The "tablet weight" as calculated herein is the sum total of (i) the compound of Formula I, (ii) the filler, (iii) the disintegrating agent, (iv) the lubricant, and (v) the film coating.

For example, for a tablet comprising 100 mg of the compound of Formula I, 89 mg filler, 8 mg disintegrating agent, 3 mg lubricant, and 6 mg film coat:

The tablet core weight is 100 mg (Formula I wt.)+89 mg (filler wt.)+8 mg (disintegrating agent wt.)+3 mg (lubricant weight)=200 mg.

The tablet weight is 100 mg (Formula I wt.)+89 mg (filler wt.)+8 mg (disintegrating agent wt.)+3 mg (lubricant weight)+6 mg (film coat w.)=206 mg.

The wt % of the compound of Formula I is 100 mg (Formula I wt.)/200 mg (tablet core weight)=50%.

The wt % of filler is 89 mg (filler wt.)/200 mg (tablet core weight)=44.5%.

The wt % of disintegrating agent is 8 mg (disintegrating agent wt.)/200 mg (tablet core weight)=4%.

The wt % of lubricant is 3 mg (lubricant wt.)/200 mg (tablet core weight)=1.5%.

The wt % of film coat is 6 mg (lubricant wt.)/200 mg (tablet core weight)=3%.

EXAMPLES

Example 1: Compound of Formula I Tablets

Compound of Formula I tablets evaluated were manufactured using a dry granulation/tablet compression/film-coating process train. Dry granulation by roller compaction was selected as the means of combining Formula I with inactive excipients in order to minimize exposure of Formula I to moisture during the granulation process. The overall manufacturing process consisted of co-blending and lubricating Formula I with intragranular excipients, followed by roller compaction and milling. The resulting Formula I granules were then blended and lubricated with extragranular magnesium stearate to produce the Formula I final powder blend, which was compressed into core tablets that were subsequently film-coated (with Opadry® II or QX).

Example 2: Manufacturing Process

The manufacturing/packaging procedure for Formula I tablets is divided into four unit processes:
1. Mixing of Formula I drug substance with intragranular excipients, dry granulation, milling, and blending with extragranular magnesium stearate to yield Formula I final powder blend;
2. Tablet compression to yield tablet cores;
3. Tablet film-coating to yield film-coated tablets; and
4. Packaging.

The manufacturing process steps to produce the final drug product are detailed below.

Formula I Final Powder Blend (Dispensing, Blending, Dry Granulation, Milling, Final Blending)
1. Weigh Formula I drug substance and excipients (microcrystalline cellulose and crospovidone). Adjust the weight of Formula I drug substance based on the drug content factor (DCF), with a concomitant adjustment to the weight of microcrystalline cellulose.
2. Blend Formula I drug substance, microcrystalline cellulose, and crospovidone in a tumble blender.
3. Add the intragranular portion of magnesium stearate to the tumble blender and blend.
4. Dry granulate the resulting blend using a roller compactor.
5. Blend in the extragranular portion of magnesium stearate.

Tableting
6. Compress the Formula I final powder blend to a target total tablet weight of 200 mg with an appropriate main compression force to achieve a target hardness of 7 kP (range: 3 to 15 kP), 700 mg with an appropriate main compression force to achieve a target hardness of 16 kP (range: 8 to 30 kP), or 1000 mg with an appropriate main compression force to achieve a target hardness of 21 kP (range: 10 to 40 kP). See table below for hardness for Formulations.

|  | Average hardness (kP) |
| --- | --- |
| Formulation F1 | 7.1-7.4 |
| Formulation F2 | 21.8-22.4 |
| Formulation F3 | 7.1-7.2 |
| Formulation F4 | 20.2-20.9 |
| Formulation F7 | 21.7-22.3 |

Film-Coating
7. Prepare a suspension of Opadry® II or QX. Film-coat the tablet cores to achieve the target tablet weight gain of 3% (range 2-4%).

Example 3: Stability of the Formula I Tablets

Five film coated tablets were packaged in a 45 cc white, HDPE bottle containing polyester coil. Each bottle was capped using a white, continuous thread, child-resistant polypropylene crew cap with an induction-sealed, aluminum-faced liner. Two stability experiments were then carried out: one at 30° C. and 75% relative humidity (RH) for nine months and one at 40° C. and 75% relative humidity (RH) for six months.

The water content of the initial formulations and the formulations after the stability experiments was measured by Karl Fisher titration. Initial impurity content, assay, and impurities after each of the stability experiments were measured by UPLC. Percentage dissolution at 45 minutes for both the initial formulations and the formulations after the stability experiments was measured using a Type II dissolution apparatus at conditions of 37° C.

The results of the stability experiments are summarized in FIG. 2. It can be seen that all of the tested formulations showed excellent stability and dissolution, both before and after stability testing. Trace degradation was observed over the time course of the stability experiments. The dissolution results demonstrate release of Formula I is ≥94% at 45 minutes for all experiments.

The following formulations/lots were tested.

| Formulation F1 (100 mg Formula I, lot 1): | |
| --- | --- |
| Component | % w/w |
| Intragranular | |
| Formula I (100 mg) | 50.0 |
| MCC | 44.5 |
| Crospovidone | 4.0 |
| Magnesium Stearate | 0.5 |
| Total (IG) | 99.0 |
| EG Magnesium Stearate | 1.0 |
| Total | 100.0 |
| Opadry ® II 85F140073 | 3.0 |

IG: Intragranular
EG: Extragranular
MCC: microcrystalline cellulose

| Formulation F2 (500 mg Formula I, lot 1): | |
| --- | --- |
| Component | % w/w |
| Intragranular | |
| Formula I (500 mg) | 50.0 |
| MCC | 44.5 |
| Crospovidone | 4.0 |
| Magnesium Stearate | 0.5 |
| Total (IG) | 99.0 |
| EG Magnesium Stearate | 1.0 |
| Total | 100.0 |
| Opadry ® II 85F140073 | 3.0 |

IG: Intragranular
EG: Extragranular
MCC: microcrystalline cellulose

| Formulation F3 (100 mg Formula I, lot 2): | |
| --- | --- |
| Component | % w/w |
| Intragranular | |
| Formula I (100 mg) | 50.0 |
| MCC | 44.5 |

Formulation F3 (100 mg Formula I, lot 2):

| Component | % w/w |
|---|---|
| Crospovidone | 4.0 |
| Magnesium Stearate | 0.5 |
| Total (IG) | 99.0 |
| EG Magnesium Stearate | 1.0 |
| Total | 100.0 |
| Opadry ® II 85F140073 | 3.0 |

IG: Intragranular
EG: Extragranular
MCC: microcrystalline cellulose

Formulation F4 (500 mg Formula I, lot 2):

| Component | % w/w |
|---|---|
| Intragranular | |
| Formula I (500 mg) | 50.0 |
| MCC | 44.5 |
| Crospovidone | 4.0 |
| Magnesium Stearate | 0.5 |
| Total (IG) | 99.0 |
| EG Magnesium Stearate | 1.0 |
| Total | 100.0 |
| Opadry ® II 85F140073 | 3.0 |

IG: Intragranular
EG: Extragranular
MCC: microcrystalline cellulose

As shown in FIG. 2, three of the impurities found in the tested formulations were compounds GS 441524 (the parent nucleoside of the compound of Formula I) and compounds A and B. Structures of these compounds are shown below:

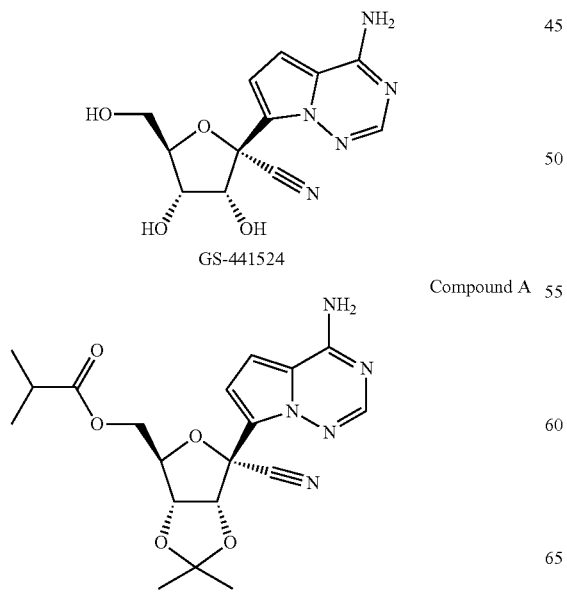

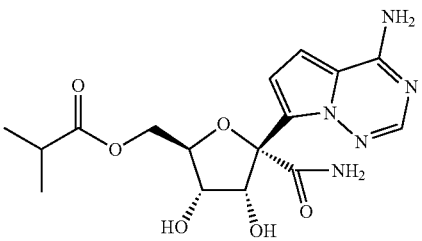

Example 4: Stability of the Formula I Tablets

The stability of the Formula I tablets was tested when stored in 6 mil Aclar, Non-desiccated Bottle, and Open Condition. The stability experiment was carried out at 40° C. and 75% relative humidity (RH) for one or three months.

The appearance of the tablets was recorded both at the start and end of the stability experiment. The water content of the initial formulations and the formulations after the stability experiments was measured by Karl Fisher titration. Initial impurity content and impurities after each of the stability experiments were measured by UPLC. Percentage dissolution at 45 minutes for both the initial formulations and the formulations after the stability experiments was measured as follows:

Formulation F5: dissolution measured using a Type 2 apparatus, 20 mM of sodium acetate at a pH of 4.5 with 900 mL of 0.5% TWEEN 20 at 75 rpm. Dissolution was measured at a temperature of 37° C.

Formulation F6: dissolution measured using a Type 2 apparatus, 25 mM of sodium acetate at a pH of 4.5 with 1000 mL of 0.25% SLS at 75 rpm. Dissolution was measured at a temperature of 37° C.

Formulation F7: dissolution measured using a Type 2 apparatus, 20 mM of sodium acetate at a pH of 4.5 with 1000 mL of 0.5% TWEEN 20 at 75 rpm. Dissolution was measured at a temperature of 37° C.

The results of the stability experiments are summarized in FIG. 3. As seen, Formula I tablets are chemically and physically stable when stored in 6 mil Aclar, non-desiccated bottle, and open condition with less than 0.1% degradation observed. Equilibration to water content of ~4.5% at 75% RH is observed. Dissolution results demonstrate that Formula I tablets fully release (≥97%) by 45 minutes.

The following formulations/lots were tested.

Formulation F5:

| Component | % w/w |
|---|---|
| Intragranular | |
| Formula I (350 mg) | 50.0% |
| MCC | 45.0% |
| Crospovidone | 4.0% |
| Magnesium Stearate | 0.5% |
| Total (IG) | 99.5% |
| EG Magnesium Stearate | 0.5% |
| | 100.0% |
| Opadry ® QX Yellow 321A120059 | 3.0 |

IG: Intragranular
EG: Extragranular
MCC: microcrystalline cellulose

| Formulation F6: | |
|---|---|
| Component | % w/w |
| Intragranular | |
| Formula I (700 mg) | 50.0% |
| MCC | 45.0% |
| Crospovidone | 4.0% |
| Magnesium Stearate | 0.5% |
| EG Magnesium Stearate | 0.5% |
| Total | 100.0% |
| Opadry ® II Yellow 85F12305 | 3.0 |

EG: Extragranular
MCC: microcrystalline cellulose

| Formulation F7: | |
|---|---|
| Component | % w/w |
| Intragranular | |
| Formula I, 500 mg | 50.0% |
| MCC | 45.0% |
| Crospovidone | 4.0% |
| Magnesium Stearate | 0.5% |
| | 99.5% |
| EG Magnesium Stearate | 0.5% |
| | 100.0% |
| Opadry ® QX Yellow 321A120059 | 3.0 |

EG: Extragranular
MCC: microcrystalline cellulose

As shown in FIG. 3, three of the impurities found in the tested formulations were compounds GS 441524 and compounds C and D. Structures of these compounds are shown below:

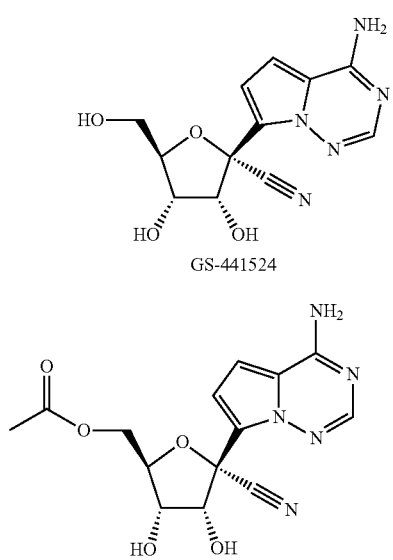

GS-441524

Compound C

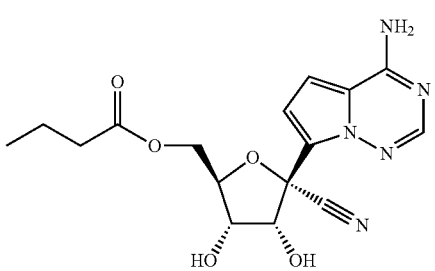

Compound D

Example 5: Stability of Formulation F8

The stability of Formulation F8 was tested when stored at elevated temperatures without a desiccant. The results of the stability experiments are shown in FIGS. 4-6. Two of the impurities found in the tested formulations were GS-441524 and compound D.

| Formulation F8: | |
|---|---|
| Component | % w/w |
| Intragranular | |
| Formula I, 175 mg | 50.0% |
| MCC | 45.0% |
| Crospovidone | 4.0% |
| Magnesium Stearate | 0.5% |
| | 99.5% |
| EG Magnesium Stearate | 0.5% |
| | 100.0% |
| Opadry ® QX White 321A180025 | 3.0 |

EG: Extragranular
MCC: microcrystalline cellulose

All publications, patents, and patent applications are incorporated herein by reference in their entirety, as though individually incorporated by reference. The invention has been described with reference to various specific and preferred embodiments and techniques. However, it should be understood that many variations and modifications may be made while within the spirit and scope of the invention.

The invention claimed is:

1. A pharmaceutical formulation, comprising:
(i) about 175 mg or about 350 mg of a compound expressed by formula I, or a pharmaceutically acceptable salt thereof;

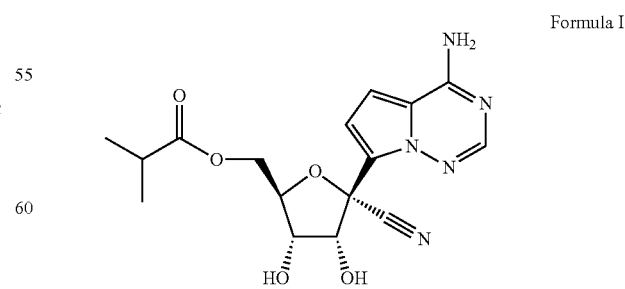

Formula I (ii) a filler;
(iii) a disintegrating agent; and
(iv) a lubricant;

wherein the compound of Formula I is present in an amount of about 45 wt % to about 55 wt %.

2. The pharmaceutical formulation of claim 1, wherein the pharmaceutical formulation comprises:
   (i) the compound of Formula I in an amount of about 50 wt %;
   (ii) the filler in an amount of about 44 wt % to about 46 wt %;
   (iii) the disintegrating agent in an amount of about 3 wt % to about 5 wt %; and
   (iv) the lubricant in an amount of about 0.5 wt % to about 2 wt %.

3. The pharmaceutical formulation according to claim 1, wherein the filler is microcrystalline cellulose, lactose, mannitol, or dicalcium phosphate; the disintegrating agent is starch, pre-gelatinized starch, hydroxypropyl starch, celluloses, cross-linked PVP (crospovidone), sodium starch glycolate, or croscarmellose sodium; and the lubricant is stearic acid, sodium stearyl fumarate, or magnesium stearate.

4. The pharmaceutical formulation of claim 1, wherein the filler is microcrystalline cellulose, the disintegrating agent is crospovidone and the lubricant is magnesium stearate.

5. The pharmaceutical formulation of claim 1, wherein the pharmaceutical formulation comprises about 175 mg of the compound of Formula I.

6. The pharmaceutical formulation of claim 1, wherein the pharmaceutical formulation comprises about 350 mg of the compound of Formula I.

7. The pharmaceutical composition of claim 1, wherein the compound is the freebase of Formula I.

8. The pharmaceutical composition of claim 1, wherein the compound is a crystalline form of the freebase of Formula I which is characterized by an X-ray powder diffraction pattern comprising degree 2θ-reflections (+/−0.2 degrees 2θ) at 9.8°, 16.0°, and 25.4°.

9. A tablet comprising the pharmaceutical formulation of claim 1.

10. The tablet of claim 9, wherein the tablet comprises:
    (i) the compound of Formula I in an amount of about 50 wt %;
    (ii) the filler in an amount of about 44 wt % to about 46 wt %;
    (iii) the disintegrating agent in an amount of about 3 wt % to about 5 wt %; and
    (iv) the lubricant in an amount of about 0.5 wt % to about 2 wt %.

11. The tablet of claim 9, wherein the filler is microcrystalline cellulose, lactose, mannitol, or dicalcium phosphate; the disintegrating agent is starch, pre-gelatinized starch, hydroxypropyl starch, celluloses, cross-linked PVP (crospovidone), sodium starch glycolate, or croscarmellose sodium; and the lubricant is stearic acid, sodium stearyl fumarate, magnesium stearate, or a combination thereof.

12. The tablet of claim 9, wherein the filler is microcrystalline cellulose, the disintegrating agent is crospovidone and the lubricant is magnesium stearate.

13. The tablet of claim 9, wherein the compound is the freebase of Formula I.

14. The tablet of claim 9, wherein the compound is a crystalline form of the freebase of Formula I which is characterized by an X-ray powder diffraction pattern comprising degree 2θ-reflections (+/−0.2 degrees 2θ) at 9.8°, 16.0°, and 25.4°.

15. The tablet of claim 9, comprising:
    (i) the compound of Formula I in an amount of about 175 mg;
    (ii) microcrystalline cellulose in an amount of about 157.5 mg;
    (iii) crospovidone in an amount of about 14 mg; and
    (iv) magnesium stearate in an amount of about 3.5 mg.

16. The tablet of claim 9, comprising:
    (i) the compound of Formula I in an amount of about 350 mg;
    (ii) microcrystalline cellulose in an amount of about 315 mg;
    (iii) crospovidone in an amount of about 28 mg; and
    (iv) magnesium stearate in an amount of about 7 mg.

17. A tablet comprising (a) a tablet core and (b) a film coat; wherein the tablet core comprises:
    (i) about 175 mg or about 350 mg of a compound of Formula I, or a pharmaceutically acceptable salt thereof;

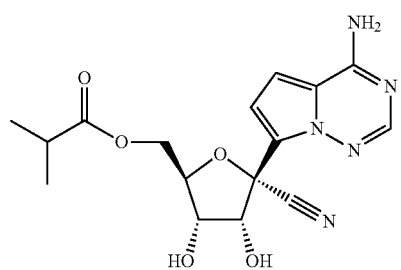

Formula I (ii) a filler;
   (iii) a disintegrating agent; and
   (iv) a lubricant;
wherein the compound of Formula I is present in an amount of about 45 wt % to about 55 wt %.

18. The tablet of claim 17, wherein the tablet core comprises:
    (i) the compound of Formula I in an amount of about 50 wt %;
    (ii) the filler in an amount of about 44 wt % to about 46 wt %;
    (iii) the disintegrating agent in an amount of about 3 wt % to about 5 wt %; and
    (iv) the lubricant in an amount of about 0.5 wt % to about 2 wt %.

19. The tablet of claim 17, wherein the film coat comprises part-hydrolysed PVA, titanium dioxide, macrogol 3350, and talc.

20. The tablet of claim 17, wherein the film coat comprises polyethylene glycol/macrogol polyvinyl alcohol graft copolymer, talc, titanium dioxide, glyceryl mono and dicaprylocaprate, and polyvinyl alcohol.

21. The tablet of claim 17, wherein the film coat is white or yellow.

22. The tablet of claim 17, wherein the filler is microcrystalline cellulose, lactose, mannitol, or dicalcium phosphate; the disintegrating agent is starch, pre-gelatinized starch, hydroxypropyl starch, celluloses, cross-linked PVP (crospovidone), sodium starch glycolate, or croscarmellose sodium; and the lubricant is stearic acid, sodium stearyl fumarate, or magnesium stearate.

23. The tablet of claim 17, wherein the filler is microcrystalline cellulose, the disintegrating agent is crospovidone and the lubricant is magnesium stearate.

24. The tablet of claim 17, wherein the tablet comprises about 175 mg of the compound of Formula I.

25. The tablet of claim 17, wherein the tablet comprises about 350 mg of the compound of Formula I.

26. A tablet comprising (a) a tablet core and (b) a film coat; wherein the tablet core comprises:
(i) a compound of Formula I in an amount of about 175 mg;

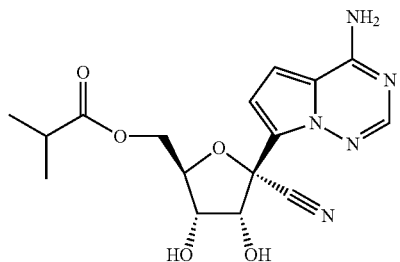

Formula I (ii) microcrystalline cellulose in an amount of about 157.5 mg;
(iii) crospovidone in an amount of about 14 mg; and
(iv) magnesium stearate in an amount of about 3.5 mg; and wherein the film coat comprises polyethylene glycol/macrogol polyvinyl alcohol graft copolymer, talc, titanium dioxide, glyceryl mono and dicaprylocaprate, and polyvinyl alcohol and wherein the film coat is white.

27. A tablet comprising (a) a tablet core and (b) a film coat; wherein the tablet core comprises:
(i) a compound of Formula I in an amount of about 350 mg;

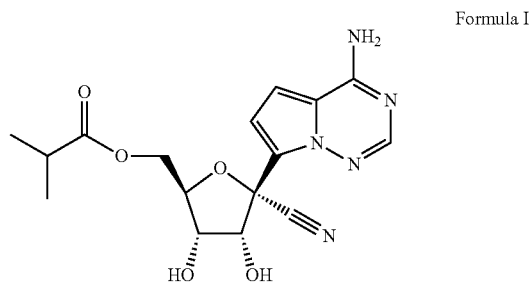 [SMILES: CC(C)C(=O)OC[C@H]1O[C@@](C#N)(c2ccc3c(N)ncnn23)[C@H](O)[C@@H]1O]

Formula I (ii) microcrystalline cellulose in an amount of about 315 mg;
(iii) crospovidone in an amount of about 28 mg; and
(iv) magnesium stearate in an amount of about 7 mg; and wherein the film coat comprises polyethylene glycol/macrogol polyvinyl alcohol graft copolymer, talc, titanium dioxide, glyceryl mono and dicaprylocaprate, and polyvinyl alcohol and wherein the film coat is yellow.

* * * * *